(12) United States Patent
Anantharamaiah et al.

(10) Patent No.: US 9,422,363 B2
(45) Date of Patent: Aug. 23, 2016

(54) SYNTHETIC APOLIPOPROTEIN E MIMICKING POLYPEPTIDES AND METHODS OF USE

(75) Inventors: Gattadahalli M. Anantharamaiah, Birmingham, AL (US); C. Roger White, Maylene, AL (US); Himanshu Gupta, Birmingham, AL (US)

(73) Assignee: UAB RESEARCH FOUNDATION, Birmingham, AL (US)

( * ) Notice: Subject to any disclaimer, the term of this patent is extended or adjusted under 35 U.S.C. 154(b) by 593 days.

(21) Appl. No.: 12/675,089

(22) PCT Filed: Aug. 27, 2008

(86) PCT No.: PCT/US2008/074470
§ 371 (c)(1),
(2), (4) Date: Apr. 21, 2010

(87) PCT Pub. No.: WO2009/032693
PCT Pub. Date: Mar. 12, 2009

(65) Prior Publication Data
US 2010/0298215 A1      Nov. 25, 2010

Related U.S. Application Data

(60) Provisional application No. 60/968,362, filed on Aug. 28, 2007.

(51) Int. Cl.
*C07K 14/775*    (2006.01)
*A61K 38/00*     (2006.01)

(52) U.S. Cl.
CPC .............. *C07K 14/775* (2013.01); *A61K 38/00* (2013.01); *C07K 2319/74* (2013.01)

(58) Field of Classification Search
CPC .................................................. C07K 14/775
See application file for complete search history.

(56) References Cited

U.S. PATENT DOCUMENTS

| | | | |
|---|---|---|---|
| 3,687,808 A | 8/1972 | Englisch et al. |
| 3,767,040 A | 10/1973 | Tushaus |
| 4,155,913 A | 5/1979 | Hellerbach et al. |
| 4,342,566 A | 8/1982 | Theofilopoulos et al. |
| 4,428,938 A | 1/1984 | Kisfaludy et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,643,988 A | 2/1987 | Segrest et al. |
| 4,667,025 A | 5/1987 | Miyoshi et al. |
| 4,684,520 A | 8/1987 | Bertelli |
| 4,762,779 A | 8/1988 | Snitman |
| 4,789,737 A | 12/1988 | Miyoshi et al. |
| 4,816,567 A | 3/1989 | Cabilly et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,868,116 A | 9/1989 | Morgan et al. |
| 4,876,335 A | 10/1989 | Yamane et al. |
| 4,877,611 A | 10/1989 | Cantrell |
| 4,897,355 A | 1/1990 | Eppstein et al. |
| 4,904,582 A | 2/1990 | Tullis |
| 4,946,778 A | 8/1990 | Ladner et al. |
| 4,948,882 A | 8/1990 | Ruth |
| 4,958,013 A | 9/1990 | Letsinger |
| 4,980,286 A | 12/1990 | Morgan et al. |
| 4,981,957 A | 1/1991 | Lebleu et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,135,917 A | 8/1992 | Burch |
| 5,138,045 A | 8/1992 | Cook et al. |
| 5,166,315 A | 11/1992 | Summerton et al. |
| 5,168,053 A | 12/1992 | Altman et al. |
| 5,175,273 A | 12/1992 | Bischofberger et al. |
| 5,176,996 A | 1/1993 | Hogan et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |

(Continued)

FOREIGN PATENT DOCUMENTS

| | | |
|---|---|---|
| AU | 2001286732 | 3/2002 |
| AU | 2003290825 | 11/2003 |

(Continued)

OTHER PUBLICATIONS

Klein R, et al. The association of atherosclerosis, vascular risk factors, and retinopathy in adults with diabetes: the atherosclerosis risk in communities study, Opthalmology 109, pp. 1225-1234 (2002).

(Continued)

*Primary Examiner* — Amber D Steele
(74) *Attorney, Agent, or Firm* — Ballard Spahr LLP

(57) ABSTRACT

The present invention provides methods for using synthetic apolipoprotein E (ApoE)-mimicking peptides. Also disclosed are methods for using synthetic apolipoprotein E (ApoE)-mimicking peptides to reduce plasma glucose levels. Methods of using the disclosed apolipoprotein E (ApoE)-mimicking peptides to treat diabetes and diabetic complications are also disclosed.

13 Claims, 6 Drawing Sheets

(56) References Cited

U.S. PATENT DOCUMENTS

| | | | |
|---|---|---|---|
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,294,533 | A | 3/1994 | Lupski et al. |
| 5,298,490 | A | 3/1994 | Heavner et al. |
| 5,317,098 | A | 5/1994 | Shizuya et al. |
| 5,319,080 | A | 6/1994 | Leumann et al. |
| 5,321,131 | A | 6/1994 | Agrawal et al. |
| 5,334,711 | A | 8/1994 | Sproat et al. |
| 5,344,822 | A | 9/1994 | Levine et al. |
| 5,358,934 | A | 10/1994 | Borovsky et al. |
| 5,359,044 | A | 10/1994 | Cook et al. |
| 5,367,066 | A | 11/1994 | Urdea et al. |
| 5,371,241 | A | 12/1994 | Brush |
| 5,391,377 | A | 2/1995 | Barnwell et al. |
| 5,391,723 | A | 2/1995 | Priest |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,436,330 | A | 7/1995 | Taira et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,135 | A | 10/1995 | Baranowitz .......... 514/725 |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,766 | A | 12/1995 | Gold et al. |
| 5,476,925 | A | 12/1995 | Letsinger et al. |
| 5,480,869 | A | 1/1996 | Wei et al. |
| 5,484,908 | A | 1/1996 | Froehler et al. |
| 5,486,603 | A | 1/1996 | Buhr |
| 5,489,677 | A | 2/1996 | Sanghvi et al. |
| 5,502,177 | A | 3/1996 | Matteucci et al. |
| 5,503,978 | A | 4/1996 | Schneider et al. |
| 5,508,060 | A | 4/1996 | Perman et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,541,313 | A | 7/1996 | Ruth |
| 5,543,293 | A | 8/1996 | Gold et al. |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,332 | A | 10/1996 | Hoogenboom et al. |
| 5,565,552 | A | 10/1996 | Magda et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,579,250 | A | 11/1996 | Balaji et al. |
| 5,580,731 | A | 12/1996 | Chang et al. |
| 5,580,737 | A | 12/1996 | Polisky et al. |
| 5,580,967 | A | 12/1996 | Joyce |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,595,873 | A | 1/1997 | Joyce |
| 5,595,973 | A | 1/1997 | Bogden |
| 5,596,086 | A | 1/1997 | Matteucci et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,612,895 | A | 3/1997 | Balaji et al. |
| 5,614,617 | A | 3/1997 | Cook et al. |
| 5,616,466 | A | 4/1997 | Cantor et al. |
| 5,618,704 | A | 4/1997 | Sanghvi et al. |
| 5,623,070 | A | 4/1997 | Cook et al. |
| 5,624,824 | A | 4/1997 | Yuan et al. |
| 5,625,050 | A | 4/1997 | Beaton et al. |
| 5,627,053 | A | 5/1997 | Usman et al. |
| 5,627,158 | A | 5/1997 | Cho-Chung |
| 5,631,115 | A | 5/1997 | Ohtsuka et al. |
| 5,631,146 | A | 5/1997 | Szostak et al. |
| 5,631,280 | A | 5/1997 | Ciccarone et al. |
| 5,633,133 | A | 5/1997 | Long et al. |
| 5,633,360 | A | 5/1997 | Bischofberger et al. |
| 5,639,873 | A | 6/1997 | Barascut et al. |
| 5,641,754 | A | 6/1997 | Iversen |
| 5,645,985 | A | 7/1997 | Froehler et al. |
| 5,646,020 | A | 7/1997 | Swiggen et al. |
| 5,646,031 | A | 7/1997 | DeYoung et al. |
| 5,646,042 | A | 7/1997 | Stinchcomb et al. |
| 5,646,265 | A | 7/1997 | McGee |
| 5,650,316 | A | 7/1997 | Aggarwal et al. |
| 5,652,094 | A | 7/1997 | Usman et al. |
| 5,652,107 | A | 7/1997 | Lizardi et al. |
| 5,658,873 | A | 8/1997 | Bertsch-Frank |
| 5,663,312 | A | 9/1997 | Chaturvedula |
| 5,670,633 | A | 9/1997 | Cook et al. |
| 5,677,437 | A | 10/1997 | Teng et al. |
| 5,677,439 | A | 10/1997 | Weis et al. |
| 5,681,941 | A | 10/1997 | Cook et al. |
| 5,683,873 | A | 11/1997 | George et al. |
| 5,683,874 | A | 11/1997 | Kool |
| 5,683,902 | A | 11/1997 | Hampel et al. |
| 5,688,670 | A | 11/1997 | Szostak et al. |
| 5,688,941 | A | 11/1997 | Cook et al. |
| 5,691,317 | A | 11/1997 | Cho-Chung |
| 5,693,535 | A | 12/1997 | Draper et al. |
| 5,693,773 | A | 12/1997 | Kandimalla et al. |
| 5,700,920 | A | 12/1997 | Altmann et al. |
| 5,700,922 | A | 12/1997 | Cook |
| 5,712,384 | A | 1/1998 | Symonds et al. |
| 5,714,331 | A | 2/1998 | Buchardt et al. |
| 5,719,262 | A | 2/1998 | Buchardt et al. |
| 5,721,138 | A | 2/1998 | Lawn |
| 5,721,367 | A | 2/1998 | Kay et al. |
| 5,728,521 | A | 3/1998 | Yuan et al. |
| 5,731,295 | A | 3/1998 | Draper et al. |
| 5,731,424 | A | 3/1998 | Toothman et al. |
| 5,733,549 | A | 3/1998 | Yamada et al. |
| 5,733,879 | A | 3/1998 | Rosseneu et al. |

(56) References Cited

U.S. PATENT DOCUMENTS

| | | | |
|---|---|---|---|
| 5,770,576 A | 6/1998 | Morozov ................... 514/19 |
| 5,770,715 A | 6/1998 | Sugiyama et al. |
| 5,780,228 A | 7/1998 | Parma et al. |
| 5,780,607 A | 7/1998 | Goodnow, Jr. et al. |
| 5,786,138 A | 7/1998 | Swenson |
| 5,786,462 A | 7/1998 | Schneider et al. |
| 5,792,613 A | 8/1998 | Schmidt et al. |
| 5,795,721 A | 8/1998 | Rabin et al. |
| 5,800,758 A | 9/1998 | Topolkaraev et al. |
| 5,804,440 A | 9/1998 | Burton et al. |
| 5,807,718 A | 9/1998 | Joyce et al. |
| 5,811,300 A | 9/1998 | Sullivan et al. |
| 5,814,467 A | 9/1998 | Curtiss et al. |
| 5,834,185 A | 11/1998 | Ts'o et al. |
| 5,837,243 A | 11/1998 | Deo et al. |
| 5,837,855 A | 11/1998 | Chowrira et al. |
| 5,843,708 A | 12/1998 | Hardman et al. |
| 5,846,713 A | 12/1998 | Pagratis et al. |
| 5,849,903 A | 12/1998 | Pietrzkowski et al. |
| 5,854,238 A | 12/1998 | Kempen |
| 5,856,103 A | 1/1999 | Gray et al. |
| 5,856,188 A | 1/1999 | Hampel et al. |
| 5,856,463 A | 1/1999 | Prydz et al. |
| 5,858,660 A | 1/1999 | Eaton et al. |
| 5,861,254 A | 1/1999 | Schneider et al. |
| 5,861,288 A | 1/1999 | Usman et al. |
| 5,864,026 A | 1/1999 | Jensen et al. |
| 5,866,701 A | 2/1999 | Hampel et al. |
| 5,869,246 A | 2/1999 | Matsuo et al. |
| 5,869,248 A | 2/1999 | Yuan et al. |
| 5,869,253 A | 2/1999 | Draper |
| 5,869,339 A | 2/1999 | Hampel et al. |
| 5,869,641 A | 2/1999 | Jayasena et al. |
| 5,874,566 A | 2/1999 | Veerapanane et al. |
| 5,877,021 A | 3/1999 | Stinchcomb et al. |
| 5,877,022 A | 3/1999 | Stinchcomb et al. |
| 5,877,153 A | 3/1999 | Harris et al. |
| 5,877,162 A | 3/1999 | Werner et al. |
| 5,891,683 A | 4/1999 | Usman et al. |
| 5,891,684 A | 4/1999 | Usman et al. |
| 5,910,408 A | 6/1999 | Szostak et al. |
| 5,919,772 A | 7/1999 | Szyf et al. |
| 5,939,598 A | 8/1999 | Kucherlapati et al. |
| 5,955,590 A | 9/1999 | Levina et al. |
| 5,958,691 A | 9/1999 | Pieken et al. |
| 5,962,426 A | 10/1999 | Glazer |
| 5,972,699 A | 10/1999 | Draper |
| 5,972,704 A | 10/1999 | Draper et al. |
| 5,985,621 A | 11/1999 | Usman et al. |
| 5,989,906 A | 11/1999 | Thompson |
| 5,989,908 A | 11/1999 | Scanlon |
| 5,990,081 A | 11/1999 | Ageland et al. |
| 5,990,088 A | 11/1999 | Ensoli et al. |
| 5,994,320 A | 11/1999 | Low et al. |
| 5,998,193 A | 12/1999 | Keese et al. |
| 5,998,203 A | 12/1999 | Matulic-Adamic et al. |
| 5,998,602 A | 12/1999 | Torrence et al. |
| 6,001,988 A | 12/1999 | Parma et al. |
| 6,004,925 A | 12/1999 | Dasseux et al. |
| 6,005,013 A | 12/1999 | Suh et al. |
| 6,005,095 A | 12/1999 | Capaccioli et al. |
| 6,007,995 A | 12/1999 | Baker et al. |
| 6,011,002 A | 1/2000 | Pastan et al. |
| 6,011,020 A | 1/2000 | Gold et al. |
| 6,013,443 A | 1/2000 | Heilig et al. |
| 6,013,522 A | 1/2000 | Monia et al. |
| 6,017,756 A | 1/2000 | Draper |
| 6,017,898 A | 1/2000 | Pietrzkowski et al. |
| 6,018,042 A | 1/2000 | Mett et al. |
| 6,444,230 B1 | 1/2000 | Flavahan et al. |
| 6,019,739 A | 2/2000 | Rhee et al. |
| 6,020,130 A | 2/2000 | Gold et al. |
| 6,022,962 A | 2/2000 | Chowrira et al. |
| 6,025,198 A | 2/2000 | Bennett et al. |
| 6,028,186 A | 2/2000 | Tasset et al. |
| 6,030,776 A | 2/2000 | Eaton et al. |
| 6,033,910 A | 3/2000 | Monia et al. |
| 6,037,323 A | 3/2000 | Dasseux et al. |
| 6,040,147 A | 3/2000 | Ridker et al. |
| 6,040,296 A | 3/2000 | Nyce |
| 6,046,004 A | 4/2000 | Wu et al. |
| 6,046,166 A | 4/2000 | Dasseux et al. |
| 6,046,319 A | 4/2000 | Power et al. |
| 6,051,698 A | 4/2000 | Janjic et al. |
| 6,057,437 A | 5/2000 | Kamiya et al. |
| 6,086,918 A | 7/2000 | Stern et al. |
| 6,090,921 A | 7/2000 | Winge et al. |
| 6,107,457 A | 8/2000 | Arlinghaus et al. |
| 6,113,898 A | 9/2000 | Anderson et al. |
| 6,130,364 A | 10/2000 | Jakobovits et al. |
| 6,180,377 B1 | 1/2001 | Morgan et al. |
| 6,191,151 B1 | 2/2001 | Zik |
| 6,201,165 B1 | 3/2001 | Grant et al. |
| 6,228,989 B1 | 5/2001 | Traugh et al. |
| 6,265,377 B1 | 7/2001 | Dasseux et al. |
| 6,287,590 B1 | 9/2001 | Dasseux et al. |
| 6,303,619 B1 | 10/2001 | Linden |
| 6,329,341 B1 | 12/2001 | Dasseux et al. |
| 6,367,479 B1 | 4/2002 | Williams et al. |
| 6,376,464 B1 | 4/2002 | Dasseux et al. |
| 6,383,808 B1 | 5/2002 | Monia et al. |
| 6,410,802 B1 | 6/2002 | Dasseux et al. |
| 6,423,511 B1 | 7/2002 | Nakamura et al. |
| 6,423,830 B1 | 7/2002 | Winge et al. |
| 6,444,111 B1 | 9/2002 | Montgomery |
| 6,444,681 B1 | 9/2002 | Flavahan et al. |
| 6,455,088 B1 | 9/2002 | Dasseux et al. |
| 6,458,592 B1 | 10/2002 | Jakobovits et al. |
| 6,459,003 B1 | 10/2002 | Dasseux et al. |
| 6,464,975 B2 | 10/2002 | Millis |
| 6,472,184 B1 | 10/2002 | Hegemann |
| 6,498,038 B1 | 12/2002 | Ghosh et al. |
| 6,506,799 B1 | 1/2003 | Dasseux et al. |
| 6,506,879 B1 | 1/2003 | Ageland et al. |
| 6,506,880 B2 | 1/2003 | Anantharamaiah |
| 6,514,523 B1 | 2/2003 | Sparks |
| 6,518,412 B1 | 2/2003 | Dasseux et al. |
| 6,555,651 B2 | 4/2003 | Stern et al. |
| 6,559,284 B1 | 5/2003 | Ageland et al. |
| 6,573,239 B1 | 6/2003 | Dasseux et al. |
| 6,602,854 B1 | 8/2003 | Dasseux et al. |
| 6,617,134 B1 | 9/2003 | Sirtori et al. |
| 6,630,450 B1 | 10/2003 | Dasseux et al. |
| 6,635,623 B1 | 10/2003 | Hoogeveen et al. |
| 6,646,170 B2 | 11/2003 | Dasseux et al. |
| 6,664,230 B1 | 12/2003 | Fogelman et al. |
| 6,673,780 B2 | 1/2004 | Dasseux et al. |
| 6,680,203 B2 | 1/2004 | Dasseux et al. |
| 6,696,545 B1 | 2/2004 | Buelow et al. |
| 6,699,910 B2 | 3/2004 | Dasseux et al. |
| 6,703,422 B2 | 3/2004 | Dasseux et al. |
| 6,713,507 B2 | 3/2004 | Dasseux et al. |
| 6,716,816 B1 | 4/2004 | Dasseux et al. |
| 6,717,031 B2 | 4/2004 | Games et al. |
| 6,727,063 B1 | 4/2004 | Lander et al. |
| 6,734,169 B2 | 5/2004 | Dasseux et al. |
| 6,753,313 B1 | 6/2004 | Dasseux et al. |
| 6,773,719 B2 | 8/2004 | Rodrigueza et al. |
| 6,790,953 B2 | 9/2004 | Dasseux et al. |
| 6,831,105 B2 | 12/2004 | Dasseux et al. |
| 6,846,636 B1 | 1/2005 | Argraves et al. |
| 6,849,714 B1 | 2/2005 | Bridon et al. |
| 6,869,568 B2 | 3/2005 | Fogelman et al. |
| 6,887,470 B1 | 5/2005 | Bridon et al. |
| 6,909,014 B2 | 6/2005 | Dasseux et al. |
| 6,930,085 B2 | 8/2005 | Fogelman et al. |
| 6,933,279 B2 | 8/2005 | Fogelman et al. |
| 6,936,691 B2 | 8/2005 | Fiscella et al. |
| 6,982,348 B2 | 1/2006 | Kori et al. |
| 7,144,862 B2 | 12/2006 | Fogelman et al. |
| 7,148,197 B2 | 12/2006 | Fogelman et al. |
| 7,148,199 B2 | 12/2006 | Neu ................... 514/19 |
| 7,166,578 B2 | 1/2007 | Fogelman et al. |
| 7,189,689 B2 | 3/2007 | Dasseux et al. |

(56) References Cited

U.S. PATENT DOCUMENTS

| | | | |
|---|---|---|---|
| 7,192,940 B2 | 3/2007 | Dasseux et al. | |
| 7,199,102 B2 | 4/2007 | Fogelman et al. | |
| 7,211,565 B2 | 5/2007 | Dasseux et | |
| 7,217,785 B2 | 5/2007 | Bielicki | |
| 7,291,590 B2 | 11/2007 | Kisilevsky et al. | |
| 7,312,190 B2 | 12/2007 | Dasseux et al. | |
| 7,427,662 B2 | 9/2008 | Hornick et al. | |
| 7,470,660 B2 | 12/2008 | Schwartz et al. | |
| 7,531,514 B2 | 5/2009 | Fogelman et al. | |
| 7,563,771 B2 | 7/2009 | Anantharamiah et al. | |
| 7,579,319 B2 | 8/2009 | Fogelman et al. | |
| 7,638,494 B2 | 12/2009 | Fogelman et al. | |
| 7,723,303 B2 * | 5/2010 | Fogelman et al. | 435/6.16 |
| 8,084,423 B2 | 12/2011 | Anantharamiah et al. | |
| 2001/0005714 A1 | 6/2001 | Boffelli et al. | |
| 2002/0042441 A1 | 4/2002 | Acton et al. | |
| 2002/0071862 A1 | 6/2002 | Williams et al. | |
| 2002/0128175 A1 | 9/2002 | Anantharamaiah | |
| 2002/0142369 A1 | 10/2002 | Fersht | |
| 2003/0027769 A1 | 2/2003 | Scialdone et al. | |
| 2003/0040505 A1 | 2/2003 | Fogelman et al. | |
| 2003/0045460 A1 | 3/2003 | Fogelman et al. | |
| 2003/0077641 A1 | 4/2003 | Laskowitz et al. | |
| 2003/0087819 A1 | 5/2003 | Bielicki | |
| 2003/0109442 A1 | 6/2003 | Bisgaier et al. | |
| 2003/0125260 A1 | 7/2003 | Haviv et al. | |
| 2003/0203842 A1 | 10/2003 | Dasseux et al. | |
| 2003/0229015 A1 | 12/2003 | Fogelman et al. | |
| 2004/0059110 A1 | 3/2004 | Nakano et al. | |
| 2004/0122091 A1 | 6/2004 | Dasseux et al. | |
| 2004/0136989 A1 | 7/2004 | Banerjee et al. | |
| 2004/0152623 A1 | 8/2004 | Varadhachary et al. | |
| 2004/0186057 A1 | 9/2004 | Anantharamiah et al. | |
| 2004/0224011 A1 | 11/2004 | Rodrigueza et al. | |
| 2004/0266663 A1 | 12/2004 | Schwartz et al. | |
| 2004/0266671 A1 | 12/2004 | Fogelman et al. | |
| 2005/0070996 A1 | 3/2005 | Dinh et al. | |
| 2005/0154046 A1 | 7/2005 | Wang et al. | |
| 2005/0164950 A1 | 7/2005 | Fogelman et al. | |
| 2005/0197381 A1 | 9/2005 | Wang et al. | |
| 2005/0239136 A1 | 10/2005 | Hazen et al. | |
| 2006/0069030 A1 | 3/2006 | Bachovchin | |
| 2006/0172919 A1 | 8/2006 | Hornick et al. | |
| 2006/0173067 A1 | 8/2006 | Fogelman et al. | |
| 2006/0205634 A1 | 9/2006 | Varadhachary et al. | |
| 2006/0205669 A1 | 9/2006 | Fogelman et al. | |
| 2006/0217298 A1 | 9/2006 | Srivastava | |
| 2006/0217307 A1 | 9/2006 | Takashi et al. | |
| 2006/0234908 A1 | 10/2006 | Fogelman et al. | |
| 2007/0032430 A1 * | 2/2007 | Fogelman et al. | 514/13 |
| 2007/0060527 A1 | 3/2007 | Fogelman et al. | |
| 2007/0071756 A1 | 3/2007 | Peyman | |
| 2007/0101448 A1 | 5/2007 | Anantharamiah et al. | |
| 2007/0254839 A1 | 11/2007 | Fogelman et al. | |
| 2008/0045459 A1 | 2/2008 | Fogelman et al. | |
| 2008/0095821 A1 | 4/2008 | Fogelman et al. | |
| 2008/0096814 A1 | 4/2008 | Fogelman et al. | |
| 2008/0096815 A1 | 4/2008 | Fogelman et al. | |
| 2008/0096816 A1 | 4/2008 | Fogelman et al. | |
| 2008/0293639 A1 | 11/2008 | Fogelman et al. | |
| 2009/0163408 A1 | 6/2009 | Fogelman et al. | |
| 2009/0286741 A1 | 11/2009 | Fogelman | |
| 2010/0286025 A1 | 11/2010 | Anantharamiah et al. | |

FOREIGN PATENT DOCUMENTS

| | | | |
|---|---|---|---|
| AU | 2003290825 A1 | 6/2004 | |
| AU | 2005287004 | 3/2006 | |
| AU | 2008296487 | 8/2008 | |
| AU | 2008296478 A1 | 3/2009 | |
| CA | 2420222 | 2/2002 | |
| CA | 25143033 | 11/2003 | |
| CA | 2580501 | 3/2006 | |
| CA | 2697957 | 8/2008 | |
| CA | 2514303 A1 | 9/2012 | |
| EP | 1186299 | 3/2002 | |
| EP | 1318828 A1 | 6/2003 | |
| EP | 03783409.0 | 11/2003 | |
| EP | 1562624 A2 | 8/2005 | |
| EP | 1599173 A2 | 11/2005 | |
| EP | 1799242 A2 | 6/2007 | |
| EP | 08829135.6 | 8/2008 | |
| EP | 2195340 A2 | 6/2010 | |
| EP | 2195331 A2 | 11/2013 | |
| EP | 2682400 A2 | 1/2014 | |
| JP | 61-126099 | 6/1986 | |
| JP | 7-507554 | 8/1995 | |
| JP | 2010-537638 | 12/2010 | |
| JP | 2010-538005 | 12/2010 | |
| NZ | 541504 | 11/2003 | |
| NZ | 541504 | 8/2009 | |
| WO | WO 93/25581 | 12/1993 | |
| WO | WO 97/36927 | 10/1997 | |
| WO | WO 98/09602 | 3/1998 | |
| WO | WO 99/16408 | 4/1999 | |
| WO | WO 99/16409 | 4/1999 | |
| WO | WO 99/47566 | * 9/1999 | C07K 17/00 |
| WO | WO 01/75168 | 10/2001 | |
| WO | WO 01/75170 | 10/2001 | |
| WO | WO 02/15923 | 2/2002 | |
| WO | WO 02/098446 | 12/2002 | |
| WO | WO 03/086326 | 10/2003 | |
| WO | WO 03/089612 | * 10/2003 | |
| WO | PCT/US2003/036268 | 11/2003 | |
| WO | WO 2004/027027 | 4/2004 | |
| WO | WO 2004/034977 | 4/2004 | |
| WO | WO 2004/043396 | 5/2004 | |
| WO | WO-2004/043403 | 5/2004 | |
| WO | WO 01/75067 | 10/2004 | |
| WO | WO 2005/016280 | 2/2005 | |
| WO | WO 2006/020652 | 2/2006 | |
| WO | WO-2006/034056 A2 | 3/2006 | |
| WO | WO 2006/063132 | 6/2006 | |
| WO | WO 2006/118805 | 11/2006 | |
| WO | WO2006118805 | * 11/2006 | A61K 38/17 |
| WO | WO 2008/021088 | 2/2008 | |
| WO | WO-2009/032693 A2 | 3/2009 | |
| WO | WO-2009/032702 A2 | 3/2009 | |
| WO | WO 2009/073725 | 6/2009 | |
| WO | WO-2009/100348 A2 | 8/2009 | |

OTHER PUBLICATIONS

Roscoe, et al. Lipid changes in the eye concomitant with the development of atherosclerosis in the aorta in the rabbit, Circ Res 23, pp. 633-643 (1968).

Preliminary Amendment filed Jul. 6, 2010 with the USPTO for U.S. Appl. No. 12/675,073, filed Mar. 22, 2010 (1st Named Inventor—Anantharamiah) (3 pages).

Preliminary Amendment filed Jul. 14, 2010 with the USPTO for U.S. Appl. No. 12/675,073, filed Mar. 22, 2010 (1st Named Inventor—Anantharamiah) (3 pages).

Requirement for Restriction/Election mailed Jul. 9, 2012 by the USPTO for U.S. Appl. No. 12/675,073, filed Mar. 22, 2010 (1st Named Inventor—Anantharamiah) (6 pages).

Response to Restriction Requirement filed Sep. 12, 2012 with the USPTO for U.S. Appl. No. 12/675,073, filed Mar. 22, 2010 (1st Named Inventor—Anantharamiah) (8 pages).

Non-final Rejection mailed Jan. 13, 2012 by the USPTO for U.S. Appl. No. 12/027,728, filed Feb. 7, 2008 (1st Named Inventor—Anantharamiah) (14 pages).

Response to Non-final Rejection filed Apr. 10, 2012 with the USPTO for U.S. Appl. No. 12/027,728, filed Feb. 7, 2008 (1st Named Inventor—Anantharamiah) (15 pages).

Non-final Rejection mailed Jun. 14, 2012 by the USPTO for U.S. Appl. No. 12/027,728, filed Feb. 7, 2008 (Inventor—Anantharamiah) (10 pages).

Non-Final Rejecton issued on Nov. 1, 2013 or U.S. Appl. No. 21/865,957, filed Oct. 15, 2010 (Applicants—UAB Research Foundation; Inventors—Anantharamiah et al.) (6 pages).

(56) References Cited

OTHER PUBLICATIONS

Response to Restriction Requirement filed on Jul. 23, 2013 for U.S. Appl. No. 21/865,957, filed Oct. 15, 2010 (Applicants—UAB Research Foundation; Inventors—Anantharamaiah et al.) (6 pages).
Requirement for Restriction/Election issued on Feb. 1, 2013 for U.S. Appl. No. 12/865,957, filed Oct. 15, 2010 (Applicants—UAB Research Foundation; Inventors—Anantharamaiah et al.) (8 pages).
Requirement for Restriction/Election issued on Nov. 27, 2013 for U.S. Appl. No. 13/804,161, filed Mar. 14, 2013 (Applicants—UAB Research Foundation; Inventors—Anantharamaiah et al.) (7 pages).
Extended European Search Report issued on Dec. 13, 2013 for European Pat. App. No. 13187186.5 filed Oct. 7, 2013 (Applicants—UAB Research Foundation; Inventors—Anantharamaiah et al.) (10 pages).
Grundy SM. (1999) Hypertriglyceridemia, insulin resistance, and the metabolic syndrome. The American Journal of Cardiology, 83(9): 25-29.
Grundy SM. (1998) Hypertriglyceridemia, Atherogenic Dyslipidemia, and the Metabolic Syndrome. The American Journal of Cardiology, 81(4): 18B-25B.
Gupta H, et al. (2005) Apolipopprotein E mimetic Peptide dramatically lowers plasma cholesterol and restores endothelial function in watanabe heritable hyperlipidemic rabbits. Circulation, 111(23): 3112-3118.
Johnson JH. (2006) Trends and opportunities in the metabolic syndrome. Drug Development Research, 67(7): 539-544.
Moller DE, et al. (2005) Metabolic Syndrome: A Clinical and Molecular Perspective. Annual Review of Medicine: Selected Topics in the Clinical Sciences, 45: 25-62.
Rembold CM. (2004) Combination therapy of dyslipidemia in non-insulin-dependent diabetes mellitus and the metabolic syndrome. Current Diabetes Reports, 330-334.
U.S. Appl. No. 10/269,755, Oct. 11, 2002, Fogelman et al.
U.S. Appl. No. 11/541,481, Sep. 29, 2006, Fogelman et al.
U.S. Appl. No. 11/541,482, Sep. 29, 2006, Fogelman et al.
U.S. Appl. No. 11/541,494, Sep. 29, 2006, Fogelman et al.
Abrahmsen et al. (1991) Biochemistry 30: 4151.
Acsadi G et al. (1991) Human dystrophin expression in mdx mice after intramuscular injection of DNA constructs. Nature, 352(6338): 815-8.
Adachi, T., et al., (2003) Biochemical J. 289(2):523-527.
Aikawa, M., et al., Lipid Lowering Reduces Oxidative Stress and Endothelial Cell Activation in Rabbit Atheroma. Circulation (2002) 106:1390-1396.
Ajees et al. (2006) Crystal structure of human apolipoprotein A-1: Insights into its protective effect against cariodvascular diseases. PNAS 103:2126-2131.
Ali, et al. (2005). Apolipoprotein E suppresses the Type I inflammatory response in vivo. Circ. Res. 97:922-927.
Ambati, J. et al. (2003) Age-related macular degeneration: etiology, pathogenesis, and therapeutic strategies. Surv Ophthalmol. 48(3): 257-293.
Anantharamaiah et al. (1985) Studies of Synthetic Peptide of the Amphipathic Helix. The Journal of Biological Chemistry 260:10248-10255.
Anantharamaiah et al. (1988) Effect of Oxidation on the Properties of Apolipoproteins A-I and A-II. J. Lipid Res. 29:309-318.
Anantharamaiah et al. (1990) Use of Synthetic Peptide Analogues to Localize Lecithin: Cholseterol Acyltransf erase Activating Domain in Apolipoprotein A-I. Arteriosclerosis 10: 95-105.
Anantharamaiah G et al., (2006) Synthetic peptides: managing lipid disorders. Curr Opin Lipidol. 17(3): 233-237.
Anantharamaiah et al. (2007) Structural requirements for antioxidative and a enti-inflammatory properties of apolipoprotein A-I mimetic peptides. J Lipid Res. 48(9): 1915-1923.
Anantharamaiah, G.M. et al., (2001) Toward the design of peptide mimics of antiatherogenic apolipoproteins A-I and E., Current Science 81:53-65.
Aoyagi H et al. (1988) Synthesis of antibacterial peptides-gramicidin S analogs and designed amphiphilic oligopeptides. Tetrahedron; 44:877-886.

Aravinda, S. et al., (2003) Aromatic-Aromatic Interactions in Crystal Structures of Helical Peptide Scaffolds Containing Projecting Phenylalinine Residues, J. Am Chem Soc.; 125:5308 5315.
Armitage et al., (1997) Peptide nucleic acid—DNA duplexes: Long range hole migration from an internally linked anthraquinone. Proc Natl Acad Sci USA.; 94(23):12320-5.
Ashby D, (2001) Lack of effect of serum amyloid A (SAA) on the ability of high-density lipoproteins to inhibit endothelial cell adhesion molecule expression. Atherosclerosis. 154:113-121.
Ashby et al., (1998) Factors influencing the ability of HDL to inhibit expression of vascular cell adhesion molecule-1 in endothelial cells. Arteriosclerosis. Thrombosis and Vascular Biology, 18:1450-1455.
Badimon et al., (1990) Regression of Atherosclerotic Lesions by High Density Lipoprotein Iasma Fraction in the Cholesterol-fed Rabbit. J. Clinical Investigation 85:1234-1241.
Baggiolini et al. Interleukin-8, a chemotactic and inflammatory cytokine FEBS Lett. 307: 97-101, (1992).
Bailey et al. (2001) Clusterin, a binding protein with a molten globule-like region. Biochemistry. 40(39): 11828-11840.
Baker et al. (1999) Ability of reconstituted high density lipoproteins to inhibit cytokine-induced expression of vascular cell adhesion molecule-1 in human umbilical cell endothelial cells. J Lipid Res, 1999, 40:345-353.
Baker et al. (2000) Phospholipid composition of reconstituted high density lipoproteins influences their ability to inhibit endothelial cell adhesion molecule expression. J Lipid Res, 2000;41:1261-1267.
Barengolts et al. (1998) Osteoporosis and coronary atherosclerosis in asymptomatic postmenopausal women. Calcif Tissue Int. 62(3): 209-213.
Barter, P.J. and Rye, K-A. High density lipoproteins and coronary heart disease. Atherosclerosis, 1996, 121:1-12.
Baumbach et al. (2002) Structure of Cerebral Arterioles in Cystathionine B-SynthaseDeficient Mice, Circulation Res., 91: 931-937.
Baumbach et al. (2003) Cerebral Arteruikar Structure in Mice Overexpressing Human Renin and Angiotensinogen, Hypertension, 41: 50-55.
Beatty S, Koh H, Phil M, Henson D, Boulton M. (2000) The role of oxidative stress in the pathogenesis of age-related macular degeneration. Surv Ophthalmol. 45(2): 115-134.
Bechinger B. (2000) Understanding peptide interactions with the lipid bilayer: a guide to membrane protein engineering. Curr Opin Chem Biol. 4(6):639-644.
Beisiegel, U. et al. The LDL-receptor-related protein, LRP, is an apolipoprotein E-binding protein. Nature 341: 162-164 (1989).
Berkner et al. (1987) Abundant Expression of Polyomavirus Middle T Antigen and Dihydrofolate Reductase in an Adenovirus Recombinant. J. Virology 61:1213-1220.
Besiegel, U. et al. (1991) Lipoprotein lipase enhances the binding of chylomicrons to low density lipoprotein receptor-related protein Proc. Natl. Acad. Sci. U.S.A. 88:8342-8346.
Betteridge, D.J., Long-term risk reduction: Who needs treatment?, Diabetes Research and Clinical Practice. (2005) 68S2:S15-2.
Bisoendial et al. (2003) Restoration of Endothelial Function by Increasing High-Density Lipoprotein in Subjects With Isolated Low High-Density Lipoprotein Circulation 107: 2944-2948.
Blackburn WD Jr, et al. (1991) Apolipoprotein A-I decreases neutrophil degranulation and superoxide production. J Lipid Res. 32(12): 1911-1918.
Blankenberg et al. (2001) Circulating cell adhesion molecules and death in patients with coronary artery disease. Circulation 2001;104:1336-1342.
Boerner et al. (1991) Production of Antigen-Specific Human Monoclonal Antibodies from In Vitro-Primed Human Splenocytes. J. Immunol., 147(1):86-95.
Boffa et al., Isolation of active genes containing CAG repeats by DNA strand invasion by a peptide nucleic acid. Proc Natl Acad Sci USA. Mar. 14, 1995; 92(6):1901-5.
Boffelli et al. (1997) Reconstitution and Further Characterization of the Cholesterol Transport Activity of the Small-Intestinal Brush Border Membrane Biochemistry 36:10784-10792.

(56) References Cited

OTHER PUBLICATIONS

Boffelli et al., (1997) The uptake of cholesterol at the small-intestinal brush border membrane is inhibited by apolipoproteins. FEBS Letters, 411: 7-11.
Borhani et al. (1999) Crystal structure of truncated human apolipoprotein A-1 suggests a lipid bound conformation. Proc. Natl. Acad. Sci. USA. 94:12291-12296.
Bourdillon et al. (2000) ICAM 1 deficiency reduces atherosclerotic lesions in double-knockout mice (ApoE(–/) IICAM-1(–/–)) fed a fat or a chow diet. Arterioscler Thromb Vasc Biol 2000;20:2630-2635.
Bowry et al. (1992) High density lipoprotein is the major carrier of lipid hydroperoxides in human blood plasma from fasting donors. Proc Natl Acad Sci USA. 1992;89:10316-10320.
Braddock. D. T., et al., (1996) Conformationally Specific Enhancement of Receptor-ediated LDL Binding and Internalization by Peptide Models of a Conserved Anionic N-Termina Domain of Human Apolipoprotein E. Biochemistry 35. 13975-13984.
Bradley, W.A., et al., (1986) ApoE is necessary and sufficient for the binding of large triglyceride-rich lipoproteins to the LDL receptor; apoB is unnecessary. J. Lipid Res. 27, 40-48.
Bradley et al. (1982) Apolipoprotein E degradation in human very low density lipoproteins by protease(s): chemical and biological consequences. Biochim. Biophys. Res. Commun. 109:1360-1367.
Brigham et al. (1989) Expression of a prokaryotic gene in cultured lung endothelial cells after lipofection with a plasmid vector. Am. J. Resp. Cell. Mol. Biol. 1: 95-100.
Brousseau, M.E. (2005) Emerging role of high-density lipoprotein in the prevention of cardiovascular disease. Drug Discovery Today. 10:1095-1099.
Brousseau, M.E., and Hoeg, J.M. (1999) Transgenic rabbits as models for atherosclerosis research. J. lipid Res. 40:365-375.
Brown, D.T. and Burlingham, B.T., (1973) Penetration of Host Cell Membranes by Adenovirus 2 J. Virology 12:386-396.
Brown, B.G. et al. (2001) Simvastatin and Niacin, Antioxidant Vitamins, or the Combination for the Prevention of Coronary Disease. N. Engl J Med. 345(22):1583-92.
Brown M.L., et al. (2000) A Macrophage Receptor for Apolipoprotein B48: Clining, Expression, and Atherosclerosis. Proc. Natl. Acad. Sci. USA 97:7488-7493.
Burger et al. (2002) High-density lipoprotein-associated apolipoprotein A-I: the missing link between infection and chronic inflammation? Autoimmunity Reviews 2002;1:111-117.
Burnett, J.R. and Vasikaran, S.D. (2002) Cardiovascular disease and osteoporosis: is there a link between lipids and bone? Ann Clin Biochem. 39(Pt 3): 203-210.
Calabresi L, et al. (2002) Elevated cellular adhesion molecules in subjects with low ML- cholesterol. Arterioscler Thromb Vasc Biol. ;22:656-661.
Calabresi L, Franceschini G, Sirtoh CR, De Palma A, Saresella M, Ferrante P, Taramelli D Inhibition of VCAM-1 expression in endothelial cells by reconstituted high density lipoproteins. Biochem Biophys Res Commun. (1997) 238:61-65.
Calabresi, L., et al., (2003) Entothelial Protection by High-Denisty Lipoproteins. Athero. Thromb. Vasc. Biol. 23:1724-1731.
Campbell, E.J. Human leukocyte elastase, cathepesin G and lactoferrin: family of neutrophil granule glycoproteins that bind to an alveolar macrophage receptor. Proc Natl Acad Sci USA (1982) 79:6941-6945.
Cardillo, C. et al., (1997) Xanthine Oxidase Inhibition With Oxypurinol Improves Endothelial Vasodilator Function in Hypercholesterolemic but Not in Hypertensive Patients. Hypertension 30:57-63.
Carlos TM, et al. (1990) Vascular cell adhesion molecule-1 mediates lymphocyte adherence to cytokine-activated cultured human endothelial cells. Blood;76:965-970.
Carr, A.C. et al. (2000) Oxidation of LDL by myeloperoxidase and reactive nitrogen species oxidation of LDL by myeloperoxidase and reactive nitrogen species. Arterioscler Thromb Vasc Biol; 20:1716-1723.

Carrara et al., Two helices plus a linker: A small model substrate for eukaryotic RNase P Proc. Natl. Acad. Sci. (USA) 92:2627-2631 (1995).
Casserly, I. and Topol, E. (2004) Convergence of atherosclerosis and Alzheimer's disease: inflammation, cholesterol, and misfolded proteins Lancet 363:1139-1146.
Castelli, W.P. et al., Incidence of coronary heart disease and lipoprotein cholesterol levels. The Framingham study. JAMA. 1986; 256:2835. Abstract.
Catapano, A.L. et al. Suppression of 3-hydroxy-3-methylglutaryl-CoA reductase by low density lipoproteins produced in vitro by lipoprotein lipase action on nonsuppressive very low density lipoproteins. J. Biol. Chem. 254: 1007-1009 (1979).
Charles-Schoeman C, Banquerigo ML, Hama S, Navab M, Park GS, Van Lenten BJ, Wagner AC, Fogelman AM, Brahn E. (2008) Treatment with an apolipoprotein A-1 mimetic peptide in combination with pravastatin inhibits collagen-induced arthritis. Clin Immunol. 127(2): 234-244.
Chiesa G, et al., Recombinant apolipoprotein A-I(Milano) infusion into rabbit carotid artery rapidly removes lipid from fatty streaks. Circ Res. 2002;90:974-980.
Chillon, J. and Baumbach, G.L. (1999) Effects of an Angiotensin-Converting Enzyme Inhibitor and a b-Blocker on Cerebral Arterioles in Rats Hypertension, 33: 856-861.
Chorev, M. and Goodman, M. (1995) Recent developments in retro peptides and proteins—an ongoing topochemical exploration. Trends Biotechnol. 13(10): 438-445.
Christison J, (1996) Rapid reduction and removal of HDL- but not LDL- associated cholesteryl ester hydroperoxides by rat liver in situ. Biochem J.; 314:739-742.
Chung, B.H. et al. Liposome-like Particles Isolated From Human Atherosclerotic Plaques Are Structurally and Compositionally Similar to Surface Remnants of Triglyceride-Rich Lipoproteins. Arterio. Thromb. 14:622-635 (1994).
Chung et al., (1985) Studies of Synthetic Peptide Analogs of the Amphipathic Helix. J. Biol. Chem. 60(18): 10256-10262.
Chung, B.H., et al. (1996) Probing structure and function of VLDL by synthetic amphipathic helical peptides. J. Lipid Res. 37:1099-1112.
Clark-Lewis et al. (1991) Chemical Synthesis, Purification, and Characterization of Two Inflammatory Proteins, Neutrophil Activating Peptide 1 (Interleukin-8) and Neutrophil Activating Peptide 2. Biochemistry 30: 3128-3135.
Clark-Lewis I, et al. (1994) Structural requirements for interleukin-8 function identified by design of analogs and CXC chemokine hybrids. J Biol Chem. 269(23): 16075-16081.
Clay, M.A., et al. (2001) Time sequence of the inhibition of endothelial adhesion molecule expression by reconstituted high density liprotes, Atherosclerosis 157: 23-29.
Clay, M.A. et al. (1995) Localization of a domain in apolipoprotein E with both cytostatic and cytotoxic activity. Biochemistry. 34:11142-11151.
Clee, S.M., et al. (2000) Age and residual cholesterol efflux affect HDL cholesterol levels and coronary artery disease in ABCA1 hetrozygotes. J. Clin. Invest. 106:1263-1270.
Clubb, F.J., et al. (2001) Development of atherosclerotic plaque with endothelial disruption in Watanabe heritable hyperlipidemic rabbit aortas. Cardiovasc. Pathol. 9:1-11.
Cockerill, G.W. et al. (2001) Elevation of plasma high-density lipoprotein concentration reduces interleukin-I induced expression of E-selectin in an in vivo model of acute inflammation. Rculation;103:108-112.
Cockerill, G.W. et al. (1999) High-density lipoproteins differentially modulate cytokine induced expression of E-selectin and cyclooxygenase-2. Arterioscler Thromb Vasc Biol.;19:910-917.
Cockerill, G.W. et al. (1995) High-density lipoproteins inhibit crone-induced expression of endothelial cell adhesion molecules. Arterioscler Thromb Vasc Biol. 15:1987-1994.
Collard, M.W. and Griswold, M.D. (1987) Biosynthesis and molecular cloning of sulfated glycoprotein 2 secreted by rat Sertoli cells. Biochemistry. 26(12): 3297-3303.
Colles, S.M., Masson, J.M., Carlson, S.G., and Chisom, G.M., Oxidized LDL-induced injury and apoptosis in atherosclerosis. Potential roles for oxysterols. Trends Cardiovasc. Med. 11:131-138 (2001).

(56) References Cited

OTHER PUBLICATIONS

Bergt, C. et al., (2004) The myeloperoxidase product hypochlorous acid oxidizes HDL in the human artery wall and impairs ABCA1-dependent cholesterol transport Natl.. Acad. Sci. U.S.A. 101:13032-13037.

Corey, D.R. Peptide nucleic acids: expanding the scope of nucleic acid recognition. Trends Biotechnol Jun. 1997; 15(6):224-9.

Coyne, E.F. et al. (2002) Methods for isolation and characterization of intracerebral arterioles in the C57/13L6 wild-type mouse, J. Neurosci. Meth., 120: 145-153.

Curcio, C.A. et al. (2001) Accumulation of cholesterol with age in human Bruch's membrane. Invest Ophthalmol Vis Sci. 42(1): 265-274.

Curcio CA, et al. (2005) Esterified and unesterified cholesterol in drusen and basal deposits of eyes with age-related maculopathy. Exp Eye Res. 81(6): 731-741.

Cybulsky MI, et al., (2001) A major role for VCAM-1, but not ICAM-I, in early atherosclerosis. Journal of Clinical Investigation;107:1255-1262.

Cyrus, et al., (2001) Absence of 12/15-lipoxygenase expression decreases lipid peroxidation and atherogenesis in apolipoprotein E-deficient mice. Circulation;103:2277-2282.

Dai et al. (2004) Implantation of Immature Neonatal Cardiac Cells Into the Wall of the Aorta in Rats: A Novel Model for Studying Morphological and Functional Development of Heart Cells in an Extracardiac Environment. Circulation. 110(3): 324-329.

Dai et al. (2005) Allogeneic mesenchymal stem cell transplantation in postinfarcted rat myocardium: short- and long-term effects. Circulation 112(2): 214-223.

Dansky HM, et al., Adhesion of monocytes to arterial endothelium and initiation of atherosclerosis are critically dependent on vascular cell adhesion molecule-1 gene dosage. Arterioscler Thromb Vasc Biol 2001; 21:1662-1667.

Dansky HM, et al. (1999), Apo A-I inhibits foam cell formation in Apo E-deficient mice after monocyte adherence to endothelium. J Clin Invest.;104:31-39.

Dashti et al. (2004) Model class A and class L peptides increase the production of apoA-I-containing lipoproteins in HepG2 cells. Journal of Lipid Res. 45: 1919-1928.

Datta et al. (2001) Effects of Increasing Hydrophobicity on the Physical-Chemical and Biological Properties of a Class A Amphipathic Helical Peptide. J Lipid Research 42:1096-1104.

Datta et al. The Receptor Binding Domain of Apolipoprotein E, Linked to a Model Class A Amphipathic Helix, Enhances Internalization and Degradation of LDL by Fibroblasts. Biochemistry 30: 213-220 (2000).

Datta et al., (2001) Cationic Domain (141-150) of Apo E Linked to a Class A Amphipathic Helix Enhances the Metabolism of Apo a-Containing Lipoproteins in Hepatocytes. Arterio. Thromb. Vasc. Biol. 21:651.

Datta et al. (2001) Cationic domain 141-150 of apoE covalently linked to a class A amphipathic helix enhances atherogenic lipoprotein metabolism in vitro and in vivo. Journal of Lipid Research 42:959-966.

Datta G, et al. (2009) Anti-inflammatory and recycling properties of an apolipoprotein mimetic peptide, Ac-hE18A-NH(2). Atherosclerosis Epub ahead of print. Volume and page TBA.

Datta, G. et al. (2004) Aromatic Residue Position on the Nonpolar Face of Class A Amphipathic Helical Peptides Determines Biological Activity. J. Biol. Chem. 279:26509-26517.

Davenport, P. and Tipping, P.G. (2003) The role of interleukin-4 and interleukin-12 in the progression of atherosclerosis in apolipoprotein E-deficient mice. Am J Pathol 163:1117-1125.

Davidson, D. et al. Overproduction of Polyomavirus Middle T Antigen in Mammalian Cells through the Use of an Adenovirus Vector. J. Virology 61:1226-1239 (1987).

Davidson, et al. (1994) The Influence of Apolipoprotein Structure on the Efflux of Cellular Free Cholesterol to High Density Lipoprotein. J. Biol. Chem. 269(37): 22975-22982.

Dawson, P.E. et al. Synthesis of Proteins by Native Chemical Ligations. Science 266: 776-779 (1994).

De Caterina R, et al., (1998) Structural requirements for inhibition of cytokine-induced endothelial activation by unsaturated fatty acids. J. Lipid Res.;39:1062-1070.

Diederich et al. (2001) Apolipoprotein A1 and HDL3 Inhibit Spreading of Primary Human Monocytes through a Mechanism that Involves Cholesterol Depletion and Regulation of CD42, Atherosclerosis. 159:313-324.

Dimayuga, P. et al., Reconstituted HDL containing human apolipoprotein A-1 reduces VCAM-1 expression and neointima formation following periadventitial cuffinduced carotid injury in apoE null mice. Biochem Biophys Res Commun. 1999;264:465-468.

Dithmar S, et al. (2000) Ultrastructural changes in Bruch's membrane of apolipoprotein E-deficient mice. Invest Ophthalmol Vis Sci. 41(8): 2035-2042.

Dooley, C.T. et al. (1994) An All D-Amino Acid Opioid Peptide with Central Analgesic Activity from a Combinatorial Library. Science. 2019-2022.

Dunlop, D.S. and Neidle, A. (1997) The Origin and Turnover of D-Serine in Brain. Biochemical and Biophysical Research Communication 235:26-30.

Duong, P. T., et al. (2006). Characterization of nascent HDL particles and macroparticles formed by ABC A1-mediated cholesterol efflux of cellular lipids to apo A-I. J. Lipid Res. 47:832-843.

Dyer, C. A., et al., (1991) Only multimers of a synthetic peptide of human apolipoprotein E are biologically active. J. Biol. Chem. 266, 15009-15015.

Dyer, C. A., et al., (1991) J. Biol. Chem. 296, 22803-22806.

Dyer, C. A., et al., (1995) Structural features of synthetic peptides of apolipoprotein E that bind the LDL receptor. J. Lipid Res. 36, 80-8.

Ehara et al. (2001) Elevated Levels of Oxidized Low Density Lipoprotein Show a Positive Relationship With the Severity of Acute Coronary Syndromes. Circulation. 103:1955-1960.

Eisenberg et al. Lipoprotein lipase enhances binding of lipoproteins to heparan sulfate on cell surfaces and extracellular matrix. J. Clin Invest. 90: 2013-2021 (1992).

Epand et al. (1987) Studies Synthetic Peptide Analog of the Amphipathic Helix J. Biol. Chem. 262(19): 9389-9396.

Epand RM, Stafford A, Leon B, Lock PE, Tytler EM, Segrest JP, Anantharamaiah GM. (1994) HDL and apolipoprotein A-I protect erythrocytes against the generation of procoagulant activity. Arterioscler Thromb. 14(11): 1775-1783.

Epand, et al. (2004) An Apolipoprotein AI Mimetic Peptide: Membrane Interactions and the Role of Cholesterol. Biochemistry. 43:5073-5083.

Epand, et al. (2004) Two Homologous Apolipoprotein AI Mimetic Peptides: Relationship Between Membrane Interactions and Biological Activity. J. of Biol. Chem. 279:51404-51415.

Farkas, M.H. et al., (2004) The recycling of apolipoprotein E and its amino-terminal 22kDA fragment: evidence for multiple redundant pathways. J. Lipid Res. 45:1546-1554.

Felgner et al. Lipofection: a highly efficient, lipid-mediated DNA-transfection procedure. PNAS, 84: 7413-7417 (1987).

Field et al. (2001) Gene expression of sterol regulatory element-binding proteins in hamster small intestine. Journal of Lipid Research. 42:1-9.

Keech, A. et al. Effects of long-term fenofibrate therapy on cardiovascular events in 9795 people with type 2 diabetes (the FIELD study): randomised controlled trial. Lancet. (2005) 366: 1849-1861.

Fielding and Fielding (1995) Molecular physiology of reverse cholesterol transport. J. Lipid Res. 36: 211-228.

Fleisher et al., Stimulation of arterial endothelial cell prostacyclin synthesis by high density lipoproteins. J Biol. Chem. 1982; 257:6653-6655.

Fogelman et al., Malondialdehyde alteration of low density lipoproteins leads to cholesteryl ester accumulation in human monocyte-macrophages. Proc Natl Acad Sci USA. 1980; 77:2214-2218.

Fogelman, A.M., When good cholesterol goes bad. Nat Med. 2004; 10:902-903.

Folch, J. et al., (1957) A simple method for isolation and purification of total lipids from animal tissues. J. Biol. Chem. 226:497-509.

(56) References Cited

OTHER PUBLICATIONS

Footer et al. (1996) Biochemical evidence that a D-Loop is part of a four-strandedPNA-DNA bundle. Nickel-mediated cleavage of duplex DNA by a Gly-Gly-His-Bis-PNA, Biochemistry. 35(33): 10673-9.
Forte et al., Altered activities of anti-atherogenic enzymes LCAT, paraoxonase, and platelet-activating factor acetylhydrolase in atherosclerosis susceptible mice. J. Lipid Res., 2002; 43:477-485.
Fritz, I.B. (1992) What is clusterin? Clin Exp Immunol. 88(3): 375.
Fukuda, et al., Bilayer forming ion-pair amphi-philes from single chain surfactants. J Am Chem Soc., 1990, 112:1635-1637.
Futterman, L.G and Lemberg, L. (2004) Statin pleiotropy: fact or fiction? Am J Crit Care. 13(3): 244-249.
Gabay C. and Kushner I., Acute-phase proteins and other systemic responses to inflammation, N. Engl. I Med. 1999; 340; 448-454.
Gambacorti-Passerini et al., In Vitro Transcription and Translation Inhibition by Anti-PromyelocyticLeukemia (PML)/Retinoic Acid Receptor α and Anti-PML Peptide Nucleic Acid. Blood. 1996; 88(4):1411-7.
Garber DW, Handattu S, Aslan I, Datta G, Chaddha M, Anantharamaiah GM. (2003) Effect of an arginine-rich amphipathic helical peptide on plasma cholesterol in dyslipidemic mice. Atherosclerosis 168(2):229-237.
Garber et al. (1992) Turnover of synthetic class A amphipathic peptide analogues of exchangeable apolipoproteins in rats. Correlation with physical properties. Arteriosclerosis and Thrombosis, 12(8): 886-894.
Garber et al. (2001) A new synthetic class a amphipathic peptide analogue protects from diet-induced atherosclerosis. Journal of Lipid Research 42:-545-552.
Garber et al. (2006) Atherosclerosis and vascular disease: effects of peptide mimetics of apolipoproteins. Curr. Pharm. Biotechnol. 7:235-240.
Garber, D.W., Kulkarni, K.R., and Anantharamaiah, G.M. A sensitive and convenient method for lipoprotein profile analysis of individual mouse plasma samples. J. Lipid Res. 41:1020-1026, (2000).
Garner et al. (1998) Oxidation of high density lipoproteins. I. Formation of methionine sulfoxide in apolipoproteins Al and AII is an early event that accompanies lipid peroxidation and can be enhanced by alpha-tocopherol. J Biol Chem. 1998; 273:6080-6087.
Garner et al. (1998) Oxidation of high density lipoproteins. II. Evidence for direct reduction of lipid hydroperoxides by methionine residues of apolipoproteins Al and AII. J Biol Chem. 1998; 273:6088-6095.
Gaut, et al. (2002) Myeloperoxidase produces nitrating oxidants in vivo. J Clin Invest 2002; 109: 1311-1319.
Geetanjali, B. et al. Changes in heat shock protein 70 localization and its content in rabbit aorta at various stages of experimental atherosclerosis Cardiovascular Pathology 11: 97-103 (2002).
Gehrs KM, Anderson DH, Johnson LV, Hageman GS. (2006) Age-related macular degeneration—emerging pathogenetic and therapeutic concepts. Ann Med. 38(7): 450-471.
George et al. (2001) 12/15-lipoxygenase gene disruption attenuates atherogenesis in LDL, receptor-deficient mice. Circulation, 2001: 104:1646-1650.
Geysen HM, Mason TJ, Rodda SJ. (1988) Cognitive features of continuous antigenic determinants. J Mol Recognit. 1(1): 32-41.
Ghersi-Egea et al. (1996) Fate of Cerebrospinal Bluid-Borne Amyloid B-Peptide: Rapid Clearance into Blood and Appreciable Accumulation by Cerebral Arteries, J. Neurochem., 67: 880-883.
Gianturco et al., Receptor-mediated uptake of hypertriglyceridemic very low density lipoproteins by normal human fibroblasts. Journal of Lipid Research. 23: 984-993 (1982).
Gianturco, S.H. et al. Apolipoprotein E mediates uptake of Sf 100-400 hypertriglyceridemic very low density lipoproteins by the low density lipoprotein receptor pathway in normal human fibroblasts. J. Biol. Chem. 258:4526-4533 (1983).
Gianturco, S.H. et al. Control of 3-hydroxy 3-methylglutaryl CoA reductase activity in cultured human fibroblasts by VLDL of subjects with hypertriglyceredemia. J. Clin. Invest. 61:320-328 (1978).
Gillote et al. (1999) Apolipoprotein-mediated plasma membrane microsolubilization. Role of lipid affinity and membrane penetration in the efflux of cellular cholesterol and phospholipid. J Biol. Chem. 274(4):2021-8.
Glomset, J.A. (1968) The Plasma lecithin: cholesterol acytransferase reaction. J. Lipid Res. 9:155-167.
Gomez-Foix, A.M. et al. Adenovirus-mediated Transfer of the Muscle Glycogen Phosphorylase Gene into Hepatocytes Confers Altered Regulation of Glycogen Metabolism. J. Biol. Chem. 267:25129-25134 (1992).
Gong et al., (1994) Structural and functional properties of human and mouse apolipoprotein A-I. Biochim. Biophys. Acta. 1213:335-342; Abstract.
Graf R, Schachman HK. (1996) Random circular permutation of genes and expressed polypeptide chains: application of the method to the catalytic chains of aspartate transcarbamoylase. Proc Natl Acad Sci U S A. 93(21): 11591-11596.
Greenway, P.J. et al. Human cytomegalovirus DNA: BumHI, EcoRI and Pst I restriction endonuclease cleavage maps Gene 18: 355-360 (1982).
Greten FR, Eckmann L, Greten TF, Park JM, Li ZW, Egan LJ, Kagnoff MF, Karin M. IKKbeta links inflammation and tumorigenesis in a mouse model of colitis-associated cancer. Cell. Aug. 6, 2004;118(3):285-96.
Griendling, K.K. et al. (2000) NAD(P)H Oxidase : Role in Cardiovascular Biology and Disease Circulation Research. 86:494-501.
Grundy S.M., et al. Implications of Recent Clinical Trials for the National Cholesterol Education Program Adult Treatment Panel III Guidelines Circulation. 110:227-239 (2004).
Gupta et al. (2004) Calculation of Creatinine Clearance Based on Unadjusted Body Weight Leads to Errors in Renal and Heart Failure Patients Circulation 110:III-243.
Gupta H, et al. (2005) Inhibition of lipopolysaccharide-induced inflammatory responses by an apolipoprotein AI mimetic peptide. Circ Res. 97(3): 236-243.
Gupta H, et al. (2005) Apolipoprotein E mimetic Peptide dramatically lowers plasma cholesterol and restores endothelial function in watanabe heritable hyperlipidemic rabbits. Circulation. 111(23): 3112-3118.
Gurfinkel et al (2002) Influenza Vaccine Pilot Study in Acute Coronary Syndromes and Planned Percutaneous Coronary Interventions. The Flu Vaccination Acute Coronary Syndromes (FLUVACS) Study. Circulation 105 :2143-2147.
Guzman, R.J. et al. Efficient Gene Transfer Into Myocardium by Direct Injection of Adenovirus Vectors Circulation Research 73:1201-1207 (1993).
Haimovici R, Gantz DL, Rumelt S, Freddo TF, Small DM. (2001) The lipid composition of drusen, Bruch's membrane, and sclera by hot stage polarizing light microscopy. Invest Ophthalmol Vis Sci. 42(7): 1592-1599.
Haj-Ahmad et al. Development of a Helper-Independent Human Adenovirus Vectorand Its Use in the Transfer of the Herpes Simplex Virus Thymidine Kinase Gene. J. Virology. 57:267-274 (1986).
Halcox, J.P. et al. (2002) Prognostic Value of Coronary Vascular Endothelial Dysfunction. Circulation. 106:653-658.
Hamase et al. (2001) Determination of Free D-ProIine and D-Leucine in the Brains of Mutant Mice Lacking D-Amino Acid Oxidase Activity. Analytical Biiochemistry. 298:253-258.
Handattu et al. (2006) Physical, Chemical, and Structural Studies of Apolipoprotein A-I Mimetics Correlate Well with the Efficacy for Inhibiting Atherosclerosis Atheroscler. Thromb. Vasc. Biol. 26(5):e64.
Handattu, S., P.,Garber, D.W., Beno, B., Bain, A.D., Mishra, V.K., Palgunachari, M.N., Datta, G., Anantharamaiah, G.M., and Epand, R.M. ApoA-I Mimetic Peptides with Differing Ability to Inhibit Atherosclerosis Also Exhibit Differences in Their Interactions with Membrane Bilayers. J. Biol. Chem. 282:1980-1988 (2007).
Handwerger, et al. (1999) Pre-β-HDL stimulates placental lactogen release from human trophoblast cells. Am. J. Physiol. 276:E384-E389.
Hanvey et al. Antisense and Antigene properties of Peptide Nucleic Acids. Science. 1992; 258(5087):1481-5.

(56) References Cited

OTHER PUBLICATIONS

Harats, et al., Overexpression of 15-lipoxygenase in vascular endothelium accelerates early atherosclerosis in LDL receptor-deficient mice. Arterioscler Thromb Vasc Biol. 2000; 20:2100-2105.
Hardy et al. (2001) An Automated High-Performance Liquid Chromatography Procedure for the Quantitation of L- and D-Amino Acids by Means of Stepwise Precolumn Derivatization Analytical Biochemistry 291:297-299.
Harkin et al. (1997) The Effects of hyper-and hypocarbia on intraparenchymal arterioles in rat brian slices, Neuroreport, 8: 1841-1844.
Hashimoto (2000) Improvement of intestinal absorption of peptides: absorption of BI-Phe monoglucosylated insulin to rat intestinal brush-border membrane vesicles. J. Pharmaceutics & Therapeutics 50(2): 197-204.
Hasty, A.H., Linton, M.R., Sanan, D., Swift, L.L., and Fazio, S. Determination of lower threshold of apolipoprotein E resulting in lipoprotein remnant clearance. J. Lipid Res. 40:1529-1538 (1999).
Hauser et al.. (1998) Identification of a Receptor Mediating Absorption of Dietary Cholesterol in the Intestine Biochemistry 178423-17850.
Havel, R. J. George Lyman Duff memorial lecture. Role of the liver in atherosclerosis. Arteriosclerosis 5: 569-580 (1985).
Hayry et al., Stabile D peptide analog of insulin-like growth factor-1 inhibits smooth muscle cell proliferation after carotid balooning injury in the rat. FASEB J. 9(13): 1336-1344, 1995.
Hein TW, Platts SH, Waitkus-Edwards KR, Kuo L, Mousa SA, Meininger GA. (2001) Integrin-binding peptides containing RGD produce coronary arteriolar dilation via cyclooxygenase activation. Am J Physiol Heart Circ Physiol. 281(6): H2378-H2384.
Henricksen et al., Enhanced macrophage degradation of low density lipoprotein prevously incubated with cultured endolelial cells; recognition by receptor for acetylated low density lipoproteins. Proc Natl Acad Sci USA., 1981; 78:6499-6503.
Hermanowski-Vosatka A, Balkovec JM, Cheng K, Chen HY, Hernandez M, Koo GC, Le Grand CB, Li Z, Metzger JM, Mundt SS, Noonan H, Nunes CN, Olson SH, Pikounis B, Ren N, Robertson N, Schaeffer JM, Shah K, Springer MS, Strack AM, Strowski M, Wu K, Wu T, Xiao J, Zhang BB, Wright SD, Thieringer R.11beta-HSD1 inhibition ameliorates metabolic syndrome and prevents progression of atherosclerosis in mice., J Exp Med. Aug. 15, 2005;202(4):517-27.
Hessler et al. (1979) LDL-induced cytotoxicity and its inhibition by 1-DL in human vascular smooth muscle and endothelial cells in culture. Atherosclerosis, 32:213, Abstract.
Hoffman et al. (1997) Isoprostanes: Free Radical-Generated Prostaglandins with constrictor Effects on cerebral Arterioles, Stroke, 28: 844-849.
Holvoet, P. et al. (1997)β-VLDL Hypercholesterolemia Relative to LDL Hypercholesterolemia Is Associated With Higher Levels of Oxidized Lipoproteins and a More Rapid Progression of Coronary Atherosclerosis in Rabbits Arterioscl. Thromb. Vasc. Biol. 17:2376-2382.
Hoogenboom et al. By-passing immunisation: Human antibodies from synthetic repertoires of germline VH gene segments rearranged in vitro J. Mol. Biol., 227:381-388, 1992.
Houstis, N., Rosen, E.D., and Lander E.S. Reactive oxygen species have a causal role in multiple forms of insulin resistance. Nature 440:944-948 (2006).
Hristova et al. (1999) An Amphipathic α-Helix at a Membrane Interface: A Structural Study using a Novel X-ray Diffraction Method. J. Mol. Biol. 290:99-117.
Huber MA, Azoitei N, Baumann B, Grünert S, Sommer A, Pehamberger H, Kraut N, Beug H, Wirth T. (2004) NF-kappaB is essential for epithelial-mesenchymal transition and metastasis in a model of breast cancer progression. J Clin Invest. 114(4): 569-581.
Hussain et al. High affinity binding between lipoprotein lipase and lipoproteins involves multiple ionic and hydrophobic interactions, does not require enzyme activity, and is modulated by glycosaminoglycans. J. Biol. Chem. 275: 29324-29330 (2000).
Hwang SJ, Ballantyne CM, Sharrett AA, Smith LC, Davis CE, Gotto AM Jr, Boerwinkle E. Circulating adhesion molecules VCAM-I, ICAM-1, and E-selectin in carotid theroscleroris and incident coronary heart disease cases. The atherosclerosis risk in communities (AMC) study. Circulation 1997;96:4219-4225.
Hyka et al. (2001) Apolipoprotein A-I Inhibits the Production of Interleukin-10 and Tumor Necrosis Factor-a by Blocking Contact-Mediated Activation of Monocytes by T Lymphocytes Blood 97:2381-2389.
Hyrup, B. and Nielsen, P.E. Peptide Nucleic Acids (PNA): Synthesis, Properties and Potential Applications Bioorg Med Chem. Jan. 1996; 4(1):5-23.
Ishigami, M., Swertfeger, D.K., Hui, M.S., Granholm, N. A. and Hui, D.Y. Apolipoprotein E inhibition of vascular smooth muscle cell proliferation but not the inhibition of migration is mediated through activation of inducible nitric oxide synthase. Arterio. Thromb. Vasc. Biol. 20:1020-1026 (2000).
Jaeger et al. Improved predictions of secondary structures for RNA Proc. Natl. Acad. Sci. USA 86:7706-7710, 1989.
Jakobovits et al. Germ-line transmission and expression of a human-derived yeast artificial chromosome. Nature, 362:255-258 (1993).
Jakobovits et al. Analysis of homozygous mutant chimeric mice: Deletion of the immunoglobulin heavy-chain joining region blocks B-cell development and antibody production Proc. Natl. Acad. Sci. USA, 90:2551-255 (1993).
Jamaluddin, et al. (1987) Aggregatory reactions of blood platelets in ustirred dilute suspensions and their monitoring by spectrophotometry. Curr Sci; 56:254-256.
Jamieson et al. (2001) Detection of Lipoprotein(a) in Intraparenchymal Cerebral Vessels: Correlation with Vascular Pathology and Clinical History, Exp. Mol Pathol., 71: 99-105.
Jensen et al. Kinetics for Hybridization of Peptide Nucleic Acids (PNA) with DNA and RNA Studied with the BIAcore Technique Biochemistry. 1997; 36(16):5072-7.
Jin et al. (2003) Inhibition of endothelial lipase causes increased ML cholesterol levels in vivo. J Clin Invest 2003; 111:357-362.
Jones. et al. Computer programs to identify and classify amphipathic of domains. J. Lipid. Res. 33: 287-296 (1992).
Jong, M.C., Dahlmans, V.E., van Gorp, P. J., Brewer, M. L. Mol, M. J., van der Ze, A., Frants, R. R., Hofker, M. H., and Havekes, L. M. Both lipolysis and hepatic uptake of VLDL are impaired in transgenic mice coexpressing human apolipoprotein E*3Leiden human apolipoprotein C-I. Arteriosc. Thromb. Vasc. Biol. 16:934-940 (1996).
Kabanov et al. A new class of antivirals: antisense oligonucleotides combined with a hydrophobic substituent effectively inhibit influenza virus reproduction and synthesis of virus-specific proteins in MDCK cells. FEBS Lett., 1990, 259, 327-330.
Kaler et al (1989) Spontaneous vesicle formation in aqueous mixtures of single-tailed surfactants, Science, 245:1371-1374.
Kandel ER, Schwartz JH, Jessell TM (Eds.) (1991) Principles of Neural Science, Third Edition. Elsevier: New York, pp. 188-189.
Karle et al. (2004) A combined extented and helical backbone for Boc-(Ala-Leu-Ac7C)2-OME, Peptides Res., 63:174-180.
Karle, et al. (1998) Crystal structure of the channel-forming polypeptide antiamoebin in a membrane-mimetic environment. Proc. Natl. Acad. Sci. 95:5501-5504.
Karle, et al. (2003) Crystal structure of hydrophobic 19-residue peptide helix containing three centrally located D amino acids, PnNAS, 100:24:13946-13951.
Kaul, S., et al. (2004) Rapid Reversal of Endothelial Dysfunction in Hypercholesterolemic Apolipoprotein E-Null Mice by Recombinant Apolipoprotein A-I$_{Milano}$-Phospholipid Complex. J. Am. Coll. Cardiol. 44:1311-1319.
Kirshenbaum, L.A. et al. Highly Efficient Gene Transfer into Adult Ventricular Myocytes by Recombinant Adenovirus. J Clin. Invest. 92:381-387 (1993).
Kissinger C, Skinner MK, Griswold MD. (1982) Analysis of Sertoli cell-secreted proteins by two-dimensional gel electrophoresis. Biol Reprod. 27(1): 233-240.
Kita, T., Brown, M.S., Watanabe, Y., and Goldstein, J.L. Deficiency of low density lipoprotein receptors in liver and adrenal gland of the

(56) References Cited

OTHER PUBLICATIONS

WHHL rabbit, an animal model of familial hypercholesterolemia. Proc Natl. Acad. Sci, USA 78: 2268-2272 (1981).
Knowler, W.C. et al. Reduction in the incidence of type 2 diabetes with lifestyle intervention or metformin. N Engl J Med. (2002) 346(6):393-403.
Ko, et al. (1993) A. Highdensity lipoprotein reduces epidermal growth factor-induced DNA synthesis in vascular smooth muscle cells. Atherosclerosis, 99: 253-259, Abstract.
Kockx, et al. (2004) Apolipoprotein A-I-stimulated Apolipoprotein E Secretion from Human Macrophages Is Independent of Cholesterol Efflux. J. Biol. Chem. 279:25966-25970.
Kolodgie, F.D., Katocs, A.S., Largis, E.E., Wrenn, S.M., Cornhill, J.F., Herdrick, E.E., Lee, S.J., and Virmani, R. Hypercholesterolemia in the rabbit induced by feeding graded amounts of low-level cholesterol. Arterioscler. Thromb. Vasc. Biol. 16:1454-1464 (1996).
Kontos, H.A. and Wei, E.P. (1998) Cerebral arteriolar dilations by KATP channelactivators need L-lysine or L-arginine Am. J. Physiol. 274 (Heart Circ. Physiol. 43): H974-H981, 1998.
Kowal, R.C., Herz, J., Goldstein, J.L., Esser, V., and Brown, M.S. Low density lipoprotein receptor related protein mediates uptake of cholesteryl ester derived from apolipoprotein E enriched lipoproteins. Proc. Natl. Acad. Sci. U.S.A. 86:5810-5814 (1989).
Kozbor D, Lagarde AE, Roder JC. (1982) Human hybridomas constructed with antigen-specific Epstein-Barr virus-transformed cell lines. Proc Natl Acad Sci USA, 79(21): 6651-55.
Kreiger (1999) Charting the Fate of the Good Cholesterol: Identifcation and Characterization of the High-Density Lipoprotein Receptor Sr—Bi. Ann Rev. Biochem. 68: 523-558.
Kullman et al. (1999) Evaluation of the Enantiomeric Composition of Amino Acids in Tobacco, Chirality, 11:669-673.
Kumar et al. (2002) A novel peptide derivative exhibits anti inflammatory and antioxidant activity in adjuvant induced arthritis in rats. Mol Cell Biochem, Jan; 229 (1-2):9-17.
Kume et al. (1992) Lysophosphatidylcholine, a component of atherogenic lipoproteins, induces mononuclear leukocyte adhesion molecules in cultured human and rabbit arterial endothelial cells. J Clin Invest. 90:1138-1144.
Kwiterovich, P.O. State-of-the-art update and review: clinical trials of lipid-lowering agents. Am. J. Cardiol. 82: 3U-17U (1998).
La Salle, G. et al, An adenovirus vector for gene transfer into neurons and glia in the brain. Science. 259:988-990 (1993).
Lalazar, A. et al. (1988) Site-specific Mutagenesis of Human Apolipoprotein E: Receptor Binding Activity of Variants With Single Amino Acid Substitutions. J. Biol. Chem. 263, 3542-2545.
Lawrence, M.B. and Springer, T.A. (1991) Leukocytes roll on a selectin at physiologic flow rates: distinction from and prerequisite for adhesion through integrins. Cell. 65:859-873.
Lee, S. et al. (2001) Vitamin C-induced decomposition of lipid hydroperoxides to endogenous genotoxins. Science. 292:2083-2086.
Legrand et al. (1992) Molecular Interactions between Human Lactotransferrin and the Phytohemagglutinin-Activated Human Lymphocyte Lactotransferrin Receptor Lie in Two Loop-Containing Regions of the N-Terminal Domain I of Human Lactotransferrin, Biochemistry, 31, 9243-9251.
Letsinger et al. Cholesteryl-conjugated oligonucleotides: Synthesis, properties, and activity as inhibitors of replication of human immunodeficiency virus in cell culture Proc. Natl. Acad. Sci. USA, 1989, 86, 6553-6556.
Levine, et al. (1993) In vivo protection against endotoxin by plasma high density lipoprotein. Proc. Natl. Acad. Sci. USA, 90:12040-12044.
Li et al. (1993) An atherogenic diet rapidly induces VCAM-1, a cytokine-regulatable mononuclear leukocyte adhesion molecule, in rabbit aortic endothelium. Arteriosclerosis and Thrombosis, 13:197-204.
Li, et al. (2004) Double Belt Structure of Discoidal High Density Lipoproteins: Molecular Basis for Size Heterogeneity. J. Mol. Biol. 343:1293-1311.

Libby et al. (2002) Inflammation and atherosclerosis. Circulation. 105:1135-1143.
Linsel-Nitschke, P. et al. HDL as a target in the treatment of atherosclerotic cardiovascular disease. Nat Rev Drug Discov. (2005) 4(3):193-205.
Mach et al. (1998) Reduction of atherosclerosis in mice by inhibition of CD40 signalling. Nature, 394:200-203.
Mahley et al. Remnant lipoprotein metabolism: key pathways involving cell-surface heparan sulfate proteoglycans and apolipoprotein E. J. Lipid Res. 40: 1-16. (1999).
Mahley et al. Pathogenesis of type III hyperlipoproteinemia (dysbetalipoproteinemia): questions, quandaries, and paradoxes. J. Lipid Res. 40: 1933-1949. (1999).
Mahley, R.W., Weisgraber, K.H., Hussain, M.M., Greenman, B., Fishe, M., Vogel, T., and Gorecki, M. Intravenous infusion of apolipoprotein E accelerates clearance of plasma lipoproteins in rabbits. J. Clin. Invest. 83: 2125-2130 (1989).
Mala, John Geraldine Sandana et al., (Aug. 2001) "Strain improvement of *Aspergillus niger* for enhanced lipase production", J Gen Appl Microbiol, 47(4):181-186.
Manikandan et al. (2002) Antioxidant potential of a novel tetrapeptide derivative in isoproterenol-induced myocardial. Pharmacology, 65:105-109.
Manoharan et al. Cholic acid-oligonucleotide conjugates for antisense applications Bioorg. Med. Chem. Let., 1994, 4, 1053-1060.
Manoharan et al. Lipidic nucleic acids. Tetrahedron Lett., 1995, 36, 3651-3654.
Marks et al. By-passing immunization. Human antibodies from V-gene libraries displayed on phage. J. Mol. Biol., 222:581, 1991.
Massie et al. Construction of a Helper-Free Recombinant Adenovirus That Expresses Polyomavirus Large T Antigen Mol. Cell. Biol. 6:2872-2883 (1986).
Mato et al. (1996) Involvement of specific macrophage-lineage cells surrounding arterioles in barrier and scavenger function in brain cortex, Proc. Natl. Acad. Sci. USA, vol. 93, pp. 3269-3274, Apr. 1996.
Mazoyer E, Levy-Toledano S, Rendu F, Hermant L, Lu H, Fiat AM, Jolles P, Caen J. KRDS, a new peptide derived from human lactotransferrin, inhibits platelet aggregation and release reaction. Eur J Biochem 1990;194:43-49.
McGarry JD.Banting lecture 2001: dysregulation of fatty acid metabolism in the etiology of type 2 diabetes.Diabetes. Jan. 2002;51(1):7-18.
Meera et al. (1999) Inhibition of neutrophil derived lysosomal enzymes and reactive oxygen species by a novel tetrapeptide. Inflamm Res. Sep. 1999, 48(9):479-84.
Mehrabian et al. (2002) Identification of 5-lipoxygenase as a major gene contributing to atherosclerosis susceptibility in mice. Circ Res. 91:120-126.
Mendez et al. (1994) Synthetic Amphipathic Helical Peptides that Mimic Apolipoprotein A-I in Clearing Cellular Cholesterol. J Clin Invest 94: 1698-1705.
Merrifield et al. (1995) Retro and Retroenantio Analogs of Cecropin-Melittin Hybrids Proc Natl Acad Sci USA 92: 3449-3453.
Mertens, A., et al. (2003) Increased Low-Density Lipoprotein Oxidation and Impaired High-Density Lipoprotein Antioxidant Defense Are Associated With Increased Macrophage Homing and Atherosclerosis in Dyslipidemic Obese Mice: LCAT Gene Transfer Decreases Atherosclerosis. Circulation. 107:1640-1646.
Miller et al. Redesign of Retrovirus Packaging Cell Lines to Avoid Recombination Leading to Helper Virus Production Mol. Cell. Biol. 6: 2895 (1986).
Mims, M. P., et al. (1994) A Nonexchangeable Apolipoprotein E Peptide That Mediates Binding to the Low Density Lipoprotein Receptor. J. Biol. Chem. 269, 20539-20647.
Mishra et al. (1994) Interaction of Synthetic Peptide Analogs of the Class A Amphipathic Helix with Lipids: Evidence for the Snorkel Hypothesis. J Biol. Chem. 269: 7185-7191.
Mishra et al. (1995) Effect of the Arrangement of Tandem Repeating Units of Class A Amphipathic a-Helixes on Lipid Interaction. J. Biol. Chem. 270: 1602-1611.

(56) References Cited

OTHER PUBLICATIONS

Mishra et al. (1996) Interaction of Model Class A1, Class A2, and Class Y Amphipathic Helical Peptides with Membranes. Biochemistry 35:11210-11220.
Mishra et al. (1998) Studies of Synthetic Peptides of Human Apolipoprotein A-I Containing Tandem Amphipathic a-Helixes Biochemistry 37: 10313-10324.
Mishra et al. (2001) Solution NMR structure of a model class A (apolipoprotein) amphipathic a helical peptide Peptides 22:567-573.
Mishra et al. (2006) Association of a model class A (apolipoprotein) amphipathic alpha helical peptide with lipid: high resolution NMR studies of peptide.lipid discoidal complexes. J. Biol. Chem. 281:6511-6519.
Miyazaki et al. (1995) Intravenous Injection of Rabbit Apolipoprotein A-I Inhibits the Progression of Atherosclerosis in Cholesterol-Fed Rabbits Arterioscler. Thromb. Vasc. Biol. 15:1882-1888.
Moore DJ, Hussain AA, Marshall J. (1995) Age-related variation in the hydraulic conductivity of Bruch's membrane. Invest Ophthalmol Vis Sci. 36(7): 1290-1297.
Morrison et al. Chimeric human antibody molecules: Mouse antigen-binding domains with human constant region domains Proc. Natl. Acad. Sci. USA, 81:6851-6855 (1984).
Morsy et al. Efficient Adenoviral-mediated Ornithine Transcarbamylase Expression in Deficient Mouse and Human Hepatocytes. J. Clin. Invest. 92:1580-1586 (1993).
Moullier et al. Correction of lysosomal storage in the liver and spleen of MPS VII mice by implantation of genetically madified skin fibroblast. Nature Genetics. 4:154-159 (1993).
Mulder et al. (2004) Low-density lipoprotein receptor-knockout mice display impaired spatial memory associated with a decreased synaptic density in the hippocampus, Neurobiology of Disease 16: 212-219.
Mulligan, R.C. The basic science of gene therapy. Science. 260:926-932 (1993).
Murugesan et al. (1994) High-density lipoprotein stimulates endothelial cell movement by a mechanism distinct from basic fibroblast growth factor. Circ. Res. 74 : 1149-1156.
Nag et al. (1997) Cerebrovascular Changes in Chronic Hypertension Protective Effects of Enalapril in Rats, Stroke, 28: 1028-1034.
Nagata et al. (1994) Distribution of free D-serine in vertebrate brains, Brain Res., 634: 291-295.
Nagata et al. (1995) Free D-serine concentration in normai and Alzheimer human brain, Brain Res. Bull., 38(2): 181-183.
Nagata et al. (2002) Hemodynamic Aspects of Alzheimer's Disease, Ann. N. Acad. Sci., 977: 391-402.
Naghavi M, Wyde P, Litovsky S, Madjid M, Akhtar A, Naguib S, Siadaty MS, Sanati S, Casscells W. (2003) Influenza infection exerts prominent inflammatory and thrombotic effects on the atherosclerotic plaques of apolipoprotein E-deficient mice. Circulation. 107(5): 762-768.
Nakamura et al. (1997) Deposition of amyloid B protein (AB) subtypes [AB40 and AB42(43)] in canine senile plaques and cerebral amyoloid angiopathy Acta Neuropathot 94: 323-328.
Nanjee et al. (1999) Acute effects of intravenous infusion of apoA-Uphosphos-phatidycholine discs on plasma lipoproteins in humans. Arterioscler Thromb Vase Biol, 19:979-989.
Nanjee et al. (2001) Intravenous apoA-1/lecithin discs increase preconcentration in tissue fluid and stimulate reverse cholesterol transport in humans. J Lipid Res, 42:1586-1593.
Navab et al. (1991) Monocyte transmigration induced by modification of low density lipoprotein in cocultures of human aortic wall cells is due to induction of monocyte chemotactic protein 1 synthesis and is abolished by high density lipoprotein. Journal of Clinical Investigation 1991;88:2039-2046.
Navab et al. (1997) Mildly oxidized LDL induces an increased apolipoprotein J/paraoxonase ratio. J Clin.Invest. 99: 2005-2019.
Navab et al. (2000) Normal high density lipoprotein inhibits three steps in the formation of midly oxidized low density lipoprotein: step 1. J Lipid Res. 41: 1481-1494.
Navab et al. (2000) Normal high density lipoprotein inhibits three steps in the formation of mildly oxidized low density lipoprotein: steps 2 and 3. J. Lipid Res. 41:1495-1508.
Navab et al. (2001) A cell-free assay for detecting HDL that is dysfunctional in preventing the formation of or inactivating oxidized phospholipids. J Lipid Res 2001; 42:1308-1317.
Navab et al. (2001) HDL and the inflammatory response induced by LDL-derived oxidized phospholipids. Arterioscler Thromb Vasc Bio. 21:481-488.
Navab et al. (2003) Oral synthetic phospholipids (DMPC) raises high-density lipoprotein cholesterol levels, improves high-density lipoprotein function, and markedly reduces atherosclerosis in apolipoprotein E-null mice. Circulation 2003; 108:1735-1739.
Navab et al. (2004) Oral D-4F causes formation of pre-high-density lipoprotein and improves high-density lipoprotein-mediated cholesterol efflux and reverse cholesterol transport from macrophages in apoE-null mice, Circulation 109:r120-r125.
Navab et al. (2004) The oxidation hypothesis of atherogenesis: the role of oxidized phospholipids and L. J. Lipid Res. 45: 993-1007.
Navab et al. (2005) The double jeopardy of HDL. Annals of Medicine 37:173-178.
Navab et al. (2005) Apolipoprotein A-I Mimetic Peptides. Arterioscler Thromb Vasc Biol 25:1325-1331.
Navab et al. (2005) D-4F and Statins Synergize to Render HDL Antiinflammatory in Mice and Monkeys and Cause Lesion Regression in Old Apolipoprotein E—Null Mice. Arterioscler Thromb Vasc Biol 25:1426-1432.
Navab et al. (2005) An oral ApoJ peptide renders HDL anti-inflammatory in Mice and Monkeys and dramatically reduces atherosclerosis in Apolipoprotein E-null mice. Arterioscler Thromb Vasc Biol 25:1932-1937.
Navab et al. (2005) The Role of High-Density Lipoprotein in Inflammation Cardiovascular Medicine 15:158-161.
Navab et al. (2005) An Apolipoprotein A-I Mimetic Works Best in the Presence of Apolipoprotein A-I Circ. Res. 25:1085-1086.
Navab et al. (2005) Oral Small Peptides render HDL antiinflammatory in mice, and monkeys and reduce atherosclerosis in ApoE null mice. Circ Res. 2005, 97:524-532.
Navab M, et al. (2002) Oral administration of an Apo A-I mimetic Peptide synthesized from D-amino acids dramatically reduces atherosclerosis in mice independent of plasma cholesterol. Circulation. 105(3): 290-292.
Navab, M., et al. (2004) Oral D-4F causes formation of pre-beta high-density lipoprotein and improves high-density lipoprotein-mediated cholesterol efflux and reverse cholesterol transport from macrophages in apolipoprotein E-null mice. Circulation 109:3215-3220.
Navab, M., et al., (2004) Apparent Paradox of Low-Fat "Healthy" Diets Increasing Plasma Levels of Oxidized Low-Density Lipoprotein and Lipoprotein(a). Arterioscler Thromb Vasc Biol 24:392-393.
Nguyen et al. (2006) Apolipoprotein A-I-mimetic peptides with antioxidant actions Arch Biochem. Biophys. 451:34-42.
Nicholls, S.J. et al. Relationship Between Atheroma Regression and Change in Lumen Size After Infusion of Apolipoprotein A-I Milano. J Am Coll Cardiol. (2006) 47(5):992-7.
Nicholls, S.J., Zeng, L., and Hazen, S.L. Formation of dysfunctional high-density lipoprotein by myeloperoxidase. Trrends Crdiovasc. Med. 15: 212-219 (2005).
Nikoulin, I.R. et al. (1998) An Apolipoprotein E Synthetic Peptide Targets to Lipoproteins in Plasma and Mediates Both Cellular Lipoprotein Interactions In Vitro and Acute Clearance of Cholesterol-rich Lipoproteins In Vivo. J. Clin Invest. 101, 223-234.
Nielsen et al., Sequence-Selective Recognition of DNA by Strand Displacement with a Thymine-Substituted Polyamide Science, 254, 1497-1500 (1991).
Nievelstein et al. (1991) Lipid accumulation in rabbit aortic intima two hours after bolus infusion of low density lipoprotein: A deep-etch and immunolocalization study of ultra-rapidly frozen tissue. Arteriosclerosis and Thrombosis, 11: 1795-1805.
Nirmala, C. and Puvanakrishnan, R. (1996) Effect of curcumin on certain lysosomal hydrolases in isoproterenol-induced myocardial infarction in rats. Biochem Pharmacol. Jan. 12, 1996;51(1):47-51.

(56) References Cited

OTHER PUBLICATIONS

Nirmala et al. (1999) Curcumin treatment modulates collagen metabolism in isoproterenol induced myocardial necrosis in rats. Mol Cell Bioche, Jul. 1999; 197 (1-2):31-37.
Nissen, S.E., et al. Effect of Recombinant ApoA-I Milano on Coronary Atherosclerosis in Patients With Acute Coronary Syndromes: A Randomized Controlled Trial. (2003) JAMA 290:2292-2300.
Nofer, J.R., van der Giet, M., Tolle, M., Wolinska, I., von Wnuck Lipinski, K., Baba, H. A., Tietge, U.J., Godecke, A., Ishii, I., Kleuser, B., Schafers, M., Fohker, M., Zidek, W., Assmann, G., Chun, J., and Levkau, B. HDL induces NO-dependent vasorelaxation via the lysophosphoreceptor S1P3. J. Clin. Invest. 113:569-581 (2004).
Nomoto et al. (1998) Improvement of Intestinal Absorption of Peptide Drugs by Glycosylation: Transport of Tetrapeptide by the Sodium Ion-Dependent D-Glucose Transporter, Jrnl of Phar, Sci, vol. 87, No. 3, Mar. 1998, pp. 326-332.
Norton et al., Targeting Peptide Nucleic Acid-Protein Conjugates to Structural Features Within Duplex DNA Bioorg Med Chem. Apr. 1995; 3(4):437-45.
Nuttall ME, Gimble JM. (2000) Is there a therapeutic opportunity to either prevent or treat osteopenic disorders by inhibiting marrow adipogenesis? Bone. 27(2): 177-184.
Oberhauser et al., Effective incorporation of 2'-O-methyl-oligoribonucleotides into liposomes and enhanced cell association through modification with thiocholesterol. Nucl. Acids Res., 1992, 20, 533-538.
O'Brien et al. (1996) Neovascular expression of E-selectin, intercellular adhesion molecule-1, and vascular cell adhesion molecule-1 in human atherosclerosis and their relation to intimal leukocyte content. Circulation 1996; 93: 672-82.
Obunike, J.C., Pillarasetti, S., Paka, L., Kako, Y., Butteri, M.J., Ho, Y-Y., Wagner, W.D., Yamada, N., Mazzone, T., Deckelbaum, R.J., and Goldberg, I. (2000) The heparin-binding proteins apolipoprotein E and lipoprotein lipase enhance cellular proteoglycan production. Arterio. Thromb. Vasc. Biol. 20:111-118 (2000).
O'Connell BJ, Genest J Jr. High-density lipoproteins and endothelial function. Circulation. 2001;104:1978-1983.
Oguchi et al. (2000) Monoclonal antibody against vascular cell adhesion molecule-1 inhibits neointimal formation after periadventitial carotid artery injury in genetically hypercholesterolemic mice. Arterioscler Thromb Vasc Biol; 20:1729-1736.
Oram and Heinecke (2005) ATP-Binding Cassette Transporter A1: A Cell Cholesterol Exporter That Protects Against Cardiovascular Disease. Physiol Rev. 85: 1343-1372.
Oram and Yokoyama (1996) Apolipoprotein mediated removal of cellular cholesterol and phospholipids. J Lipid Res. 37: 2473-2491.
Otvos, J.D. et al. Low-density lipoprotein and high-density lipoprotein particle subclasses predict coronary events and are favorably changed by gemfibrozil therapy in the Veterans Affairs High-Density Lipoprotein Intervention Trial. Circulation. (2006);113(12):1556-63.
Ou et al. (2003) AP-4F, antennapedia peptide linked to an amphipathic a helical peptide, increases the efficiency of lipofectamine-mediated gene transfection in endothelial cells. Biochem Biophys Res Commun 2003;305:605-610.
Ou et al. (2003) L-4F, an apolipoprotein A-1 mimetic, dramatically improves vasodilation in hypercholesterolemic and sickle cell disease. Circulation 2003; 107:2337-2341.
Ou et al. (2005) Effects of D-4F on Vasodilation and Vessel Wall Thickness in Hyperholesterolemic LDL Receptor—Null and LDL Receptor/Apolipoprotein A-I Double-Knockout Mice on Western Diet. Circ. Res. 97;1190-1197.
Ou et al., L-4F, an apolipoprotein A-I mimetic, restores nitric oxide and superoxide anion balance in low-density lipoprotein-treated endothelial cells. Circulation 2003; 107:1520-1524.
Owens BJ, Anantharamaiah GM, Kahlon JB, Srinivas RV, Compans RW, Segrest JP. (1990) Apolipoprotein A-I and its amphipathic helix peptide analogues inhibit human immunodeficiency virus-induced syncytium formation. J Clin Invest. 86(4): 1142-1150.

Paigen et al. (1990) Atherosclerosis Susceptibility Differences among Progenitors of Recombinant Inbred Strains of Mice. Arteriosclerosis 10: 316-323.
Paka et al. Apolipoprotein E Containing High Density Lipoprotein Stimulates Endothelial Production of Heparan Sulfate Rich in Biologically Active Heparin-like Domains J. Biol. Chem. 274: 4816-4823 (1999).
Palgunachari et al (1996) Only the Two End Xelises of Eight Tandem Amphipathic Helical Domaine of Human Apo A-I Have Significant Lipid Affinity. Arteriosclerosis, Thrombosis, & Vascular Biology 16: 328-338.
Palinski et al. (1994) ApoE-Deficient Mice Are a Model of Lipoprotein Oxidation in Atherogenesis: Demonstration of Oxidation-Specific Epitopes in Lesions and High Titers of Autoantibodies to Malondialdehyde-Lysine in Serum. Arteriosclerosis & Thrombosis. 14(4):605-616.
Pan, T.C., et al. Rabbit apolipoprotein A-I mRNA and gene: Evidence that rabbit apolipoprotein A-I is synthesized in the intestine but not in the liver. Eur. J. Biochem. 30:99-104, 1987.
Panizzutti et al. (2001) A New Strategy to Decrease N-methyl-D-aspartate (NMDA) Receptor Coactivation. Inhibition of D-serine Synthesis by Converting Serine Racemase into an Eliminase PNAS 98:5294-5299.
Papo et al. (2002) The consequence of sequence alteration of an amphipathic a-helical antimicrobial peptide and its diastereomers. J. Biol. Chem.2002;277(37): 33913-33921.
Pappenheimer et al. (1994) Intestinal Absorption and Excretion of Octapeptides Composed of D Amino Acids Proc Nail Acad Sci USA 91: 1942-1945.
Pappenheimer et al. (1997) Absorption and Excretion of Undegradable Peptides: Rols of Lipid Solubility and Net Charge. J. Pharmacology & Experimental Therapeutics 280(1):292-300.
Pardridge et al., Vector-mediated delivery of a polyamide ("peptide") nucleic acid analogue through the blood-brain barrier in vivo. Proc Natl Acad Sci USA. 1995; 92(12):5592-6.
Parhami F, Morrow AD, Balucan J, Leitinger N, Watson AD, Tintut Y, Berliner JA, Demer LL. (1997) Lipid oxidation products have opposite effects on calcifying vascular cell and bone cell differentiation. A possible explanation for the paradox of arterial calcification in osteoporotic patients. Arterioscler Thromb Vasc Biol. 17(4): 680-687.
Pasceri et al. Direct proinflammatory effect of C-reactive protein on human endothelial cells. Circulation. 2000;102:2165-2168.
Pasceri etl al. (2001) Modulation of Creactive protein-mediated monocyte chemoattractant protein-1 induction in human endothelial cells by anti-atherosclerosis drugs, Circulation. 2001;103:2531-2534.
Pasqui AL, Puccetti L, Di Renzo M, Bruni F, Camarri A, Palazzuoli A, Biagi F, Servi M, Bischeri D, Auteri A, Pastorelli M. (2005) Structural and functional abnormality of systemic microvessels in cardiac syndrome X. Nutr Metab Cardiovasc Dis. 15(1): 56-64.
Pastan et al. A retrovirus carrying an MDR1 cDNA confers multidrug resistance and polarized expression of P-glycoprotein in MDCK cells. PNAS, 85: 4486 (1988).
Patszty et al., (1994) Apolipoprotein Al Transgene Corrects Apolipoprotein E Deficiency- induced Atherosclerosis in Mice. J. Clinical Investigation 94:899-903.
Pilone (2000) D-amino acid oxidase: new findings. CMLS, Cell. Mol Life Sci, 57: 1732-1747.
Plump et al. (1994) Human apolipoprotein A-I gene expression increases high density lipoprotein and suppresses stherosclerosis in the apolipoprotein E-deficient mouse. Proc. Natl. Acad. Sci. USA 91:9607-9611.
Pohle K, Mäffert R, Ropers D, Moshage W, Stilianakis N, Daniel WG, Achenbach S. (2001) Progression of aortic valve calcification: association with coronary atherosclerosis and cardiovascular risk factors. Circulation. 104(16): 1927-1932.
Presta, Antibody engineering. Curr. Opin. Struct. Biol., 2:593-596 (1992).
Purdue News (Oct. 2000) 'Microspheres' Offer Promise for Oral Drug Delivery (3 pages).
Purdue News (Sep. 12, 1997) New Oral Insulin Delivery System Shows Promise (3 pages).

(56) References Cited

OTHER PUBLICATIONS

Quyyumi, A.A. (1998) Endothelial Function in Health and Disease: New Insights into the Genesis of Cardiovascular Disease Am. J. Med. 105:32S-39S.
Rader, D.J. (2003) Regulation of Reverse Cholesterol Transport and Clinical Implications. Am. J. Cardiology. 92:42J-49J.
Ragot, T. et al. Replication-defective recombinant adenovirus expressing the Epstein-Barr virus (EBV) envelope glycoprotein gp340]220 induces protective immunity against EBV-induced lymphomas in the cottontop tamarin. J Gen. Virology 74:501-507 (1993).
Raha et al. (1988) KRDS a tetra peptide derived from lactotransferrin inhibits binding of monoclonal antibody against glycoprotein Iib-IIIa on ADP-stimulated platelets and megakaryocytes. Blood 1988;72: 172-178.
Rajarathnam et al. 1H NMR studies of interleukin 8 analogs: characterization of the domains essential for function. Biochemistry 33: 6623-6630 (1994).
Rajashree, S. and Puvanakrishnan, R. (1999) Dexamethasone induced alterations in the levels of proteases involved in blood pressure homeostasis and blood coagulation in rats. Mol Cell Biochem. Jul. 1999;197(1-2):203-8.
Rajashree, S. and Puvanakrishnan, R. (1996) Alterations in certain lysosomal glycohydrolases and cathepsins in rats on dexamethasone administration. Mol Cell Biochem. Jan. 26, 1996;154(2):165-70.
Mol . Rajashree, S. and Puvanakrishnan, R. (1998) Dexamethasone induced alterations in enzymatic and nonenzymatic antioxidant status in heart and kidney of rats, Mol. Cell Biochem. Apr. 1998;181(1-2):77-85.
Rall, S. C., Jr., et al. (1982) Structural basis for receptor binding heterogeneity of apolipoprotein E from type III hyperlipoproteinemic subjects. PNAS USA. 79, 4696-4700.
Ram et al. In Situ Retroviral-mediated Gene Transfer for the Treatment of Brain Tumors in Rats Cancer Res. 53:83-88, (1993).
Ramesh et al. (1998) A novel surface-active peptide derivative exhibits in vitro inhibition of platelet aggregation. Peptides 1998;19:1695-1702.
Ramesh et al. (1998) Effect of a novel tetrapeptide derivative in a model of isoproterenol induced myocardial necrosis. Mol Cell Biochem. Oct. 1998;187(1-2):173-82.
Ramprasad et al. Sustained-delivery of an apolipoproteinE—peptidomimetic using multivesicular liposomes lowers serum cholesterol levels. J. Controlled Release, 79: 207-218 (2002).
Rapp, J.H., Lespine, A., Hamilton, R.L., Colyvas, N., Chaumenton, A.H., Tweedie-Hardman, J. Kotite, L., Kunitake, S.T., Havel, R.J., and Kane, J.P. Triglyceride rich lipoproteins isolated by selected affinity antiapolipoprotein B immunosorption from human atherosclerotic plaque. Athero. Thromb. 14:1767-1774 (1994).
Reape and Groot (1999) Chemokines and atherosclerosis. Atherosclerosis 1999;147:213-225.
Reddy et al. (2001) Human paraoxonase-3 is an HDLassociated enzyme with biological activity similar to paraoxonase-1 protein but is not regulated by oxidized lipids. Arterioscler Thromb Vasc Biol 2001;21:542-547.
Reddy et al. (2004) Potential role for mitogen-activated protein kinase phosphatase-1 in the development of atherosclerotic lesions in mouse models. Arterioscler Thromb Vasc Biol 2004;24:1676-1681.
Remaley et al. (2003) Synthetic amphipathic helical peptides promote lipid efflux from cells by an ABCA1-dependent and an ABCA1-independent pathway. J. Lipid. Res. 44:828-836.
Rencurel, F., Foretz, M., Kaufmann, M. R., Stroka, D., Looser, R., Leclerc, I., de Silva G., Rutter, G.A., Viollet, B., and Meyer, S.A. Stimulation of AMP-activated protein kinase is essential for the induction of drug metabolizing enzymes by Phenobarbital in human and mouse liver. Molecular Pharmacol. 70:1925-1934, (2006).
Rensen, P.C., and van Berkel, T.J. Apolipoprotein E effectively inhibits lipoprotein lipase-mediated lipolysis of chylomicron-like triglyceride-rich lipid emulsions in vitro and in vivo. J. Biol. Chem. 271:14791-14799 (1996).

Ridker, P. M. (2002) On evolutionary biology, inflammation, infection, and the causes of atherosclerosis. Circulation 2002;105:2-4.
Roessler, J. et al. Adenoviral-mediated gene transfer to rabbit synovium in vivo. Clin. Invest. 92:1085-1092 (1993).
Rogers, et al. The lipid-free structure of apolipoprotein A-I: effects of amino-terminal deletions. (1998) Biochemistry 37:11714-11725.
Roher et al. (1993) 18-Amyloid-(142) is a major component of cerebrovascular amyloid deposits: Implications for the pathology of Alzheimer disease Proc. Natl. Acad. Sci., USA, 90: 10836-10840.
Rohlmann, A., Gotthardt, M., Hammer, R.E., and Herz, J. Inducible activation of hepatic LRP gene by cell mediated recombination confirms role of LRP in clearance of chylomicron remnants. J. Clin. Invest. 101:689-695 (1998).
Roman et al. (2002) Subcortical ischaemic vascular dementia, Lancet Neurol., 1: 426-436.
Rong et al. (2001) Elevating high-density lipoprotein cholesterol in apolipoprotein E- eficient mice remodels advanced atherosclerotic lesions by decreasing macrophage and increasing smooth muscle cell content, Circulation, 2001;104:2447-2452.
Rose, D.J. Characterization of antisense binding properties of peptide nucleic acids by capillary gel electrophoresis. Anal Chem. Dec. 15, 1993; 65(24):3545-9.
Rubin et al. (1991) Inhibition of early atherogenesis in transgenic mice by human apolipoprotein AI. Nature 353:265-267.
Sabbatini et al. (2001) Microanatomical changes of intracerebral arteries in spontaneously hypertensive rats: a model of cerebrovascular disease of the elderly Mech. Aging & Dev., 122: 1257-1268.
Saison-Behmoaras et al., Short modified antisense oligonucleotides directed against Ha-ras point mutation induce selective cleavage of the mRNA and inhibit T24 cells proliferation. EMBO J., 1991, 10, 1111-1118.
Sattler W, Stocker R. Greater selective uptake by Hep G2 cells of highdensity lipoprotein cholesteryl ester hydroperoxides than of unoxidized cholesterylesters. Biochem J. 1993;294:771-778.
Schmitz-Peiffer C. Signaling aspects of insulin resistance in skeletal muscle: mechanisms induced by lipid oversupply. Cell Signal. Oct. 2000;12(9-10):583-94. Review.
Schnolzer et al. Constructing proteins by dovetailing unprotected synthetic peptides: backbone-engineered HIV protease. Science 256: 221 (1992).
Schonbeck, U. and Libby, P. (2004) Inflamation, Immunity, and HMG-CoA Reductase Inhibitors, Statins as Anti inflammatory Agents? Circulation 109(21 Suppl 1): II18-II26.
Schonfeld et al. Lipolysis produces changes in the immunoreactivity and cell reactivity of very low density lipoproteins. J. Clin. Invest. 64: 1288-1297 (1979).
Segrest et al, (1974) A Molecular Theory of Lipid-Protein Interaction in the Plasma Lipoproteins. FEBS Lett. 38: 247-253.
Segrest et al. (1992) The Amphipathic Helix in the Exchangeable Apolipoproteins: A Review of Secondary Structure and Function J Lipid Research 33:141-166.
Segrest et al. (1990) Proteins: Structure, Function and Genetics, 8: 103-117.
Segrest et al., Apolipoprotein B-100: conservation of lipid-associating amphipathic secondary structural motifs in nine species of vertebrates. J. Lipid. Res. 39:85-102 (1998).
Segrest et al., Structure of apolipoprotein B-100 in low density lipoproteins. J. Lipid. Res. 42, pp. 1346-1367 (2001).
Segrest et al. apoB-100 has a pentapartite structure composed of three amphipathic alpha-helical domains alternating with two amphipathic beta-strand domains. Detection by the computer program LOCATE. (1994) Arteriosclerosis and Thrombosis 14:1674-1685.
Senior (1999) New options developed for needle-free drug delivery. Lancet, 1998:354:1102.
Seth, et al., Role of a low-pH environment in adenovirus enhancement of the toxicity of a Pseudomonas exotoxin-epidermal growth factor conjugate. J. Virol. 51:650-655 (1984).
Seth, et al., Evidence that the Penton Base of Adenovirus Is Involved in Potentiation of Toxicity of Pseudomonas Exotoxin Conjugated to Epidermal Growth Factor. Mol. Cell. Biol. 4:1528-1533 (1984).

(56) References Cited

OTHER PUBLICATIONS

Shah et al. (1998) Effects of recombinant apolipoprotein A-I(Milano) on aortic atherosclerosis in apolipoprotein E-deficient mice. Circulation, 1998:97(8): 780-785.

Shah et al. (2001) High-dose recombinant apolipoproteins A-Imilano mobilizes tissue cholesterol and rapidly reduces plaque lipid and macrophase content in apolipoprotein Edeficient mice: potential implications ofr acute plaque stabilization. Circulation. 2001; 103:3047-3050.

Shah, P.K. et al. Apolipoprotein A-I mimetic peptides: potential role in atherosclerosis management . . . (2005) Trends Cardiovasc. Med. 15:291-296.

Shea et al., Synthesis, hybridization properties and antiviral activity of lipid-oligodeoxynucleotide conjugates. Nucl. Acids Res., 1990, 18, 3777-3783.

Shen, B.W., Scanu, A.M., and Kezdy, F.J. Structure of human serum lipoproteins inferred from compositional analysis. Proc. Natl. Acad. Sci. U.S.A. 74:837-841 (1977).

Shih et al. (1999) Minimally modified low-density lipoprotein induces monocyte adhesion to endothelial connecting segment-1 by activating beta integrin. J Clin Invest 1999; 103:613-625.

Shih et al. (2000) Combined serum paraoxonase/apolipoprotein E knockout mice exhibit increased lipoprotein oxidation and atherosclerosis. I Biol. Chem., 2000; 275:17527-17535.

Shimono, H. N., et al., Plasma lipoprotein metabolism in transgenic mice overexpressing apolipoprotein E. Accelerated clearance of lipoproteins containing apolipoprotein B. (1992) Eur. J. Clin. Invest. 90, 2084-2991.

Shishehbor et al. (2003) Association of nitrotyrosine levels with cardiovascular disease and modulation by statin therapy. JA 2003:289:1675-1680.

Silkensen et al., Identification of clusterin sequences mediating renal tubular cell interactions; J Peptide Res., 1999,54:449-547.

Singh et al. (2000) Innate defences against viremia, Rev Med Virol 2000, 10:395-403.

Sonntag et al. (1997) Decreases in Cerebral Microvasculature with Age Are Associated with the Decline in Growth Hormone and insulin-Like Growth Factorl, Endocrinol 138(8): 3515-3520.

Sorescu et al. NAD(P)H oxidases and their relevance to atherosclerosis. Trends Cardiovas Med 2001;11:124-131.

Sparrow, C.P., Bafflc, J., Lam, M.H., Lund, E.G., Adams, A.D., Fu, X, Haynes, N., Jones, A.B., Macnaul, K.L., Ordeyka, J., Singh, S., Wang, J., Zhou, G., Moller, D.E., Wright, S.D., and Menke, J.G. A potent synthetic LXR agonist is more effective than cholesterol loading at inducing ABC A1-mRNA and stimulating cholesterol efflux. J. Biol. Chem. 277:10021-10027 (2002).

Spieker et al. (2002) High-density lipoprotein restores endothelial function in hypercholesterolemic men. Circulation. 2002;105:1399-1402.

Sprecher et al. (1993) The Low HDL Cholesterol/ High Triglyceride Trait Arterioscler. Thromb. 13: 495-504.

Springer, T.A. (1990) Adhesion receptors of the immune system. Nature 1990; 346:425-434.

Srinivas et al. (1990) Antivrial Effects of Apolipoprotein A-I and Its Synthetic Amphipathic Peptide Analogs. Virology. 176:48-57.

Stannard et al. (2001) Inability of plasma high-density lipoproteins to inhibit cell adhesion molecule expression in human coronary artery endothelial cells. Atherosclerosis. 2001;154:31-38.

Steplewski et al. Isolation and characterization of anti-monosialoganglioside monoclonal antibody 19-9 class-switch variants. PNAS 82: 8653 (1985).

Sugatani et al. (1996) High-density lipoprotein inhibits the synthesis of platelet-activating factor in human vascular endothelial cells. J Lipid Mediators Cell Signal. 1996:13:73-88.

Sumitra et al. (2001) Experimental myocardial necrosis in rats: role of arjunolic acid on platelet aggregation, coagulation and antioxidant status. Mol Cell Biochem. 2001; 224(1-2).

Suresh, R. et al. (1992) Alterations in human gingival glycosaminoglycan pattern in inflammation and in phenytoin induced overgrowth. Mol Cell Biochem. Oct. 7, 1992; 115(2):149-54.

Svensson, U. Role of vesicles during adenovirus 2 internalization into HeLa cells. J. Virology 55:442-449 (1985).

Swain, J. et al. Prooxidant iron and copper, with ferroxidase and xanthine oxidase activities in human atherosclerotic material. (1995) FEBS Lett. 368(3):513-515.

Swarnakar et al. The apolipoprotein E-dependent low density lipoprotein cholesteryl ester selective uptake pathway in murine adrenocortical cells involves chondroitin sulfate proteoglycans and an alpha 2-macroglobulin receptor. J. Biol. Chem. 276: 21121-21126 (2001).

Swift, L.L. et al., A recycling pathway for resecretion of internalized apolipoprotein E in liver cells. (2001) J. Biol. Chem. 276:22965-22970.

Takahashi, S.Y., Kawarabayasi, T., Nakai, J., Sakai, and Yamamoto, T. Rabbit very low density lipoprotein receptor-a low density receptor like protein with distinct ligand specificity. Proc. Natl. Acad. Sci. U.S.A. 89: 9252-9256 (1992).

Tan et al. (1997) A Novel, highly Efficient Peptide-HLA Class TH:ca Binding Assay using unfolded heavy change molecules: Identification of HIV-1 Derived Peptides that Bind to FILA-A* 0201 and HLA-A* 0301, J Immunol Methods, 205:201-209.

Thomas, Eric C. (1999) Brain macrophages: on the role of pericytes and perivascular cells, Brain Res. Rev., 31: 42-57.

Throngate, F.E. et al., Low levels of extrahepatic nonmacrophage ApoE inhibit atherosclerosis without correcting hypercholesterolemia in ApoE-deficient mice. (2000) Arterio. Thromb. Vasc. Biol. 20:1939-1945.

Tian et al. (2002) Structure-affinity relationships in the gp41 ELDKWA epitope for the HIV-1 neutralizing monoclonal antibody 2F5: effects of side-chain and backbone modifications and conformational constraints, J. Peptide Res. 59, 2002, 264-276.

Toyoda, Kazunori et al (1997) Effect of Aging on Regulation of Brain Stem Circulation During hypotension, J. Cerebral Blood Flow & Metab., 17(6): 680-685.

Triaggiai et al., An efficient method to make human monoclonal antibodies from memory B cells: potent neutralization of SARS coronavirus, Nat Med. Aug. 2004;10(8):871-5 (2004).

Tsai et al. (1998) D-serine added to antipsychotics for the treatment of schizophrenia. Biol. Psychiatry, 44: 1081-1089.

Tsao et al. (2001) Hibernation-induction Peptide and Cell Death: [D-Ala2, D-Leulenkephalin Blocks Bax-related Apoptotic Processes. European Journal of Pharmacology 428:149-151.

Tsimikas et al. (2001) Measuring Circulating Oxidized Low-Density Lipoprotein to Evaluate Coronary Risk. Circulation 103:1930-1932.

Tward et al. (2002) Decreased atherosclerotic lesion formation in human serum paraoxonase transgenic mice, Circulation 2002;106:484-490.

Tytler et al. Reciprocal effects of apolipoprotein and lytic peptide analogs on membranes. Cross-sectional molecular shapes of amphipathic alpha helixes control membrane stability. J. Biol. Chem. 268: 2212-2218 (1993).

Valabhji, J., et al., (2001) High-density lipoprotein composition and paraoxonase activity in Type I diabetes. Clinical Science. 101:659-670.

Van Leeuwen R, Klaver CC, Vingerling JR, Hofman A, de Jong PT. (2003) Epidemiology of age-related maculopathy: a review. Eur J Epidemiol. (9): 845-854.

Van Lenten et al. (2002) Influenza infection promotes macrophage traffic into arteries of mice that is prevented by D-4F, an apolipoprotein A-I mimetic peptide. Cir 2002, 106:1127-1132.

Van Lenten, BJ. et al. (2001) High-density lipoprotein loses its anti-inflammatory properties during acute influenza A infection, Circulation 2001; 103:2283-2288.

Van Lenten, et al. (1995) Anti-inflammatory HDL Becomes Pro-inflammatory during the Acute Phase Response, J. Clin. Invest., vol. 96, Dec. 1995, 2758-2767.

Van Lenton et al. (2004). D-4F an ApoA-I mimetic peptide inhibits the inflammatory response induced by influenza A infection of human type II pneumocytes, Circulation: 110:3252-3258.

(56) References Cited

OTHER PUBLICATIONS

Varga et al., Infectious entry pathway of adenovirus type 2. J. Virology 65:6061-6070 (1991).
Venugopal et al. (2002) Demonstration that C-reactive protein decreases eNOS expression and bioactivity in human aortic endothelial cells. Circulation. 2002; 106:1439-41.
Verhoeyen et al., Reshaping human antibodies: grafting an antilysozyme activity. Science, 239:1534-1536 (1988).
Vinters et al. (1998) Secondary microvascular degeneration in amyloid angiopathy of patients with hereditary cerebral hemorrhage with amyloidosis, Dutch type (HCHWA-D), Acta Neuropathol. 95: 235-244.
Vovenko, Eugene (1999) Distribution of oxygen tension on the surface of arterioles, capillaries and venules of brain cortex and in tissue in normoxia; an experimental study on rats. Eur. J. Physiol., 437: 617-623.
Wake AK, Datta G, Palgunachari MN, Mishra VK, Anatharamaiah GM, White RG. Apolipoprotein A-1 mimetic peptide retains function after oxidant exposure. Proc ASME 2008 Summer Bioenginerring Conference (Marco Island, Florida), Jun. 25-29, 2008, SBC2008-189660.
Walpola et al. (1995) Expression of ICAM-1 and VCAM-1 and monocyte adherence in arteries exposed to altered shear stress. Arterioscler Thromb Vasc Biol, 15:2-10.
Watson et al. (1995) Effect of platelet activating factor-acetylhydrolase on the formation and action of minimally oxidized-low gensitylipoprotein. J Clin Invest. 1995; 95:774-782.
Watson et al. (1995) Protective effect of high density lipoprotein associated paraoxonase Inhibition of the biological activity of minimally oxidized low density lipoprotein. J Clin Invest 1995;96:2882-2891.
Watts et al. Dyslipoproteinaemia and hyperoxidative stress in the pathogenesis of endothelial dysfunction in non-insulin dependent diabetes mellitus: an hypothesis. Atherosclerosis 141: 17-30 (1998).
Weers PM, Narayanaswami V, Ryan RO. (2001) Modulation of the lipid binding properties of the N-terminal domain of human apolipoprotein E3. Eur J Biochem. 268(13): 3728-3735.
Wei et al. (1998) Antioxidants Inhibit ATP-Sensitive Potassium Channels in Cerebral Arterioles, Stroke, 29: 817-823.
White, C. R., et al., Superoxide and peroxynitrite in atherosclerosis. (1994) Proc. Natl. Acad. Sci. USA. 91:1044-1048.
White, C.R., et al., Circulating plasma xanthine oxidase contributes to vascular dysfunction in hypercholesterolemic rabbits. (1996) Proc. Natl. Acad. Sci. (USA) 93: 8745-8749.
Wickham et al., Integrins alpha v beta 3 and alpha v beta 5 promote adenovirus internalization but not virus attachment. Cell 73:309-319 (1993).
Wilson et al. Three-dimensional structure of the LDL receptor-binding domain of human apolipoprotein E. Science 252: 1817-1822 (1991).
Witztum, J.L. et al. Role of oxidized low density lipoprotein in atherogenesis. J. Clin Invest. 88:1785-1792 (1991).
Wolff JA, Malone RW, Williams P, Chong W, Acsadi G, Jani A, Felgner PL. (1990) Direct gene transfer into mouse muscle in vivo. Science, 247(4949 Pt 1): 1465-8.
Wool GD, Reardon CA, Getz GS. (2008) Apolipoprotein A-I mimetic peptide helix number and helix linker influence potentially anti-atherogenic properties. J Lipid Res. 49(6): 1268-1283.
Wool GD, Vaisar T, Reardon CA, Getz GS. (2009) An apoA-I mimetic peptide containing a proline residue has greater in vivo HDL binding and anti-inflammatory ability than the 4F peptide. J Lipid Res. 50(9): 1889-1900.
Wu, G., Yuan, J., and Hunninghake, D.B. Effect of human apolipoprotein E isoforms on plasma lipids, lipoproteins and apolipoproteins in apolipoprotein E deficient mice. Atherosclerosis. 141:287-296 (1998).
Xia et al. (1999) High density lipoproteins (HDL) interrupt the sphingosine kinase signaling pathway. A possible mechanism for protection against atherosclerosis by HDL. JBiol Chem. 1999; 274:33143-33147.
Yamada, et al., Increased clearance of plasma cholesterol after injection of apolipoprotein E into Watanabe heritable hyperlipidemic rabbits. (1989) Proc. Natl. Acad. Sci. U.S.A. 86, 665-669.
Yamashita et al. (2000) Molecular mechanisms, lipoprotein abnormalities and atherogenicity of hyperalphalipoproteinemia. Atherosclerosis. 152:271-285.
Yan et al. (2004) PLTP deficiency improves the anti-inflammatory properties of HDL and reduces the ability of LDL to induce monocyte chemotactic activity. J Lipid Res 2004; 45:1852-1858.
Yancey et al. (1995) Efflux of Cellular Cholesterol and Phospholipid to Lipid-free Apolipoproteins and Class A Amphipathic Peptides. Biochemistry, 34: 7955-7965.
Yip KP, Marsh DJ. (1997) An Arg-Gly-Asp peptide stimulates constriction in rat afferent arteriole. Am J Physiol. 273(5 Pt 2): F768-F776.
Yla-Herttuala, S. et al. Macrophages and smooth muscle cells express lipoprotein lipase in human and rabbit atherosclerotic lesions. (1991) Proc. Natl. Acad. Sci. U.S.A. 88:10143-10147.
Yokoyama, et al. The mechanism of activation of lecithin:cholesterol acyltransferase by apolipoprotein A-I and an amphiphilic peptide. J. Biol. Chem. 255:7333-7339, 1980.
Yu et al. Tissue Doppler imaging is superior to strain rate imaging and postsystolic shortening on the prediction of reverse remodeling in both ischemic and nonischemic heart failure after cardiac resynchronization therapy. (2004) Circulation 110:III-243.
Yuan and Altman, Substrate recognition by human RNase P: identification of small, model substrates for the enzyme. EMBO J 14:159-168 (1995).
Yuan et al., Targeted cleavage of mRNA by human RNase P. Proc. Natl. Acad. Sci. USA 89:8006-8010 (1992).
Yui et al. (1988) Serum prostacyclin stabilizing factor is identical to apolipoprotein A-I (Apo A-I). A novel function of Apo A-1, J. Clin. Invest. 1988; 82: 803-807.
Zabner et al., Adenovirus-mediated gene transfer transiently corrects the chloride transport defect in nasal epithelia of patients with cystic fibrosis. Cell 75:207-216 (1993).
Zabner et al., Safety and efficacy of repetitive adenovirus-mediated transfer of CFTR cDNA to airway epithelia of primates and cotton rats. Nature Genetics 6:75-83 (1994).
Zaiou et al., Apolipoprotein E;-low density lipoprotein receptor interaction. Influences of basic residue and amphipathic alpha-helix organization in the ligand. Journal of Lipid Research 41: 1087-1095 (2000).
Zeiher at al. (1994) Coronary atherosclerotic wall thickening and vascular reactivity in humans. Elevated high-density lipoprotein levels ameliorate abnormal vasoconstriction in early atherosclerosis. Circulation 1994;89;2525-2532.
Zhang Z, et al. (2007) D-4F, An Apolipoprotein A-I Mimetic Peptide, Prevents Endothelial Dysfunction Induced by Myeloperoxidase-Derived Hypochlorous Acid. Meeting Abstract 21: 706.11, FASEB J.
Zhang, C., et al. L-arginine chlorination products inhibit endothelial nitric oxide production. J. Biol. Chem. 276: 27159-27165 (2001).
Zhang, Renliang et al (2002) Myeloperoxidase functions as a major enzymatic catalyst for initiation of lipid peroxidation at sites of inflammation. J Biol Chem 2002;277:46116-46122.
Zhang, S. H., et al., Spontaneous hypercholesterolemia and arterial lesions in mice lacking apolipoprotein E. Science, 1992, 258, 468-471.
Zhang, Wei-Jian et al. (2002) Lack of inhibitory effect of HDL on TNFalpha-induced adhesion molecule expression in human aortic endothelial cells. Atherosclerosis 2002; 165:241-249.
Zhao et al. (2002) Selective interleukin-12 synthesis defect in 12/15-lipoxygenase deficient macrophages associated with reduced atherosclerosis in a mouse model of familial hxjpercholesterolemia. J Biol Chem 2002 ; 277:35350-35356.
Zhu, B., Kubel, D.G., Witte, D.P., and Hui, D.Y. Apolipoprotein E inhibits neointimal hyperplasia after arterial injury in mice. Am. J. Pathol. 157:1839-48 (2000).
Zhu, Y., and Hui, D.Y. Apolipoprotein E binding to low density lipoprotein receptor related protein-1 inhibits cell migration via activation of cAMP dependent protein kinase A. J. Biol. Chem. 278:36257-63 (2003).

(56) References Cited

OTHER PUBLICATIONS

Zilversmit, D.E. (1979) Atherogenesis: a postprandial phenomenon . . . Circulation 60:473-485.
Zuker, M. On finding all suboptimal foldings of an RNA molecule. Science 244:48-52, 1989.
Restriction Requirement issued Sep. 12, 2002 for U.S. Appl. No. 09/645,454.
Response to Restriction Requirement filed Dec. 12, 2002 for U.S. Appl. No. 09/645,454.
Non-Final Office Action issued Jan. 22, 2003 for U.S. Appl. No. 09/645,454.
Response to Non-Final Office Action filed May 27, 2003 for U.S. Appl. No. 09/645,454.
Notice of Allowance issued Jun. 25, 2003 for U.S. Appl. No. 09/645,454.
Restriction Requirement issued Feb. 20, 2003 for U.S. Appl. No. 09/896,841.
Response to Restriction Requirement filed Aug. 25, 2003 for U.S. Appl. No. 09/896,841.
Non-Final Office Action issued Oct. 21, 2003 for U.S. Appl. No. 09/896,841.
Response to Non-Final Office Action filed Apr. 23, 2004 for U.S. Appl. No. 09/896,841.
Final Office Action issued May 7, 2004 for U.S. Appl. No. 09/896,841.
RCE/Response to Final Office Action filed Nov. 15, 2004 for U.S. Appl. No. 09/896,841.
Notice of Allowance issued Dec. 20, 2004 for U.S. Appl. No. 09/896,841.
International Search Report issued May 17, 2002 for PCT App. No. PCT/US01/26457.
International Preliminary Examination Report issued Mar. 4, 2003 for PCT App. No. PCT/US01/26457.
Restriction Requirement issued Jul. 15, 2003 for U.S. Appl. No. 10/187,215.
Response to Restriction Reqirement filed Nov. 19, 2003 for U.S. Appl. No. 10/187,215.
Non-Final Office Action issued Jan. 8, 2004 for U.S. Appl. No. 10/187,215.
Response to Non-Final Office Action filed Jul. 12, 2004 for U.S. Appl. No. 10/187,215.
Non-Final Office Action issued Aug. 26, 2004 for U.S. Appl. No. 10/187,215.
Response to Non-Final Office Action filed Feb. 28, 2005 for U.S. Appl. No. 10/187,215.
Final Office Action issued Apr. 11, 2005 for U.S. Appl. No. 10/187,215.
RCE/Response to Final Office Action filed Oct. 7, 2005 for U.S. Appl. No. 10/187,215.
Non-Final Office Action issued Oct. 28, 2005 for U.S. Appl. No. 10/187,215.
Response to Non-Final Office Action filed Mar. 20, 2006 for U.S. Appl. No. 10/187,215.
Notice of Allowance issued May 1, 2006 for U.S. Appl. No. 10/187,215.
Restriction Requirement issued Feb. 19, 2004 for U.S. Appl. No. 10/273,386.
Response to Restriction Requirement filed May 3, 2004 for U.S. Appl. No. 10/273,386.
Non-Final Office Action issued Jun. 21, 2004 for U.S. Appl. No. 10/273,386.
Response to Non-Final Office Action filed Dec. 21, 2004 for U.S. Appl. No. 10/273,386.
Final Office Action issued Feb. 2, 2005 for U.S. Appl. No. 10/273,386.
RCE/Response to Final Office Action filed Aug. 15, 2005 for U.S. Appl. No. 10/273,386.
Non-Final Office Action issued Sep. 7, 2005 for U.S. Appl. No. 10/273,386.
Response to Non-Final Office Action filed Jan. 20, 2006 for U.S. Appl. No. 10/273,386.
Final Office Action issued Mar. 31,2006 for U.S. Appl. No. 10/273,386.
Response to Final Office Action filed Jul. 3, 2006 for U.S. Appl. No. 10/273,386.
Notice of Allowance issued Aug. 20, 2006 for U.S. Appl. No. 10/273,386.
Restriction Requirement issued Nov. 9, 2004 for U.S. Appl. No. 10/423,830.
Response to Restriction Requirement filed Mar. 1, 2005 for U.S. Appl. No. 10/423,830.
Non-Final Office Action issued Apr. 18, 2005 for U.S. Appl. No. 10/423,830.
Response to Non-Final Office Action filed Oct. 19, 2005 for U.S. Appl. No. 10/423,830.
Final Office Action issued Nov. 15, 2005 for U.S. Appl. No. 10/423,830.
RCE/Response to Final Office Action filed Oct. 18, 2006 for U.S. Appl. No. 10/423,830.
Notice of Allowance issued Nov. 21, 2006 for U.S. Appl. No. 10/423,830.
Restriction Requirement issued Aug. 21, 2007 for U.S. Appl. No. 11/407,390.
Response to Restriction Requirement filed Nov. 23, 2007 for U.S. Appl. No. 11/407,390.
Non-Final Office Action issued Jan. 17, 2008 for U.S. Appl. No. 11/407,390.
Response to Non-Final Office Action filed Jul. 17, 2008 for U.S. Appl. No. 11/407,390.
Final Office Action issued Sep. 11, 2008 for U.S. Appl. No. 11/407,390.
RCE/Response to Final Office Action filed Jul. 13, 2009 for U.S. Appl. No. 11/407,390.
Ex Parte Quayle Action issued Aug. 14, 2009 for U.S. Appl. No. 11/407,390.
Response to Ex Parte Quayle Action filed Oct. 14, 2009 for U.S. Appl. No. 11/407,390.
Notice of Allowance issued Dec. 2, 2009 for U.S. Appl. No. 11/407,390.
Restriction Requirement issued Aug. 12, 2010 for U.S. Appl. No. 12/027,728.
Response to Restriction Requirement filed Sep. 27, 2010 for U.S. Appl. No. 12/027,728.
Non-Final Rejection issued May 27, 2011 for U.S. Appl. No. 12/027,728.
Response to Non-Final Rejection filed Nov. 1, 2011 for U.S. Appl. No. 12/027,728.
International Search Report and Written Opinion issued Sep. 1, 2009 for PCT App. No. PCT/US2009/033415.
International Preliminary Opinion on Patentability issued Aug. 19, 2010 for PCT App. No. PCT/US2009/033415.
Preliminary Amendment filed Nov. 13, 2003 for U.S. Appl. No. 10/712,447.
Preliminary Amendment filed May 14, 2014 for U.S. Appl. No. 10/712,447.
Restriction Requirement issued Oct. 14, 2005 for U.S. Appl. No. 10/712,447.
Restriction Requirement issued Feb. 16, 2006 for U.S. Appl. No. 10/712,447.
Response to Restriction Requirement filed Mar. 16, 2006 for U.S. Appl. No. 10/712,447.
Non-Final Office Action issued May 31, 2006 for U.S. Appl. No. 10/712,447.
Response to Non-Final Office Action filed Nov. 29, 2006 for U.S. Appl. No. 10/712,447.
Final Office Action issued Mar. 2, 2007 for U.S. Appl. No. 10/712,447.
Response to Final Office Action filed Jul. 31, 2007 for U.S. Appl. No. 10/712,447.
Advisory Action issued Aug. 13, 2007 for U.S. Appl. No. 10/712,447.
Response to Advisory Action and Final Office Action filed Sep. 4, 2007 for U.S. Appl. No. 10/712,447.

(56) References Cited

OTHER PUBLICATIONS

Non-Final Office Action issued Nov. 19, 2007 for U.S. Appl. No. 10/712,447.
Response after Non-Final Office Action filed Mar. 12, 2008 for U.S. Appl. No. 10/712,447.
Non-Final Office Action issued Jun. 13, 2008 for U.S. Appl. No. 10/712,447.
Response to Non-Final Office Action filed Sep. 3, 2008 for U.S. Appl. No. 10/712,447.
Terminal Disclaimer filed Sep. 3, 2008 for U.S. Appl. No. 10/712,447.
Terminal Disclaimer accepted Feb. 12, 2009 for U.S. Appl. No. 10/712,447.
Notice of Allowance with Interview Summary and Examiner's Amendment issued Feb. 24, 2009 for U.S. Appl. No. 10/712,447.
Issue Notification issued Jul. 1, 2009 for U.S. Appl. No. 10/712,447.
Request for Certificate of Correction filed Aug. 3, 2009 for U.S. Appl. No. 10/712,447.
Certificate of Correction issued Sep. 8, 2009 for U.S. Appl. No. 10/712,447.
Restriction Requirement issued Jun. 26, 2008 for U.S. Appl. No. 11/405,601.
Response to Restriction Requirement filed Jul. 25, 2008 for U.S. Appl. No. 11/405,601.
Miscellaneous Action issued Oct. 24, 2008 for U.S. Appl. No. 11/405,601.
Response to Restriction Requirement filed Mar. 17, 2009 for U.S. Appl. No. 11/405,601.
Non-Final Office Action issued Jun. 10, 2009 for U.S. Appl. No. 11/405,601.
Response to Non-Final Rejection filed Oct. 9, 2009 for U.S. Appl. No. 11/405,601.
Final Office Action issued Jan. 29, 2010 for U.S. Appl. No. 11/405,601.
Response to Final Office Action filed Sep. 28, 2010 for U.S. Appl. No. 11/405,601.
Notice of Allowance issued Sep. 9, 2011 for U.S. Appl. No. 11/405,601.
International Search Report issued Nov. 17, 2005 for PCT Application No. PCT/US2003/036268.
Examiner's First Report issued Apr. 30, 2008 for Australian Application No. 200390825.
First Statement of Proposed Amendments filed Sep. 18, 2008 for Australian Application No. 200390825.
Notice of Acceptance issued Oct. 14, 2008 for Australian Application No. 200390825.
Grant of Request for Leave to Amend issued Jul. 3, 2009 for Australian Application No. 200390825.
First Examination Report issued Sep. 18, 2007 for New Zealand Application No. 541504.
Response to Examination Report filed Jul. 16, 2008 for New Zealand Application No. 541504.
Examination Report issued for Aug. 5, 2008 New Zealand Application No. 541504.
Response to Examination Report filed Dec. 23, 2008 for New Zealand Application No. 541504.
Examination Report issued Jan. 22, 2009 for New Zealand Application No. 541504.
Response to Examination Report filed Mar. 18, 2009 for New Zealand Application No. 541504.
Examination Report and Notice of Acceptance of Completed Specification issued Apr. 7, 2009 for New Zealand Application No. 541504.
Letters Patent issued Aug. 13, 2009 for New Zealand Application No. 541504.
Office Action issued Aug. 10, 2009 for Canadian Application No. 2,514,303.
Response to Office Action filed Feb. 10, 2010 for Canadian Application No. 2,514,303.
Office Action issued Oct. 6, 2010 for Canadian Application No. 2,514,303.
Response to Office Action filed Mar. 29, 2011 for Canadian Application No. 2,514,303.
Preliminary Amendment filed Mar. 16, 2010 for U.S. Appl. No. 12/675,073.
Arisaph Pharmaceuticals Reports on Promising Results Presented at American Heart Association: Novel Apo A-I-Mimetic Peptide Significantly Inhibits Atherosclerosis in Preclinical Animal Study, BioSpace News, (Nov. 14, 2005) (3 pages). http://www.biospace.com/News/arisaph-pharmaceuticals-reports-on-promising/2610.
Chiesa, G. et al., Recombinant Apolipoprotein A-IMilano Infusion into Rabbit Carotid Artery Rapidly Removes Lipid from Fatty Streaks, Circ Res, 90: 974-80 (2002).
Garber, D.W. et al., An Arginine-Rich Amphipathic Helical Peptide Mediates Rapid Clearance of Plasma Cholesterol in Dyslipidemic Mice, Arterio Thromb Vasc Biol, 21:650.
Houstis, N. et al., Reactive Oxygen Species Have a Causal Role in Multiple Forms of Insulin Resistance, Nature, 440: 944-8 (2006) (abstract only).
Kidson, W. et al., Treatment of Severe Diabetes Mellitus by Insulin Infusion, Br Med J, 2(5921): 691-4 (1974).
Manchekart, M. et al., Apolipoprotein B-Containing Lipoprotein Particle Assembly: Lipid Capacity of the Nascent Lipoprotein Particle, J Biol Chem, 279(38): 39757-66 (2004).
Ranganathan, D. et al., Channel-Forming Self-Assembling, Bishelical Amphiphilic Peptides: Design, Synthesis and Crystal Structure of Py (Aibn)2, n=2, 3, 4, J Peptide Res, 56(6): 416-26 (2000).
Certificate of Grant issued on Dec. 11, 2014 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation (97 pages).
Examination Report No. 2 issued on Jan. 6, 2014 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation; (4 pages).
Examination Report No. 1 issued on Nov. 9, 2012 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation; (3 pages).
Office Action issued on Feb. 3, 2015 by the Canadian Intellectual Property Office for Canadian Patent Application No. 2,704,729, which was filed on Aug. 27, 2008 (Inventor—Anantharamaiah et al.; Applicant—UAB Research Foundation; (4 pages).
Tam, et al., "Interaction of a recombinant form of apolipoprotein[a] with human fibroblasts and with the human hepatoma cell line HepG2", J Lipid Res Mar. 1997 vol. 37, No. 3, pp. 518-533.
International Search Report and Written Opinion issued on Dec. 15, 2015 for application PCT/US2015/041162, filed on Jul. 20, 2015 (Applicant—UAB Research Foundation//Inventor—Anantharamaiah, et al.) (12 pages).
U.S. Appl. No. 08/924,280, filed Sep. 5, 1997, Anantharamaiah et al.
U.S. Appl. No. 10/712 447, filed Nov. 13, 2003, Anantharamaiah et al.
U.S. Appl. No. 11/405,601, filed Apr. 17, 2006, Anantharamaiah et al.
U.S. Appl. No. 13/338,125, filed Dec. 27, 2011, Anantharamaiah et al.
U.S. Appl. No. 09/520,698, filed Mar. 7, 2000, Anantharamaiah.
U.S. Appl. No. 12/675,073, filed Aug. 27, 2008, Anantharamaiah et al.
U.S. Appl. No. 13/429,022, filed Mar. 23, 2012, Anantharamaiah et al.
U.S. Appl. No. 12/027,728, filed Feb. 7, 2008, Anantharamaiah et al.
U.S. Appl. No. 12/865,957, filed Feb. 6, 2009, Anantharamaiah et al.
U.S. Appl. No. 13/804,161, filed Mar. 14, 2013, Anantharamaiah et al.
Application No. 2010-523116, Aug. 27, 2008, Anantharamaiah et al.
Application No. PCT/US2008/074485, Aug. 27, 2008, Anantharamaiah et al.
Application No. 2008296478, Aug. 27, 2008, Anantharamaiah et al.

(56) References Cited

OTHER PUBLICATIONS

Application No. 2704729, Aug. 27, 2008, Anantharamaiah et al.
Application No. 08798802.8, Aug. 27, 2008, Anantharamaiah et al.
Application No. 13187186.5, Oct. 7, 2013, Anantharamaiah et al.
Application No. 2010-523114, Aug. 27, 2008, Anantharamaiah et al.
Application No. PCT/US2008/074470, Aug. 27, 2008, Anantharamaiah et al.
Application No. 2714082, Feb. 6, 2009, Anantharamaiah et al.
Application No. PCT/US2009/033415, Feb. 6, 2009, Anantharamaiah et al.

* cited by examiner

SEQUENCE LISTING

```
<160> NUMBER OF SEQ ID NOS: 104

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1

Leu Arg Lys Leu Arg Lys Arg Leu Leu Arg
```

```
<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 2

Leu Arg Lys Met Arg Lys Arg Leu Met Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 3

Leu Arg Arg Leu Arg Arg Arg Leu Leu Arg
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 4

Asp Trp Leu Lys Ala Phe Tyr Asp Lys Val Ala Glu Lys Leu Lys Gly
1               5                   10                  15

Ala Phe

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 5

Leu Arg Lys Leu Arg Lys Arg Leu Leu Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 6

Leu Arg Lys Leu Arg Lys Arg Leu Leu Arg
1               5                   10

<210> SEQ ID NO 7
<211> LENGTH: 10
<212> TYPE: PRT
<213> ORGANISM: Artificial Sequence
```

<220> FEATURE:
<223> OTHER INFORMATION: Description of Artificial Sequence: note =
      Synthetic Construct

<400> SEQUENCE: 7

Leu Arg Lys Met Arg Lys Arg Leu Met Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 8

Leu Arg Lys Leu Pro Lys Arg Leu Leu Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 9

Leu Arg Asn Val Arg Lys Arg Leu Val Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 10

Met Arg Lys Leu Arg Lys Arg Val Leu Arg
1               5                   10

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 11

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 12

```
Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25
```

```
<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 13
```

```
Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25
```

```
<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 14
```

```
Leu Arg Lys Met Arg Lys Arg Leu Met Arg Asp Trp Leu Lys Ala Phe
1               5                   10                  15

Tyr Asp Lys Val Ala Glu Lys Leu Lys Glu Ala Phe
            20                  25
```

```
<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 15
```

```
Leu Arg Lys Leu Arg Lys Arg Phe Phe Arg
1               5                   10
```

```
<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 16
```

```
Asp Trp Leu Lys Ala Phe Tyr Asp Lys Val Ala Glu Lys Leu Lys Glu
1               5                   10                  15

Ala Phe
```

```
<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 17

Asp Trp Phe Lys Ala Phe Tyr Asp Lys Val Ala Glu Lys Phe Lys Glu
1               5                   10                  15

Ala Phe

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 18

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 19

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 20

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 21

Leu Arg Lys Met Arg Lys Arg Leu Met Arg Asp Trp Leu Lys Ala Phe
1               5                   10                  15

Tyr Asp Lys Val Ala Glu Lys Leu Lys Glu Ala Phe
            20                  25

<210> SEQ ID NO 22
<211> LENGTH: 28
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 22

Leu Arg Lys Met Arg Lys Arg Leu Met Arg Asp Trp Leu Lys Ala Phe
1               5                   10                  15

Tyr Asp Lys Val Ala Glu Lys Leu Lys Glu Ala Phe
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 23

Leu Arg Lys Leu Pro Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 24

Leu Arg Asn Val Arg Lys Arg Leu Val Arg Asp Trp Leu Lys Ala Phe
1               5                   10                  15

Tyr Asp Lys Val Ala Glu Lys Leu Lys Glu Ala Phe
            20                  25

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 25

Met Arg Lys Leu Arg Lys Arg Val Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 26

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
```

```
<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 27

Leu Arg Lys Leu Arg Lys Arg Phe Phe Arg Asp Trp Leu Lys Ala Phe
1               5                   10                  15

Tyr Asp Lys Val Ala Glu Lys Leu Lys Glu Ala Phe
            20                  25

<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 28

Leu Arg Lys Leu Arg Lys Arg Leu Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 29

Leu Arg Lys Leu Arg Lys Arg Leu Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 30

Leu Arg Lys Leu Arg Lys Arg Leu Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 31

Leu Arg Lys Met Arg Lys Arg Leu Met Arg Asp Trp Phe Lys Ala Phe
1               5                   10                  15

Tyr Asp Lys Val Ala Glu Lys Phe Lys Glu Ala Phe
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 32

Leu Arg Lys Met Arg Lys Arg Leu Met Arg Asp Trp Phe Lys Ala Phe
1               5                   10                  15

Tyr Asp Lys Val Ala Glu Lys Phe Lys Glu Ala Phe
            20                  25

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 33

Leu Arg Lys Leu Pro Lys Arg Leu Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 34

Leu Arg Asn Val Arg Lys Arg Leu Val Arg Asp Trp Phe Lys Ala Phe
1               5                   10                  15

Tyr Asp Lys Val Ala Glu Lys Phe Lys Glu Ala Phe
            20                  25

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 35

Met Arg Lys Leu Arg Lys Arg Val Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 36
<211> LENGTH: 28
```

<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 36

Leu Arg Arg Leu Arg Arg Arg Leu Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 37

Leu Arg Lys Leu Arg Lys Arg Phe Phe Arg Asp Trp Phe Lys Ala Phe
1               5                   10                  15

Tyr Asp Lys Val Ala Glu Lys Phe Lys Glu Ala Phe
            20                  25

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 38

Asp Trp Leu Lys Ala Phe Tyr Asp Lys Val Ala Glu Lys Leu Lys Glu
1               5                   10                  15

Ala Phe Leu Arg Lys Leu Arg Lys Arg Leu Leu Arg
            20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 39

Asp Trp Leu Lys Ala Phe Tyr Asp Lys Val Ala Glu Lys Leu Lys Glu
1               5                   10                  15

Ala Phe Leu Arg Lys Leu Arg Lys Arg Leu Leu Arg
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 40

Asp Trp Leu Lys Ala Phe Tyr Asp Lys Val Ala Glu Lys Leu Lys Glu
1               5                   10                  15

```
Ala Phe Leu Arg Lys Leu Arg Lys Arg Leu Leu Arg
            20                  25
```

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 41

```
Asp Trp Leu Lys Ala Phe Tyr Asp Lys Val Ala Glu Lys Leu Lys Glu
1               5                   10                  15

Ala Phe Leu Arg Lys Met Arg Lys Arg Leu Met Arg
            20                  25
```

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 42

```
Asp Trp Leu Lys Ala Phe Tyr Asp Lys Val Ala Glu Lys Leu Lys Glu
1               5                   10                  15

Ala Phe Leu Arg Lys Met Arg Lys Arg Leu Met Arg
            20                  25
```

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 43

```
Asp Trp Leu Lys Ala Phe Tyr Asp Lys Val Ala Glu Lys Leu Lys Glu
1               5                   10                  15

Ala Phe Leu Arg Lys Leu Pro Lys Arg Leu Leu Arg
            20                  25
```

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 44

```
Asp Trp Leu Lys Ala Phe Tyr Asp Lys Val Ala Glu Lys Leu Lys Glu
1               5                   10                  15

Ala Phe Leu Arg Asn Val Arg Lys Arg Leu Val Arg
            20                  25
```

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

```
<400> SEQUENCE: 45

Asp Trp Leu Lys Ala Phe Tyr Asp Lys Val Ala Glu Lys Leu Lys Glu
1               5                   10                  15

Ala Phe Met Arg Lys Leu Arg Lys Val Leu Arg
            20                  25

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 46

Asp Trp Leu Lys Ala Phe Tyr Asp Lys Val Ala Glu Lys Leu Lys Glu
1               5                   10                  15

Ala Phe Leu Arg Arg Leu Arg Arg Arg Leu Leu Arg
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 47

Asp Trp Leu Lys Ala Phe Tyr Asp Lys Val Ala Glu Lys Leu Lys Glu
1               5                   10                  15

Ala Phe Leu Arg Lys Leu Arg Lys Arg Phe Phe Arg
            20                  25

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 48

Asp Trp Phe Lys Ala Phe Tyr Asp Lys Val Ala Glu Lys Phe Lys Glu
1               5                   10                  15

Ala Phe Leu Arg Lys Leu Arg Lys Arg Leu Leu Arg
            20                  25

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 49

Asp Trp Phe Lys Ala Phe Tyr Asp Lys Val Ala Glu Lys Phe Lys Glu
1               5                   10                  15

Ala Phe Leu Arg Lys Leu Arg Lys Arg Leu Leu Arg
            20                  25

<210> SEQ ID NO 50
```

```
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 50

Asp Trp Phe Lys Ala Phe Tyr Asp Lys Val Ala Glu Lys Phe Lys Glu
1               5                   10                  15

Ala Phe Leu Arg Lys Leu Arg Lys Arg Leu Leu Arg
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 51

Asp Trp Phe Lys Ala Phe Tyr Asp Lys Val Ala Glu Lys Phe Lys Glu
1               5                   10                  15

Ala Phe Leu Arg Lys Met Arg Lys Arg Leu Met Arg
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 52

Asp Trp Phe Lys Ala Phe Tyr Asp Lys Val Ala Glu Lys Phe Lys Glu
1               5                   10                  15

Ala Phe Leu Arg Lys Met Arg Lys Arg Leu Met Arg
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 53

Asp Trp Phe Lys Ala Phe Tyr Asp Lys Val Ala Glu Lys Phe Lys Glu
1               5                   10                  15

Ala Phe Leu Arg Lys Leu Pro Lys Arg Leu Leu Arg
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 54

Asp Trp Phe Lys Ala Phe Tyr Asp Lys Val Ala Glu Lys Phe Lys Glu
1               5                   10                  15
```

```
Ala Phe Leu Arg Asn Val Arg Lys Arg Leu Val Arg
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 55

Asp Trp Phe Lys Ala Phe Tyr Asp Lys Val Ala Glu Lys Phe Lys Glu
1               5                   10                  15

Ala Phe Met Arg Lys Leu Arg Lys Arg Val Leu Arg
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 56

Asp Trp Phe Lys Ala Phe Tyr Asp Lys Val Ala Glu Lys Phe Lys Glu
1               5                   10                  15

Ala Phe Leu Arg Arg Leu Arg Arg Arg Leu Leu Arg
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 57

Asp Trp Phe Lys Ala Phe Tyr Asp Lys Val Ala Glu Lys Phe Lys Glu
1               5                   10                  15

Ala Phe Leu Arg Lys Leu Arg Lys Arg Phe Phe Arg
            20                  25

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 58

Leu Arg Leu Leu Arg Lys Leu Lys Arg Arg
1               5                   10

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 59
```

```
Lys Ala Phe Glu Glu Val Leu Ala Lys Lys Phe Tyr Asp Lys Ala Leu
1               5                   10                  15

Trp Asp

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 60

Leu Arg Lys Leu Arg Lys Arg Leu Leu Arg Lys Ala Phe Glu Glu Val
1               5                   10                  15

Leu Ala Lys Lys Phe Tyr Asp Lys Ala Leu Trp Asp
            20                  25

<210> SEQ ID NO 61
<211> LENGTH: 27
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 61

Leu Arg Leu Leu Arg Lys Leu Lys Arg Arg Asp Trp Leu Lys Ala Phe
1               5                   10                  15

Tyr Asp Lys Val Glu Lys Leu Lys Glu Ala Phe
            20                  25

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 62

Gly Phe Arg Arg Phe Leu Gly Ser Trp Ala Arg Ile Tyr Arg Ala Phe
1               5                   10                  15

Val Gly

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 63

Leu Arg Lys Leu Arg Lys Arg Leu Leu Arg Asp Trp Phe Lys Ala Phe
1               5                   10                  15

Tyr Asp Lys Val Ala Glu Lys Phe Lys Glu Ala Phe
            20                  25

<210> SEQ ID NO 64
<211> LENGTH: 28
<212> TYPE: PRT
<213> ORGANISM: Artificial Sequence
<220> FEATURE:
```

-continued

<223> OTHER INFORMATION: Description of Artificial Sequence: note =
     Synthetic Construct

<400> SEQUENCE: 64

Arg Leu Leu Arg Lys Arg Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: note =
     Synthetic Construct

<400> SEQUENCE: 65

Arg Leu Leu Arg Lys Arg Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: note =
     Synthetic Construct

<400> SEQUENCE: 66

Arg Leu Leu Arg Lys Arg Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: note =
     Synthetic Construct

<400> SEQUENCE: 67

Arg Met Leu Arg Lys Arg Met Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: note =
     Synthetic Construct

<400> SEQUENCE: 68

Arg Met Leu Arg Lys Arg Met Lys Arg Leu Asp Trp Leu Lys Ala Phe
1               5                   10                  15

Tyr Asp Lys Val Ala Glu Lys Leu Lys Glu Ala Phe
            20                  25

```
<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 69
```

Arg Leu Leu Arg Lys Pro Leu Lys Arg Leu Asp Trp Leu Lys Ala Phe
1               5                   10                  15

Tyr Asp Lys Val Ala Glu Lys Leu Lys Glu Ala Phe
            20                  25

```
<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 70
```

Arg Val Leu Arg Lys Arg Val Asn Arg Leu Asp Trp Leu Lys Ala Phe
1               5                   10                  15

Tyr Asp Lys Val Ala Glu Lys Leu Lys Glu Ala Phe
            20                  25

```
<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 71
```

Arg Leu Val Arg Lys Arg Leu Lys Arg Met Asp Trp Leu Lys Ala Phe
1               5                   10                  15

Tyr Asp Lys Val Ala Glu Lys Leu Lys Glu Ala Phe
            20                  25

```
<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 72
```

Arg Leu Leu Arg Arg Arg Leu Arg Arg Leu Asp Trp Leu Lys Ala Phe
1               5                   10                  15

Tyr Asp Lys Val Ala Glu Lys Leu Lys Glu Ala Phe
            20                  25

```
<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 73
```

Arg Phe Phe Arg Lys Arg Leu Lys Arg Leu Asp Trp Leu Lys Ala Phe
1               5                   10                  15

Tyr Asp Lys Val Ala Glu Lys Leu Lys Glu Ala Phe
            20                  25

<210> SEQ ID NO 74
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 74

Arg Leu Leu Arg Lys Arg Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 75

Arg Leu Leu Arg Lys Arg Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 76

Arg Leu Leu Arg Lys Arg Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 77

Arg Met Leu Arg Lys Arg Met Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 78
<211> LENGTH: 28
<212> TYPE: PRT
<213> ORGANISM: Artificial Sequence

```
<220> FEATURE:
<223> OTHER INFORMATION: Description of Artificial Sequence: note =
      Synthetic Construct

<400> SEQUENCE: 78

Arg Met Leu Arg Lys Arg Met Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 79

Arg Leu Leu Arg Lys Pro Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 80
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 80

Arg Val Leu Arg Lys Arg Val Asn Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 81

Arg Leu Val Arg Lys Arg Leu Lys Arg Met Asp Trp Phe Lys Ala Phe
1               5                   10                  15

Tyr Asp Lys Val Ala Glu Lys Phe Lys Glu Ala Phe
            20                  25

<210> SEQ ID NO 82
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 82

Arg Leu Leu Arg Arg Arg Leu Arg Arg Leu Asp Trp Phe Lys Ala Phe
1               5                   10                  15

Tyr Asp Lys Val Ala Glu Lys Phe Lys Glu Ala Phe
            20                  25
```

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 83

Arg Phe Phe Arg Lys Arg Leu Lys Arg Leu Asp Trp Phe Lys Ala Phe
1               5                   10                  15

Tyr Asp Lys Val Ala Glu Lys Phe Lys Glu Ala Phe
            20                  25

<210> SEQ ID NO 84
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 84

Leu Arg Lys Leu Arg Lys Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 85

Leu Arg Lys Leu Arg Lys Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 86
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 86

Leu Arg Lys Leu Arg Lys Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 87

```
Leu Arg Lys Met Arg Lys Arg Leu Met Arg Phe Ala Glu Lys Leu Lys
1               5                   10                  15

Glu Ala Val Lys Asp Tyr Phe Ala Lys Leu Trp Asp
            20                  25

<210> SEQ ID NO 88
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 88

Leu Arg Lys Met Arg Lys Arg Leu Met Arg Phe Ala Glu Lys Leu Lys
1               5                   10                  15

Glu Ala Val Lys Asp Tyr Phe Ala Lys Leu Trp Asp
            20                  25

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 89

Leu Arg Lys Leu Pro Lys Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 90
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 90

Leu Arg Asn Val Arg Lys Arg Leu Val Arg Phe Ala Glu Lys Leu Lys
1               5                   10                  15

Glu Ala Val Lys Asp Tyr Phe Ala Lys Leu Trp Asp
            20                  25

<210> SEQ ID NO 91
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 91

Met Arg Lys Leu Arg Lys Arg Val Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 92
<211> LENGTH: 28
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 92

Leu Arg Arg Leu Arg Arg Arg Leu Leu Arg Phe Ala Glu Lys Leu Lys
1               5                   10                  15

Glu Ala Val Lys Asp Tyr Phe Ala Lys Leu Trp Asp
            20                  25

<210> SEQ ID NO 93
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 93

Leu Arg Lys Leu Arg Lys Arg Phe Phe Arg Phe Ala Glu Lys Leu Lys
1               5                   10                  15

Glu Ala Val Lys Asp Tyr Phe Ala Lys Leu Trp Asp
            20                  25

<210> SEQ ID NO 94
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 94

Leu Arg Lys Leu Arg Lys Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 95
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 95

Leu Arg Lys Leu Arg Lys Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 96

Leu Arg Lys Leu Arg Lys Arg Leu Leu Arg Phe Ala Glu Lys Phe Lys
1               5                   10                  15

Glu Ala Val Lys Asp Tyr Phe Ala Lys Phe Trp Asp
```

20                  25

<210> SEQ ID NO 97
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 97

Leu Arg Lys Met Arg Lys Arg Leu Met Arg Phe Ala Glu Lys Phe Lys
1               5                   10                  15

Glu Ala Val Lys Asp Tyr Phe Ala Lys Phe Trp Asp
            20                  25

<210> SEQ ID NO 98
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 98

Leu Arg Lys Met Arg Lys Arg Leu Met Arg Phe Ala Glu Lys Phe Lys
1               5                   10                  15

Glu Ala Val Lys Asp Tyr Phe Ala Lys Phe Trp Asp
            20                  25

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 99

Leu Arg Lys Leu Pro Lys Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 100

Leu Arg Asn Val Arg Lys Arg Leu Val Arg Phe Ala Glu Lys Phe Lys
1               5                   10                  15

Glu Ala Val Lys Asp Tyr Phe Ala Lys Phe Trp Asp
            20                  25

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

```
<400> SEQUENCE: 101

Met Arg Lys Leu Arg Lys Arg Val Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 102

Leu Arg Arg Leu Arg Arg Arg Leu Leu Arg Phe Ala Glu Lys Phe Lys
1               5                   10                  15

Glu Ala Val Lys Asp Tyr Phe Ala Lys Phe Trp Asp
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 103

Leu Arg Lys Leu Arg Lys Arg Phe Phe Arg Phe Ala Glu Lys Phe Lys
1               5                   10                  15

Glu Ala Val Lys Asp Tyr Phe Ala Lys Phe Trp Asp
            20                  25

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Note=
      Synthetic Consruct

<400> SEQUENCE: 104

Arg Leu Thr Arg Lys Arg Gly Leu Lys
1               5
```

SYNTHETIC APOLIPOPROTEIN E MIMICKING POLYPEPTIDES AND METHODS OF USE

CROSS-REFERENCE TO RELATED PATENT APPLICATIONS

The present application is a National Phase Application of International Application No. PCT/US2008/074470, filed Aug. 27, 2008, which claims priority to U.S. Provisional Application No. 60/968,362, titled Synthetic Apolipoprotein E Mimicking Polypeptides and Methods of Use, filed on Aug. 28, 2007, which is hereby incorporated herein by reference in its entirety.

FIELD OF THE INVENTION

This invention relates to the field of molecular biology and protein biology including polypeptides and polypeptide mimics. This application also relates to the field of plasma glucose metabolism, catabolism, and the treatment and management of plasma glucose associated conditions such as diabetes. The present invention also relates generally to the field of medicine. More specifically, the present invention relates to synthetic peptides that can rapidly lower plasma glucose.

BACKGROUND OF THE INVENTION

Diabetes mellitus (DM) is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; vulnerability to coronary artery disease and myocardial infarction, gastroparesis, diseases associated with the autonomic nervous-system, nerve condition abnormalities, i.v. contrast induced nephropathy, small vessel diseases (both within the brain and outside the brain), hypogonadism, and heart failure.

DM is a group of disorders characterized by high levels of blood glucose. Prevalence of DM is reaching epidemic proportions in the United States and the world. In 2005, approximately 21 million people in the U.S. had DM of which 90%-95% had type-2 DM (DM-2). Every hour, in the United States, approximately 4100 new cases of DM are diagnosed, and 810 people die from complications of DM. In 2002, DM was the sixth leading cause of death in the U.S. and cost $132 billion. In 2005, DM was responsible for 11.2 million deaths world wide. Contrary to the conventional wisdom, DM affects all socio-economic strata in the world. Cardiovascular complications are the most common causes of morbidity and mortality in DM-2, accounting for up to 70% of the mortality. Interestingly pre-diabetes, where people have high blood glucose but not sufficient to be classified as DM-2, affects 54 million in the U.S. with age greater than 20 years. These people are at increased risk of DM-2 and cardiovascular disease. Despite significant decline in the coronary heart disease mortality, the effects of such a decline are less significant in diabetics as compared to non-diabetics.

There are two primary types of diabetes. Type I, or insulin-dependent diabetes mellitus (IDDM), is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions. Type II diabetes (DM2), or noninsulin-dependent diabetes mellitus (NIDDM), typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlay many of the major causes of morbidity and death of people over age 40.

DM-2, which accounts for 90%-95% of all DM, is characterized by insulin resistance and relative insulin deficiency. In the early stages, this may manifest as glucose intolerance with relatively non-specific symptoms and may not be diagnosed. However, these patients are at increased risk for continuing progression of the disease with associated clinical complications involving multiple organs. Attempts to delay the onset and progression of DM-2 have met with mixed success. Published in 2002, the Diabetes Prevention Study (DPP) demonstrated that lifestyle modification consisting of moderate exercise regimen and dietary modification can be effective in preventing/delaying the rate of onset of DM-2. However significant barriers like behavioral modification make the routine implementation of this strategy difficult. Pharmaceutical agents such as metformin have also demonstrated the effectiveness of preventing/delaying the onset of DM-2. Despite advances in the medical and lifestyle therapies, the incidence and prevalence of the DM-2 continues to increase. Even more interesting is the fact that cardiovascular disease in DM-2 is more aggressive with earlier onset. DM-2 demonstrates characteristic lipoprotein changes including lower high density lipoprotein (HDL) and higher triglycerides (TG) concentrations. Low density lipoproteins (LDL) in DM-2 may not be markedly elevated as compared to control cohort. However, small dense LDL is present in greater concentration. This characteristic diabetic dyslipidemia is associated with markedly increased cardiovascular disease mortality (MRFIT) as compared to non-diabetics. Statins are a class of drugs that predominantly lower LDL. These medications are effective in reducing cardiovascular disease risks in both DM and non-DM, however the residual CVD risk in DM despite LDL lowering remains higher than non-diabetics taking placebo. Elevated HDL may provide an additional mechanism of cardiovascular disease risk reduction in both diabetics and non-diabetics. Multiple trials are ongoing to evaluate the efficacy of increasing HDL in decreasing CVD risk in both diabetic and non-diabetic population.

Despite the existence of drugs to treat such disorders, diabetes and other insulin-resistant disorders remain a major and growing public health problem. Late stage complications of diabetes consume a large proportion of national health care resources. There is a need for new active therapeutic agents which effectively address the primary defects of insulin resistance and islet failure with fewer or milder side effects than existing drugs. What is needed in the art are compositions and methods for treating insulin resistance.

Apolipoprotein E is a protein that binds lipid and has two major domains (Mahley, R. W., et al. *J. Lipid Res.* 1999, 40:622-630). The 22 kDa amino terminal domain has been shown by X-ray crystallographic studies to be a 4-helix bundle (Wilson, C., et al. *Science* 1991; 252: 1817-1822) and to contain a positively-charged receptor binding domain. For this region to mediate very low-density lipoprotein (VLDL) binding to its receptors, the apolipoprotein must associate with the lipoprotein surface; this is enabled by the C-terminal amphipathic helical region. If the 4-helix bundle that contains the positively charged receptor-binding domain does not open up on the lipoprotein surface, then the VLDL is defective in binding to receptors. Thus, the positively charged arginine (Arg)-rich cluster domain of the Apo E and the C-terminal amphipathic helical domain, are both required for the enhanced uptake of atherogenic Apo E-containing lipoproteins.

Apo E is secreted as a 299 amino acid residue protein with a molecular weight of 34,200. Based on thrombin cleavage of apo E into two fragments, a two-domain hypothesis was initially suggested to explain the fact that the C-terminal region of apo E (192-299) is essential for its binding to hypertriglyceridemic VLDL, and the N-terminal 22 kDa domain (1-191) binds to the LDL-R (Bradley, W. A., et al., (1986) J. Lipid Res. 27, 40-48). Additional physical-chemical characterization of the protein and its mutants have extended this concept and have shown that the region 192-211 binds to phospholipid while the amino terminal domain (1-191) is a globular structure that contains the LDL receptor binding domain in the 4-helix bundle (Wilson, C., et al., (1991) Science 252, 1817-1822). Studies with synthetic peptides (Sparrow et al.) and monoclonal antibodies pinpointed the LDL receptor binding domain of apo E between residues 129-169, a domain enriched in positively charged amino acids, Arg and Lys (Rall, S. C., Jr., et al., (1982) PNAS USA 79, 4696-4700; Lalazar, A., et al., (1988) J. Biol. Chem. 263, 3542-2545; Dyer, C. A., et al., (1991) J. Biol. Chem. 296, 22803-22806; and Dyer, C. A., et al., (1991) J. Biol. Chem. 266, 15009-15015).

Further studies with synthetic peptides were used to characterize the structural features of the binding domain of apo E that mediates its interaction with the LDL receptor (Dyer, C. A., et al., (1991) J. Biol. Chem. 296, 22803-22806; Dyer, C. A., et al., (1991) J. Biol. Chem. 266, 15009-15015; and Dyer, C. A., et al., (1995) J. Lipid Res. 36, 80-8). Residues 141-155 of apo E, although containing the positively charged residues, did not compete for binding of LDL in a human skin fibroblast assay, but did so only as tandem covalent repeats [i.e., (141-155)$_2$]. N-acetylation of the (141-155)$_2$ peptide, on the other hand, enhanced LDL binding to fibroblasts (Nicoulin, I. R., et al., (1998) J. Clin Invest. 101, 223-234). The N-acetylated (141-155)$_2$ analog selectively associated with cholesterol-rich lipoproteins and mediated their acute clearance in vivo (Nicoulin, I. R., et al., (1998) J. Clin Invest. 101, 223-234). Furthermore, these studies indicated that the prerequisite for receptor binding is that the peptides be helical (Dyer, C. A., et al., (1995) J. Lipid Res. 36, 80-88). Enhanced LDL uptake and degradation were also observed (Mims, M. P., et al., (1994) J. Biol. Chem. 269, 20539-20647) using synthetic peptides modified to increase lipid association by N,N-distearyl derivation of glycine at the N-terminus of the native 129-169 sequence of Apo E (Mims, M. P., et al., (1994) J. Biol. Chem. 269, 20539-20647). Although LDL binding is mediated by the cationic sequence 141-155 of human Apo E, Braddock et al. (Braddock. D. T., et al., (1996) Biochemistry 35, 13975-13984) have shown that model peptides of the highly conserved anionic domain (41-60 of human Apo E) also modulate the binding and internalization of LDL to cell surface receptors. However, these peptides do not enhance LDL degradation.

Chylomicron is a lipoprotein found in blood plasma, which carries lipids from the intestines into other body tissues and is made up of a drop of triacylglycerols surrounded by a protein-phospholipid coating. Chylomicron remnants are taken up by the liver (Havel, R. J., 1985, Arteriosclerosis. 5:569-580) after sequestration in the space of Disse, which is enriched with Apo E (Kwiterovich, P. O., Jr., 1998; Deedwania, P. C., 1995; and Watts, G. W., et al., 1998). Apo E is the major mediator of hepatic remnant lipoprotein uptake by the LDL receptor or LRP. Lipolysis of normal VLDL Sf (subfraction) of more than 60 permit binding of the lipolytic remnant to the LDL receptor (Catapano, A. L. et al. 1979, J. Biol. Chem. 254:1007-1009; Schonfield, G., et al. 1979. J. Clin. Invest. 64:1288-1297). Lipoprotein lipase (LpL) may facilitate uptake through localization of Apo B-containing lipoproteins to membrane heparan sulphate proteoglycan (HSPG) (Eisenberg, et al. 1992. J. Clin. Invest. 90:2013-2021; Hussain, M., et al., J. Biol. Chem. 2000, 275:29324-29330) and/or through binding to the LDL-receptor-related protein (LRP) (Beisiegel, U., et al., 1989, Nature 341:162-164). Cell-surface HSPG may also function as a receptor and has variable binding affinities for specific isoforms of Apo E. In particular, Apo E is synthesized by the liver and also by monocyte/macrophages, where it exerts its effect on cholesterol homeostasis. In vivo evidence for the local effect of lack of Apo E comes from the observations of Linton and Fazio, who showed accelerated atherosclerosis in C57BL/6 mice transplanted with bone marrow from Apo E-deficient mice (Linton, M. F. and Fazio, S. Curr. Openi. Lipidol. 1999, 10:97-105). Apo E-dependent LDL cholesteryl ester uptake pathway has been demonstrated in murine adrenocortical cells (Swarnakar, S., et al. J. Biol. Chem. 2001, 276:21121-21126). This appears to involve chondroitin sulphate proteoglycan (CSPG) and a 2-macroglobulin receptor.

U.S. Pat. No. 6,506,880 denotes the first effort to synthesize apolipoprotein E-mimicking peptides based on the hypothesis that since lipid binding is essential for surface localization of the peptide on lipoproteins and for the receptor binding domain of apo E to be appropriately accessible to bind to the LDL receptor, joining a well-characterized, lipid-associating peptide such as the model class A amphipathic helix, 18A, to the 141-150 peptide sequence of apo E should be sufficient to confer biological activity.

The present invention provides novel synthetic ApoE-mimicking peptides wherein the receptor binding domain of ApoE is covalently linked to 18A, the well characterized lipid-associating model class A amphipathic helical peptide as well as possible applications of the synthetic peptides in lowering human plasma glucose levels.

SUMMARY OF THE INVENTION

The present invention provides polypeptides, compositions, and methods of use of said polypeptides and compositions.

Disclosed herein are methods of decreasing the concentration of plasma glucose in a subject, comprising: administering a synthetic apolipoprotein E-mimicking peptide to the subject, whereby the concentration of plasma glucose in the subject decreases.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a sequence selected from the group consisting of SEQ ID NOs: 11-14, 18-57, 60, 61, and 62-103. Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein the receptor binding domain peptide is from a species selected from the group consisting of human, mouse, rabbit, monkey, rat, bovine, pig, and dog.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein the receptor binding domain peptide comprises a sequence selected from the group consisting of SEQ ID NOs: 1-2, 3, 5-10, 15, and 58.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein the receptor binding domain peptide is mutated Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein the receptor binding domain peptide is scrambled.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein the receptor binding domain peptide is in a reversed orientation.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein the lipid-associating peptide is model class A amphipathic helical peptide 18A.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein said lipid-associating peptide comprises a sequence selected from the group consisting of SEQ ID NOs: 4, 16, 17, and 59.

Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide comprises a receptor binding domain peptide and a lipid-associating peptide, wherein said lipid binding domain peptide is covalently linked to said receptor binding domain peptide, wherein the lipid-associating peptide is mutated, scrambled, or is in a domain switched orientation.

Also disclosed are methods for decreasing the concentration of plasma glucose in a subject, comprising: administering a pharmaceutical composition comprising a synthetic apolipoprotein E-mimicking peptide and a pharmaceutically acceptable carrier to the subject, whereby the concentration of plasma glucose in the subject decreases. Also disclosed are methods of treating a subject with diabetes comprising administering an effective amount of a pharmaceutical composition comprising a synthetic apolipoprotein E-mimicking peptide and a pharmaceutically acceptable carrier to the subject, whereby the concentration of plasma glucose in the subject decreases. Also disclosed are methods of treating a subject with diabetes comprising: selecting a subject with diabetes; administering an effective amount of a synthetic apolipoprotein E-mimicking peptide to the subject; thereby treating diabetes in the subject.

Also disclosed are methods of treating a subject with diabetes comprising: selecting a subject with diabetes; and administering an effective amount of a pharmaceutical composition comprising a synthetic apolipoprotein E-mimicking peptide and a pharmaceutically acceptable carrier to the subject; thereby treating diabetes in the subject.

BRIEF DESCRIPTION OF THE DRAWINGS

The accompanying drawings, which are incorporated in and constitute a part of this specification, illustrate several embodiments of the invention and together with the description, serve to explain the principles of the invention. These are non-limiting examples.

DETAILED DESCRIPTION OF THE INVENTION

Figure 1:
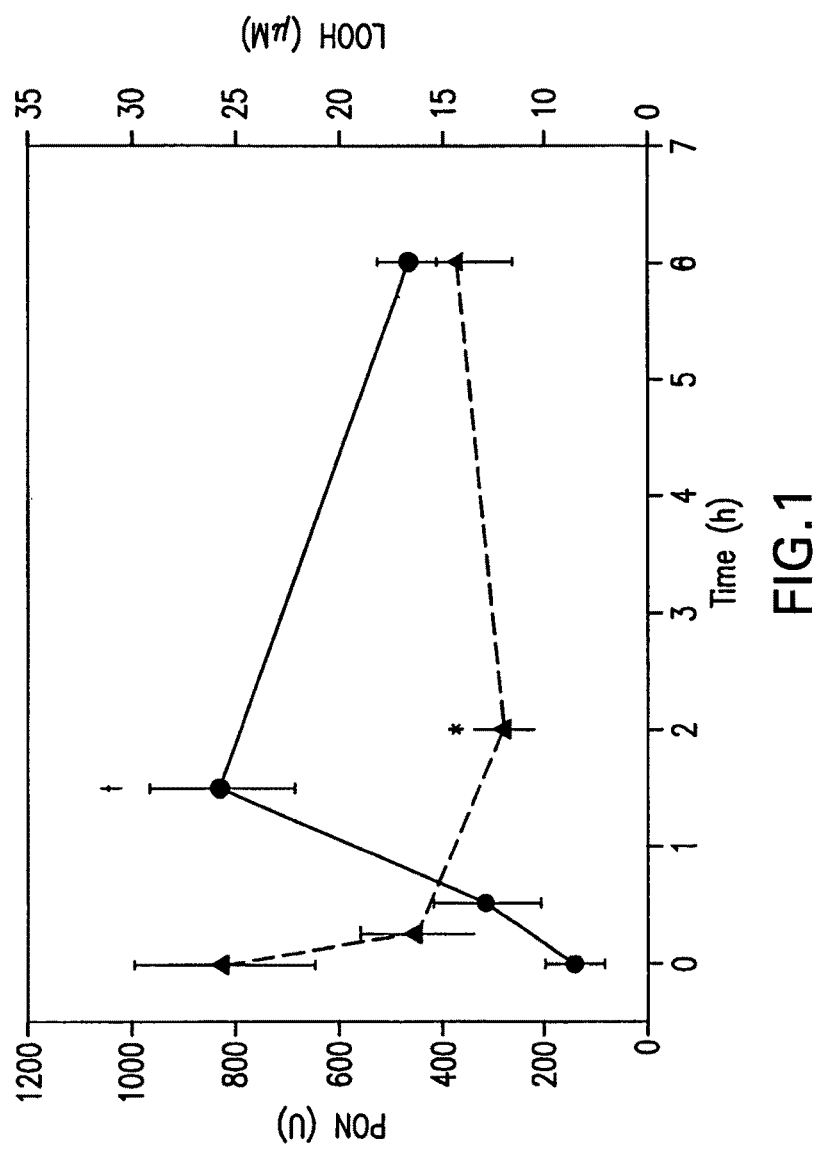
FIG. 1 shows Ac-hE18A-NH$_2$ causes an increase in HDL associated Paraoxonase (PON) ($p<0.05$) activity and a decrease in lipid hydroperoxides (LOOH) ($p<0.05$) in the plasma of WHHL rabbits.

All patents, patent applications, and publications cited herein, whether supra or infra, are hereby incorporated by reference in their entireties into this application in order to more fully describe the state of the art as known to those skilled therein as of the date of the invention described and claimed herein.

It is to be understood that this invention is not limited to specific synthetic methods, or to specific recombinant biotechnology methods unless otherwise specified, or to particular reagents unless otherwise specified, to specific pharmaceutical carriers, or to particular pharmaceutical formulations or administration regimens, as such may, of course, vary. It is also to be understood that the terminology used herein is for the purpose of describing particular embodiments only and is not intended to be limiting.

1. Definitions and Nomenclature

The terminology used herein is for the purpose of describing particular embodiments only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (*See Proteins—Structure and Molecular Properties* 2nd Ed., T. E. Creighton, W.H. Freeman and Company, New York (1993); *Posttranslational Covalent Modification of Proteins*, B. C. Johnson, Ed., Academic Press, New York, pp. 1-12 (1983)).

As used herein, "peptidomimetic" means a mimetic of a function of a protein which includes some alteration of the normal peptide chemistry. Peptidomimetics typically are short sequences of amino acids that in biological properties, mimic the function(s) of a particular protein. Peptide analogs enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural L- or D-amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "reverse oriented", "reversed orientation", "reverse analog" or "reverse sequence" refers to a peptide, or a portion of the peptide, has a reverse amino acid sequence as compared to a non-reverse oriented peptide (i.e., the original sequence is read (or written) from right to left). For example, if one peptide has the amino acid sequence ABCDE, its reverse analog or a peptide having its reverse sequence is as follows: EDCBA. In a dual domain peptide for example, Ac-hE-18A-NH$_2$, either the hE sequence is read from right to left or the 18A sequence is read from right to left. For a reverse analog of,

```
LRKLRKRLLR-DWLKAFYDKVAEKLKEAF    (SEQ ID NO: 11)
can be

RLLRKRLKRL-DWLKAFYDKVAEKLKEAF    (SEQ ID NO: 64)
or

LRKLRKRLLR-FAEKLKEAVKDYFAKLWD    (SEQ ID NO: 84).
```

As used herein a "synthetic apolipoprotein E-mimicking peptide" is meant to include a dual-domain ApoE mimicking peptide or a single-domain ApoE mimicking peptide as disclosed herein.

As used herein a "dual-domain peptide", a "dual-domain synthetic peptide", or a "dual-domain ApoE mimicking peptide" is meant to mean a peptide comprising a lipid-associating peptide/domain and a receptor binding peptide/domain.

As used herein a "single-domain peptide", a "single-domain synthetic peptide", or a "single-domain ApoE mimicking peptide" is meant to mean a peptide comprising either a lipid-associating peptide/domain or a receptor binding peptide/domain, or a single domain amphipathic helix with hydrophobic residues on the nonpolar face and arginine residues at the center of the polar face, but not all.

As used herein "domain switched", "switched domain", or "switched" peptide is meant to mean that the lipid-associating peptide is covalently linked to the receptor binding domain of apolipoprotein E such that the lipid-associating peptide is at the N-terminus of the synthetic apolipoprotein E-mimicking peptide. For example, the peptide 18A-hE (SEQ ID NO: 38) is exemplary of a domain switched peptide.

As used herein, "scrambled" "scrambled version", or "scrambled peptide" is meant to mean that the composition of the amino acid sequence is the same as the unscrambled peptide, however the sequence of the amino acids is altered thus rendering the peptide unable to form either an α-amphipathic helix or does not possess lipid associating (or HSPG associating) properties. However, in some cases, as described in this invention, the scrambled peptide remains able to form a different helical structure, such as a π-helix. For example, if one peptide has the amino acid sequence ABCDE, the scrambled version of the peptide could have the amino acid sequence DEABC. Scrambled peptides are often denoted as having an "Sc" prior to the portion of the peptide that is scrambled. For example, Sc-hE-18A denoted that the hE portion of the peptide is scrambled.

An "α-amphipathic helix" is discussed above and has 3.6 amino acid residues per turn of the helix, whereas a "π-helix" has 4.4 amino acid residues per turn.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "modulate" is meant to mean to alter, by increasing or decreasing.

As used herein "lipid binding domain E" and "lipid-associating peptide" are used interchangeably. As used herein, both terms can mean the lipid binding domain of Apolipoprotein E.

As used herein, "normal subject" is meant to mean an individual who does not have "Diabetes" or a "Diabetic Complication".

As used herein, "diabetes" or "diabetes mellitus" shall mean a metabolic disorder characterized by hyperglycemia (high blood sugar) and other signs, as distinct from a single illness or condition. The term "diabetes" or "diabetes mellitus" as used herein is meant to include the three main forms of diabetes recognized by the World Health Organization, namely: type 1, type 2, gestational diabetes (occurring during pregnancy), and/or associated complications such as juvenile onset diabetes, diabetic nephropathy, diabetic neuropathy, and diabetic retinopathy. The term "diabetes" or "diabetes mellitus" as used herein is also meant to mean all forms of diabetes caused by the beta cells of the pancreas being unable to produce sufficient insulin to prevent hyperglycemia. The term "diabetes" or "diabetes mellitus" as used herein is also meant to include glucose intolerance and diabetes glucose-intolerant subjects.

As used herein, "Inflammatory Disorder" is meant to mean when a subject experiences a cascade of reactions initiated by oxidized lipids in which several cytokine levels go up to alter the normal physiological response. Inflammatory disorders include, but are not limited to Inflammatory Bowel Disease (IBD), systemic lupus erythematosus, Hashimoto's disease, rheumatoid arthritis, graft-versus-host disease, Sjögren's syndrome, pernicious anemia, Addison disease, Alzheimer's disease, scleroderma, Goodpasture's syndrome, ulcerative colitis, Crohn's disease, autoimmune hemolytic anemia, sterility, myasthenia gravis, multiple sclerosis, Basedow's disease, thrombopenia purpura, allergy; asthma, atopic disease, cardiomyopathy, glomerular nephritis, hypoplastic anemia, metabolic syndrome X, peripheral vascular disease, chronic obstructive pulmonary disease (COPD), emphysema, asthma, idiopathic pulmonary fibrosis, pulmonary fibrosis, adult respiratory distress syndrome, osteoporosis, Paget's disease, coronary calcification, polyarteritis nodosa, polymyalgia rheumatica, Wegener's granulomatosis, central nervous system vasculitis (CNSV), Sjogren's syndrome, scleroderma, polymyositis, AIDS inflammatory response, influenza, avian flu, viral pneumonia, endotoxic shock syndrome, sepsis, sepsis syndrome, trauma/wound, corneal ulcer, chronic/non-healing wound, reperfusion injury (prevent and/or treat), ischemic reperfusion injury (prevent and/or treat), spinal cord injuries (mitigating effects), cancers, myeloma/multiple myeloma, ovarian cancer, breast cancer, colon cancer, bone cancer, osteoarthritis, allergic rhinitis, cachexia, Alzheimer's disease, implanted prosthesis, biofilm formation, dermatitis, acute and chronic, eczema, psoriasis, contact dermatitis, erectile dysfunction, macular degeneration, nephropathy, neuropathy, Parkinson's Disease, peripheral vascular disease, and meningitis, cognition and rejection after organ transplantation. Inflammatory diseases can be bacterial, fungal, parasitic and/or viral in nature.

As used herein, a "diabetic complication" is meant to mean complications induced by an increase in plasma glucose levels above normal level. Examples include, but are not limited to nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction, gastroparesis, diseases associate with the autonomic nervous system, nerve condition abnormalities, i.v. contrast induced nephropathy, small vessel diseases (both within the brain and outside the brain), hypogonadism and heart failure.

As used herein, "effective amount" of a compound is meant to mean a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "treat" is meant to mean administer a compound or molecule of the invention to a subject, such as a human or other mammal (for example, an animal model), that has a Lipid Disorder, or that has coronary artery disease, rheumatoid arthritis, and/or systemic lupus, in order to prevent or delay a worsening of the effects of the disease or condition, or to partially or fully reverse the effects of the disease.

As used herein, "prevent" is meant to mean minimize the chance that a subject who has an increased susceptibility for developing diabetes will develop diabetes.

As used herein, "specifically binds" is meant that an antibody recognizes and physically interacts with its cognate antigen (for example, the disclosed synthetic apolipoprotein E-mimicking peptides) and does not significantly recognize and interact with other antigens; such an antibody may be a polyclonal antibody or a monoclonal antibody, which are generated by techniques that are well known in the art.

As used herein, "probe," "primer," or oligonucleotide is meant to mean a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acids capable of encoding the disclosed synthetic apolipoprotein E-mimicking peptide (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid capable of encoding the disclosed synthetic apolipoprotein E-mimicking peptide to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, and electrophoretic mobility shift assay (EMSA).

As used herein, "specifically hybridizes" is meant to mean that a probe, primer, or oligonucleotide recognizes and physically interacts (that is, base-pairs) with a substantially complementary nucleic acid (for example, a nucleic acid capable of encoding the disclosed synthetic apolipoprotein E-mimicking peptide) under high stringency conditions, and does not substantially base pair with other nucleic acids.

As used herein, "high stringency conditions" is meant to mean conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the

2. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Also disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein.

Methods of Use

The invention also provides many therapeutic methods of using the nucleic acids, peptides, polypeptides, vectors, antibodies, and compositions disclosed herein. For example, disclosed are methods of decreasing the concentration of plasma glucose in a subject, comprising: administering a synthetic apolipoprotein E-mimicking peptide to the subject, whereby the concentration of plasma glucose in the subject decreases. The Examples section below provides examples of how the nucleic acids, peptides, polypeptides, vectors, and antibodies, and compositions of the invention can be used and tested. One of skill in the art would be capable of modifying the methods provided in the Examples section to test and use the nucleic acids, peptides, polypeptides, vectors, antibodies, and compositions disclosed herein. Subjects may be a mammal, such as a human. Additionally, the subject can be an animal which can be a model system used to test human therapeutics. Non-limiting examples of such animals include dog, pig, primate, murine, feline, bovine, or equine animals.

As described above, the synthetic apolipoprotein E-mimicking peptide can be a dual-domain ApoE mimicking peptide or a single-domain ApoE mimicking peptide. For example, the synthetic apolipoprotein E-mimicking peptide can comprise a sequence selected from the group consisting of SEQ ID NOs: 11-14, 18-57, 60, 61, and 62-103. Also disclosed are methods of decreasing the concentration of plasma glucose in a subject, comprising: administering a synthetic apolipoprotein E-mimicking peptide to the subject, whereby the concentration of plasma glucose in the subject decreases, wherein the synthetic apolipoprotein E-mimicking peptide is administered in a composition comprising a pharmaceutically acceptable carrier.

Also disclosed are methods of decreasing the concentration of plasma glucose in a subject, comprising: administering a pharmaceutical composition comprising a synthetic apolipoprotein E-mimicking peptide and a pharmaceutically acceptable carrier to the subject, whereby the concentration of plasma glucose in the subject decreases.

In the methods described herein, the synthetic apolipoprotein E-mimicking peptides can be administered as a composition comprising the synthetic apolipoprotein E-mimicking peptide and a pharmaceutically acceptable carrier. Subjects for the disclosed methods can have type 1, type 2, gestational diabetes (occurring during pregnancy), juvenile onset diabetes, diabetic nephropathy, diabetic neuropathy, and diabetic retinopathy.

Insulin Resistance

Insulin resistance is prevalent in 20-25% of the population, and the condition is a chief component of Type 2 Diabetes Mellitus and a risk factor for cardiovascular disease and certain forms of cancer (Reaven G M, Panminerva Med. 2005, 47: 201-210). Obesity predisposes individuals to the development of insulin resistance, and several mechanisms have been proposed to explain how increased adiposity antagonizes insulin-stimulation of nutrient uptake and storage. In some obese individuals, increased adipose tissue mass may trigger the synthesis and/or secretion of glucocorticoids (Hermanowski-Vosatka, J Exp Med. 2005 Aug. 15; 202: 517-527) or inflammatory cytokines (e.g., tumor necrosis factor alpha) (Hotamisligl G S, Exp Clin Endocrinol Diabetes. 1999; 107 (2):119-25), which inhibit insulin action in peripheral tissues. Additionally, excess lipids may be delivered to non-adipose tissues which are not suited for fat storage (i.e., skeletal muscle and the liver), thus leading to the formation of specific metabolites that directly antagonize insulin signaling and action (Schmitz-Peiffer C, Cell Signal. 2000 October; 12 (9-10):583-94; McGarry J D, Diabetes. 2002 January; 51(1): 7-18).

The disclosed peptides can also be used to modulate insulin resistance. For example, disclosed herein are methods of modulating insulin resistance in a subject, comprising: administering to the subject one or more of the disclosed dual-domain peptides, thereby modulating insulin resistance in the subject.

Also disclosed herein are methods of modulating insulin resistance in a cell, comprising identifying a cell in need of modulated insulin resistance, and administering to the cell one or more of the disclosed dual-domain peptides, thereby modulating insulin resistance in a cell.

As described elsewhere herein, the cell can be in vitro, in vivo, or ex vivo. When the cell is in a subject, the subject can have any one or more of the following diseases and disorders: metabolic syndrome, obesity, diabetes (such as Type II), or Cushing's disease. The subject can also have inflammation. The subject can also have Gaucher disease. These diseases and disorders, as well as others, are disclosed in more detail elsewhere herein.

As described above, insulin resistance can be manifested in several ways, including Type 2 Diabetes. Type 2 diabetes is the condition most obviously linked to insulin resistance. Compensatory hyperinsulinemia helps maintain normal glucose levels—often for decades—before overt diabetes develops. Eventually the beta cells of the pancreas are unable to overcome insulin resistance through hypersecretion. Glucose levels rise, and a diagnosis of diabetes can be made. Patients with type 2 diabetes remain hyperinsulinemic until they are in an advanced stage of disease.

Insulin resistance can also include hypertension. One half of patients with essential hypertension are insulin resistant and hyperinsulinemic. There is evidence that blood pressure is linked to the degree of insulin resistance.

Hyperlipidemia is also associated with insulin resistance. The lipid profile of patients with type 2 diabetes includes decreased high-density lipoprotein cholesterol levels (a significant risk factor for heart disease), increased serum very-low-density lipoprotein cholesterol and triglyceride levels and increased small dense low-density lipoprotein cholesterol level. Insulin resistance has been found in persons with low levels of high-density lipoprotein. Insulin levels have also been linked to very-low-density lipoprotein synthesis and plasma triglyceride levels.

Atherosclerotic heart disease is also associated with insulin resistance, as is obesity. Many persons with one or more of the conditions listed above are obese. Obesity is a component of the syndrome, but it promotes insulin resistance rather than resulting from it. Other abnormalities linked to insulin resistance include hyperuricemia, elevated levels of plasminogen activator inhibitor 1 and a preponderance of small-size, low-density lipoprotein particles. Higher plasminogen activator inhibitor 1 levels and decreased low-density lipoprotein particle diameter are thought to increase the risk of coronary heart disease.

Metabolic Syndrome (also known as Syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL—less than 40 mg/dL; pro-thrombotic state (e.g., high fibrinogen or plasminogen activator inhibitor in the blood); or blood pressure of 130/85 mmHg or higher. A connection has been found between Metabolic Syndrome and other conditions such as obesity, high blood pressure and high levels of LDL "bad" cholesterol, all of which are risk factors for Cardiovascular Disease. For example, an increased link between Metabolic Syndrome and atherosclerosis has been shown. People with Metabolic Syndrome are also more prone to developing Type 2 Diabetes, as well as PCOS (Polycystic Ovarian Syndrome) in women and prostate cancer in men.

Disclosed herein are methods of treating a subject with Syndrome X, comprising identifying a subject with Syndrome X, and administering to the subject one or more of the disclosed dual-domain peptides, thereby treating the subject.

Delivery of Compositions

For delivery of the compositions of the invention to a cell, either in vitro or in vivo, a number of direct delivery systems can be used. These include liposome fusion, gene gun injection, endocytosis, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject. Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Therapeutic Uses

In general, when used for treatment, the therapeutic compositions may be administered orally, parenterally (e.g., intravenously or subcutaneous administration), by intramuscular injection, by intraperitoneal injection, transdermally, extracorporeally, by intracavity administration, transdermally, or topically or the like, including topical intranasal administration or administration by inhalant. The topical administration can be ophthalmically, vaginally, rectally, or intranasally. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or vector used, its mode of administration and the like. An appropriate amount for a particular composition and a particular subject can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. Parenteral administration includes use of a slow release, a time release or a sustained release system such that a constant dosage is maintained.

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage'can vary, and can be administered in one or more dose administrations daily, for one or several days. Guidance can be found in the literature for appropriate dosages for given classes of pharmaceutical products. For example, disclosed are methods comprising administering one or more of the disclosed synthetic apolipoprotein E-mimicking peptides to a subject, whereby the concentration of plasma glucose in the subject decreases, thereby treating diabetes in the subject, wherein said synthetic apolipoprotein E-mimicking peptide is administered in an amount of about 0.001 mg/kg to about 5 mg/kg.

Following administration of a disclosed composition, such as a synthetic apolipoprotein E-mimicking peptide, for treating, inhibiting, or preventing diabetes, the efficacy of the therapeutic peptide can be assessed in various ways well known to the skilled practitioner. For instance, one of ordinary skill in the art will understand that a composition, such as a peptide, disclosed herein is efficacious in treating or inhibiting diabetes in a subject by observing that the composition reduces plasm glucose levels or reduces the amount of glucose present in an assay, as disclosed herein. The compositions that inhibit increased plasm glucose levels or increases insulin levels, as disclosed herein may be administered prophylactically to patients or subjects who are at risk for diabetes.

The peptides, polypeptides, nucleic acids, antibodies, vectors and therapeutic compositions of the invention can be combined with other well-known therapies and prophylactic vaccines already in use. The compositions of the invention can also be used in combination with drugs used to treat diabetic patients/treat low insulin levels/increase insulin levels. Such drugs include ACE-I, ARB-I. ASA, TZD's fibrates, statins, niclosamide, PPAR-α, PPAR-δ, PPAR γ, niacin, insulin, sulfonylurea, metformin, glyburide, Ezetimibe. As such, the peptides, polypeptides, nucleic acids, antibodies, vectors and therapeutic compositions of the invention can be combined with other well-known therapies and prophylactic vaccines already in use and/or in combination with drugs used to treat diabetic patients/treat low insulin levels/increase insulin levels in any of the methods disclosed herein.

The disclosed peptides, when used in combination with other drugs used to treat diabetic patients/treat low insulin levels/increase insulin levels can also help reduce the side-effects known to be associated with other drugs used to treat diabetic patients/treat low insulin levels/increase insulin levels. For example, the disclosed peptides can be used in combination with statins, such that the dosage of the statins administered to a subject can be reduced and therefore the side-effects associated with statin administration can be reduced or abrogated entirely.

In addition, the compositions, including dual-domain peptides, disclosed herein can be used in combination with other peptides. Examples of other peptides that can be used in combination with the current compositions include, but are not limited to the peptides described in U.S. Pat. Nos. 6,664,230; 6,933,279; 7,144,862; 7,166,578; 7,199,102; and 7,148,197; all of which are hereby incorporated by reference in their entirety. Other peptides that can be used in combination with the current compositions include, but are not limited to the peptides described in U.S. Patent Application Nos. 60/494,449; 11/407,390; and Ser. No. 10/913,880; all of which are hereby incorporated by reference in their entirety. The compositions of the invention can be combined with any of these drugs. The combination of the peptides of the invention can generate an additive or a synergistic effect with current treatments. As such, the compositions, including dual-domain peptides, disclosed herein can be used in combination with other peptides in any of the methods disclosed herein.

Furthermore, the disclosed compositions can be administered in conjunction with a drug selected from the group consisting of CETP inhibitors, FTY720, Certican, DPP4 inhibitors, Calcium channel blockers, ApoA1 derivative or mimetic or agonist, PPAR agonists, Steroids, Gleevec, Cholesterol Absorption blockers (Zetia), Vytorin, Any Renin Angiotensin pathway blockers, Angiotensin II receptor antagonist (Diovan, etc.), ACE inhibitors, Renin inhibitors, MR antagonist and Aldosterone synthase inhibitor, Beta-blockers, Alpha-adrenergic antagonists, LXR agonist, FXR agonist, Scavenger Receptor B1 agonist, ABCA1 agonist, Adiponectic receptor agonist or adiponectin inducers, Stearoyl-CoA Desaturase I (SCD1) inhibitor, Cholesterol synthesis inhibitors (non-statins), Diacylglycerol Acyltransferase I (DGAT1) inhibitor, Acetyl CoA Carboxylase 2 inhibitor, PAI-1 inhibitor, LP-PLA2 inhibitor, GLP-1, Glucokinase activator, CB-1 agonist, AGE inhibitor/breaker, PKC inhibitors, Anti-thrombotic/coagulants: Aspirin, ADP receptor blockers e.g., Clopidigrel, Factor Xa inhibitor, GPIIb/IIIa inhibitor, Factor VIIa inhibitor, Warfarin, Low molecular weight heparin, Tissue factor inhibitor, Anti-inflammatory drugs: Probucol and derivative, e.g., AGI-1067 etc, CCR2 antagonist, CX3CR1 antagonist, IL-1 antagonist, Nitrates and NO donors, and Phosphodiesterase inhibitors.

For example, disclosed are methods of treating a subject with diabetes comprising administering an effective amount of a synthetic apolipoprotein E-mimicking peptide and a statin to the subject, whereby the concentration of plasma glucose in the subject decreases, thereby treating diabetes in the subject.

Also disclosed are methods of treating a subject with diabetes comprising administering an effective amount of a synthetic apolipoprotein E-mimicking peptide and a statin to the subject, whereby the concentration of plasma glucose in the subject decreases, thereby treating diabetic complications in the subject.

Compositions

As described above, apolipoprotein E-mimicking peptides can be used in a variety of methods. Human apolipoprotein E (apo E) consists of two distinct domains, the lipid-associating domain (residues 192-299) and the globular domain (1-191) which contains the LDL receptor binding site (residues 129-169). To test the hypothesis that a minimal arginine-rich apoE receptor binding domain (141-150) was sufficient to enhance low density lipoprotein (LDL) and very low density lipoprotein (VLDL) uptake and clearance when covalently linked to a class A amphipathic helix, Anantharamaiah et al. synthesized a peptide in which the receptor binding domain of human apo E, LRKLRKRLLR (hApo E[141-150] also referred to as "hE", SEQ ID NO: 1), was linked to 18A, a well characterized high affinity lipid-associating peptide (DWLKAFYDKVAEKLKEAF, also referred to as "18A", SEQ ID NO: 4) to produce a peptide denoted as hApoE[141-150]-18A (also referred to as "hE-18A", SEQ ID NO: 11) (see U.S. Pat. No. 6,506,880, which is hereby incorporated by reference in its entirety for its teaching of specific apolipoprotein E-mimicking peptides and their uses). Also synthesized was an end protected analog of hE-18A, denoted Ac-hE18A-NH$_2$(SEQ ID NO: 12). The importance of the lysine residues and the role of the hydrophobic residues in the receptor binding domain were also studied using two analogs, LRRLRRRLLR-18A (also referred to as "hE(R)-18A", SEQ ID NO: 13) and LRKMRKRLMR-18A (also referred to as "mE18A", SEQ ID NO: 14), whereby the receptor binding domain of human apo E was modified to substitute arginine (R) residues for lysine (K) residues at positions 143 and 146 (SEQ ID NO: 3) and whereby the receptor binding domain of mouse apo E (SEQ ID NO: 2), were linked to 18A, respectively. The effect of the dual character peptides was then determined.

Non-Limiting Examples of Polypeptides and Peptides of the Invention

The present invention is directed to methods of using synthetic apolipoprotein-E mimicking peptides or polypeptides. Non-limiting examples of the synthetic apolipoprotein-E mimicking peptides or polypeptides that can be used in the disclosed methods are provided below.

Disclosed herein are synthetic apolipoprotein E-mimicking peptides, consisting of a receptor binding domain of apolipoprotein E comprising the amino acid sequence of SEQ ID NO: 15; and a lipid-associating peptide, wherein said receptor binding domain is covalently linked to said lipid-associating peptide. As such, the receptor binding domain replaced the two leucine (L) residues at positions 148 and 149 of LRKL-RKRLLR (hApo E[141-150], SEQ ID NO: 1) with two phenylalanine (F) residues. The lipid associating peptide for these synthetic apolipoprotein E-mimicking peptides can be the model class A amphipathic helical peptide 18A. For example the lipid-associating peptide can comprise the amino acid sequence of SEQ II) NO: 16 or SEQ ID NO: 17.

Also disclosed herein are synthetic apolipoprotein E-mimicking peptides, comprising: a lipid binding domain of apolipoprotein E comprising the amino acid sequence of SEQ ID NO: 17; and a receptor binding domain peptide, wherein said lipid binding domain is covalently linked to said receptor binding domain peptide. As such, the lipid binding domain replaced the two leucine (L) residues of DWLKAFYDK-VAEKLKEAF (18A, SEQ ID NO: 16) with two phenylalanine (F) residues resulting in the sequence DWFKAFYDK-VAEKFKEAF (SEQ ID NO: 17, also referred to as modified 18A or m18A). The receptor binding domain peptide for the synthetic apolipoprotein E-mimicking peptides can be a human receptor binding domain peptide of ApoE. For example, receptor binding domain peptide of the disclosed synthetic apolipoprotein E-mimicking peptides can comprise the amino acid sequence of SEQ ID NO: 1, SEQ ID NO: 3, or SEQ ID NO: 15. The receptor binding domain peptide of such synthetic apolipoprotein E-mimicking peptides can also be from a species selected from the group consisting of mouse, rabbit, monkey, rat, bovine, pig, and dog.

The receptor binding domain peptide for the synthetic apolipoprotein E-mimicking peptides can also be the LDL receptor (LDLR) binding domain of apolipoprotein B (ApoB). The LDL receptor (LDLR) binding domain of ApoB can have the sequence RLTRKRGLK (SEQ ID NO. 104). ApoB-100 is a 550,000 Da glycoprotein with nine amino acids (3359-3367) serving as the binding domain for the LDL receptor (Segrest et al., J. Lipid. Res. 42, pp. 1346-1367 (2001)). Upon binding to LDLR in clathrin coated pits, LDL is internalized via endocytosis and moves into the endosome where a drop in pH causes the receptor to dissociate from the LDL. The receptor is recycled back to the surface of the cell while the LDL is moved into the lysosome where the particle is degraded (Goldstein et al., Ann. Rev. Cell Biol. 1, pp. 1-39 (1985)). The LDL receptor (LDLR) binding domain of ApoB when used with the disclosed peptides can also be altered and/or modified as described throughout this application for ApoE. For example, LDL receptor (LDLR) binding domain of ApoB can be used with the disclosed lipid-associating peptides, wherein the LDL receptor (LDLR) binding domain of ApoB is covalently linked to said lipid-associating peptide. In addition, the LDL receptor (LDLR) binding domain of ApoB can be scrambled, reverse-oriented, can be part of a domain switched peptide as described below.

As such, also disclosed are methods of methods of decreasing plasma glucose and plasma cholesterol in a subject, comprising administering an effective amount of a synthetic apolipoprotein E-mimicking peptide to the subject, whereby the concentration of plasma glucose and plasma cholesterol are decreased.

Also disclosed are methods of treating a subject with diabetes comprising administering an effective amount of a synthetic apolipoprotein E-mimicking peptide to the subject, whereby the concentration of plasma glucose and plasma cholesterol in the subject decreases, thereby treating diabetes in the subject.

Also disclosed are methods of reducing diabetic complications in a subject comprising administering an effective amount of a synthetic apolipoprotein E-mimicking peptide to the subject, whereby the concentration of plasma glucose and plasma cholesterol in the subject decreases, thereby reducing diabetic complications in the subject.

Examples of receptor binding domain peptides that can be used in the disclosed synthetic apolipoprotein E-mimicking peptides to be used in the disclosed methods are provided in Table 1.

TABLE 1

Disclosed synthetic apolipoprotein E-mimicking peptides to be used in the disclosed methods

| Species | Starting Residue NO: | Sequence | SEQ ID NO: |
|---|---|---|---|
| Human | 141 | LRKLPKRLLR | SEQ ID NO: 1 |
| Rabbit | 134 | LRKLPKRLLR | SEQ ID NO: 5 |
| Monkey | 141 | LRKLRKRLLR | SEQ ID NO: 6 |
| Mouse | 133 | **LRK*MR*KRL*M*R** | SEQ ID NO: 2 |
| Rat | 133 | **LRK*MR*KRL*M*R** | SEQ ID NO: 7 |
| Bovine | 140 | **LRKL*P*KRLLR** | SEQ ID NO: 8 |
| Pig | 140 | **LR*NV*RKRL*V*R** | SEQ ID NO: 9 |
| Dog | 133 | ***M*RKLRKR*V*LR** | SEQ ID NO: 10 |
| R Modified | 141 | **LR*R*LR*R*RLLR** | SEQ ID NO: 3 |
| F Modified | 141 | **LRKLRKR*FF*R** | SEQ ID NO: 15 |
| ApoB | | *RLTRKRGLK* | SEQ ID NO: 104 |

The italicized residues in Table 1 indicate changes from the human sequence; however, the property of the amino acid is conserved. The bold-italicized residues in Table 1 indicate the difference from the human sequence at that position.

Also disclosed are synthetic apolipoprotein E-mimicking peptides that can be used in the disclosed methods, consisting of a combination of the disclosed receptor binding domains of apolipoprotein E and the disclosed lipid-associating peptides, wherein said receptor binding domain is covalently linked to said lipid-associating peptide. Additional lipid-associating peptides that can be used in the disclosed compositions are described in U.S. patent application Ser. No. 11/407,390 (Fogelman et al.), which is hereby incorporated by reference in its entirety for its teaching of lipid-associating peptides. For example, the lipid-associating peptides of Tables 2-6 of U.S. patent application Ser. No. 11/407,390 can be used in the disclosed compositions.

Also disclosed are synthetic apolipoprotein E-mimicking peptides, consisting of a combination of the disclosed receptor binding domains of apolipoprotein B and the disclosed lipid-associating peptides, wherein said receptor binding domain is covalently linked to said lipid-associating peptide. Non-limiting examples of the disclosed synthetic apolipoprotein E-mimicking peptides are provided in Table 2.

Also disclosed are synthetic apolipoprotein E-mimicking peptides that can be used in the disclosed methods, consisting of a combination of the disclosed receptor binding domains of apolipoprotein E and the disclosed lipid-associating peptides, wherein said receptor binding domain is covalently linked to said lipid-associating peptide in a domain switched orientation. Also disclosed are synthetic apolipoprotein E-mimicking peptides, consisting of a combination of the disclosed receptor binding domains of apolipoprotein B and the disclosed lipid-associating peptides, wherein said receptor binding domain is covalently linked to said lipid-associating peptide in a domain switched orientation. These peptides can be referred to as "domain switched" "switched domain", or "switched" peptides. For example, disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide in a domain switched orientation to those described above and in Table 2. Specifically, the lipid-associating peptide is covalently linked to the receptor binding domain of apolipoprotein E such that the lipid-associating peptide is at the N-terminus of the synthetic apolipoprotein E-mimicking peptide. Additional non-limiting examples of the disclosed synthetic apolipoprotein E-mimicking peptides that can be used in the disclosed methods are provided in Table 3.

TABLE 2

Non-limiting examples of the disclosed synthetic apolipoprotein E-mimicking peptides

| Receptor Binding Domains of ApoE | Lipid-Associating Peptides | SEQ ID NO: |
|---|---|---|
| LRKLRKRLLR | DWLKAFYDKVAEKLKEAF | SEQ ID NO: 18 |
| LRKLRKRLLR | DWLKAFYDKVAEKLKEAF | SEQ ID NO: 19 |
| LRKLRKRLLR | DWLKAFYDKVAEKLKEAF | SEQ ID NO: 20 |
| LRKMRKRLMR | DWLKAFYDKVAEKLKEAF | SEQ ID NO: 21 |
| LRKMRKRLMR | DWLKAFYDKVAEKLKEAF | SEQ ID NO: 22 |
| LRKLPKRLLR | DWLKAFYDKVAEKLKEAF | SEQ ID NO: 23 |
| LRNVRKRLVR | DWLKAFYDKVAEKLKEAF | SEQ ID NO: 24 |
| MRKLRKRVLR | DWLKAFYDKVAEKLKEAF | SEQ ID NO: 25 |
| LRRLRRRLLR | DWLKAFYDKVAEKLKEAF | SEQ ID NO: 26 |
| LRKLRKRFFR | DWLKAFYDKVAEKLKEAF | SEQ ID NO: 27 |
| LRKLRKRLLR | DWFKAFYDKVAEKFKEAF | SEQ ID NO: 28 |
| LRKLRKRLLR | DWFKAFYDKVAEKFKEAF | SEQ ID NO: 29 |
| LRKLRKRLLR | DWFKAFYDKVAEKFKEAF | SEQ ID NO: 30 |
| LRKMRKRLMR | DWFKAFYDKVAEKFKEAF | SEQ ID NO: 31 |
| LRKMRKRLMR | DWFKAFYDKVAEKFKEAF | SEQ ID NO: 32 |
| LRKLPKRLLR | DWFKAFYDKVAEKFKEAF | SEQ ID NO: 33 |
| LRNVRKRLVR | DWFKAFYDKVAEKFKEAF | SEQ ID NO: 34 |
| MRKLRKRVLR | DWFKAFYDKVAEKFKEAF | SEQ ID NO: 35 |
| LRRLRRRLLR | DWFKAFYDKVAEKFKEAF | SEQ ID NO: 36 |
| LRKLRKRFFR | DWFKAFYDKVAEKFKEAF | SEQ ID NO: 37 |

The disclosed synthetic apolipoprotein E-mimicking peptides can also be N-terminally protected using acetyl and amino groups.

Also disclosed are synthetic apolipoprotein E-mimicking peptides that can be used in the disclosed methods, consisting of a combination of the disclosed receptor binding domains of apolipoprotein E and the disclosed lipid-associating peptides, wherein said receptor binding domain is covalently linked to said lipid-associating peptide in a domain switched orientation. Also disclosed are synthetic apolipoprotein E-mimicking peptides, consisting of a combination of the disclosed receptor binding domains of apolipoprotein B and the disclosed lipid-associating peptides, wherein said receptor binding domain is covalently linked to said lipid-associating peptide in a domain switched orientation. These peptides can be referred to as "domain switched" "switched domain", or "switched" peptides. For example, disclosed are synthetic apolipoprotein E-mimicking peptides, consisting of a combination of the disclosed receptor binding domains of apolipoprotein E and the disclosed lipid-associating peptides, wherein said receptor binding domain is covalently linked to said lipid-associating peptide in a domain switched orientation to those described above and in Table 2. Specifically, the lipid-associating peptide is covalently linked to the receptor binding domain of apolipoprotein E such that the lipid-associating peptide is at the N-terminus of the synthetic apolipoprotein E-mimicking peptide. Additional non-limiting examples of the disclosed synthetic apolipoprotein E-mimicking peptides that can be used in the disclosed methods are provided in Table 3.

TABLE 3

Additional non-limiting examples of the disclosed synthetic apolipoprotein E-mimicking peptides that can be used in the disclosed methods

| Lipid-associating peptides | Receptor Binding Domains of ApoE | SEQ ID NO: |
|---|---|---|
| DWLKAFYDKVAEKLKEAF | LRKLRKRLLR | SEQ ID NO: 38 |
| DWLKAFYDKVAEKLKEAF | LRKLRKRLLR | SEQ ID NO: 39 |
| DWLKAFYDKVAEKLKEAF | LRKLRKRLLR | SEQ ID NO: 40 |
| DWLKAFYDKVAEKLKEAF | LRKMRKRLMR | SEQ ID NO: 41 |
| DWLKAFYDKVAEKLKEAF | LRKMRKRLMR | SEQ ID NO: 42 |
| DWLKAFYDKVAEKLKEAF | LRKLPKRLLR | SEQ ID NO: 43 |
| DWLKAFYDKVAEKLKEAF | LRNVRKRLVR | SEQ ID NO: 44 |
| DWLKAFYDKVAEKLKEAF | MRKLRKRVLR | SEQ ID NO: 45 |
| DWLKAFYDKVAEKLKEAF | LRRLRRRLLR | SEQ ID NO: 46 |
| DWLKAFYDKVAEKLKEAF | LRKLRKRFFR | SEQ ID NO: 47 |
| DWFKAFYDKVAEKFKEAF | LRKLRKRLLR | SEQ ID NO: 48 |
| DWFKAFYDKVAEKFKEAF | LRKLRKRLLR | SEQ ID NO: 49 |
| DWFKAFYDKVAEKFKEAF | LRKLRKRLLR | SEQ ID NO: 50 |
| DWFKAFYDKVAEKFKEAF | LRKMRKRLMR | SEQ ID NO: 51 |
| DWFKAFYDKVAEKFKEAF | LRKMRKRLMR | SEQ ID NO: 52 |
| DWFKAFYDKVAEKFKEAF | LRKLPKRLLR | SEQ ID NO: 53 |
| DWFKAFYDKVAEKFKEAF | LRNVRKRLVR | SEQ ID NO: 54 |
| DWFKAFYDKVAEKFKEAF | MRKLRKRVLR | SEQ ID NO: 55 |

TABLE 3-continued

Additional non-limiting examples of the disclosed synthetic apolipoprotein E-mimicking peptides that can be used in the disclosed methods

| Lipid-associating peptides | Receptor Binding Domains of ApoE | SEQ ID NO: |
|---|---|---|
| DWFKAFYDKVAEKFKEAF | LRRLRRRLLR | SEQ ID NO: 56 |
| DWFKAFYDKVAEKFKEAF | LRKLRKRFFR | SEQ ID NO: 57 |

The disclosed domain switched synthetic apolipoprotein E-mimicking peptides can also be N-terminally protected using acetyl and amino groups.

Also disclosed are synthetic apolipoprotein E-mimicking peptides that can be used in the disclosed methods, consisting of a combination of the disclosed receptor binding domains of apolipoprotein E and the disclosed lipid-associating peptides, wherein said receptor binding domain is covalently linked to said lipid-associating peptide in a reversed orientation. For example, disclosed are synthetic apolipoprotein E-mimicking peptides, consisting of a combination of the disclosed receptor binding domains of apolipoprotein E and the disclosed lipid-associating peptides, wherein either the sequence of the receptor binding domain or the sequence of the lipid-associating peptide or both sequences are in the reversed oritentation. Also disclosed are synthetic apolipoprotein E-mimicking peptides, consisting of a combination of the disclosed receptor binding domains of apolipoprotein B and the disclosed lipid-associating peptides, wherein said receptor binding domain is covalently linked to said lipid-associating peptide in a reversed orientation. Additional non-limiting examples of the disclosed synthetic apolipoprotein E-mimicking peptides that can be used in the disclosed methods are provided in Table 4.

TABLE 4

Additional non-limiting examples of the disclosed synthetic apolipoprotein E-mimicking peptides that can be used in the disclosed methods

| Receptor Binding Domains of ApoE | Lipid-Associating Peptides | SEQ ID NO: |
|---|---|---|
| RLLRKRLKRL | DWLKAFYDKVAEKLKEAF | SEQ ID NO: 64 |
| RLLRKRLKRL | DWLKAFYDKVAEKLKEAF | SEQ ID NO: 65 |
| RLLRKRLKRL | DWLKAFYDKVAEKLKEAF | SEQ ID NO: 66 |
| RMLRKRMKRL | DWLKAFYDKVAEKLKEAF | SEQ ID NO: 67 |
| RMLRCRMKRL | DWLKAFYDKVAEKLKEAF | SEQ ID NO: 68 |
| RLLRKPLKRL | DWLKAFYDKVAEKLKEAF | SEQ ID NO: 69 |
| RVLRKRVNRL | DWLKAFYDKVAEKLKEAF | SEQ ID NO: 70 |
| RLVRKRLKRM | DWLKAFYDKVAEKLKEAF | SEQ ID NO: 71 |
| RLLRRRLRRL | DWLKAFYDKVAEKLKEAF | SEQ ID NO: 72 |
| RFFRKRLKRL | DWLKAFYDKVAEKLKEAF | SEQ ID NO: 73 |
| RLLRKRLKRL | DWFKAFYDKVAEKFKEAF | SEQ ID NO: 74 |
| RLLRKRLKRL | DWFKAFYDKVAEKFKEAF | SEQ ID NO: 75 |
| RLLRKRLKRL | DWFKAFYDKVAEKFKEAF | SEQ ID NO: 76 |
| RMLRKRMKRL | DWFKAFYDKVAEKFKEAF | SEQ ID NO: 77 |
| RMLRKRMKRL | DWFKAFYDKVAEKFKEAF | SEQ ID NO: 78 |
| RLLRKPLKRL | DWFKAFYDKVAEKFKEAF | SEQ ID NO: 79 |
| RVLRKRVNRL | DWFKAFYDKVAEKFKEAF | SEQ ID NO: 80 |
| RLVRKRLKRM | DWFKAFYDKVAEKFKEAF | SEQ ID NO: 81 |
| RLLRRRLRRL | DWFKAFYDKVAEKFKEAF | SEQ ID NO: 82 |
| RFFRKRLKRL | DWFKAFYDKVAEKFKEAF | SEQ ID NO: 83 |
| LRKLRKRLLR | FAEKLKEAVKDYFAKLWD | SEQ ID NO: 84 |
| LRKLRKRLLR | FAEKLKEAVKDYFAKLWD | SEQ ID NO: 85 |
| LRKLRKRLLR | FAEKLKEAVKDYFAKLWD | SEQ ID NO: 86 |
| LRKMRKRLMR | FAEKLKEAVKDYFAKLWD | SEQ ID NO: 87 |
| LRKMRKRLMR | FAEKLKEAVKDYFAKLWD | SEQ ID NO: 88 |
| LRKLPKRLLR | FAEKLKEAVKDYFAKLWD | SEQ ID NO: 89 |
| LRNVRKRLVR | FAEKLKEAVKDYFAKLWD | SEQ ID NO: 90 |
| MRKLRKRVLR | FAEKLKEAVKDYFAKLWD | SEQ ID NO: 91 |
| LRRLRRRLLR | FAEKLKEAVKDYFAKLWD | SEQ ID NO: 92 |
| LRKLRKRFFR | FAEKLKEAVKDYFAKLWD | SEQ ID NO: 93 |
| LRKLRKRLLR | FAEKFKEAVKDYFAKFWD | SEQ ID NO: 94 |
| LRKLRKRLLR | FAEKFKEAVKDYFAKFWD | SEQ ID NO: 95 |
| LRKLRKRLLR | FAEKFKEAVKDYFAKFWD | SEQ ID NO: 96 |
| LRKMRKRLMR | FAEKFKEAVKDYFAKFWD | SEQ ID NO: 97 |
| LRKMRKRLMR | FAEKFKEAVKDYFAKFWD | SEQ ID NO: 98 |
| LRKLPKRLLR | FAEKFKEAVKDYFAKFWD | SEQ ID NO: 99 |
| LRNVRKRLVR | FAEKFKEAVKDYFAKFWD | SEQ ID NO: 100 |
| MRKLRKRVLR | FAEKFKEAVKDYFAKFWD | SEQ ID NO: 101 |
| LRRLRRRLLR | FAEKFKEAVKDYFAKFWD | SEQ ID NO: 102 |
| LRKLRKRFFR | FAEKFKEAVKDYFAKFWD | SEQ ID NO: 103 |

The disclosed reverse-oriented synthetic apolipoprotein E-mimicking peptides can also be N-terminally and C-terminally protected using acetyl and amide groups.

Also disclosed are synthetic apolipoprotein E-mimicking peptides that can be used in the disclosed methods, consisting of: a receptor binding domain of apolipoprotein E and a lipid-associating peptide, wherein said receptor binding domain is covalently linked to said lipid-associating peptide, wherein the receptor binding domain of apolipoprotein E is scrambled. For example, disclosed is a synthetic apolipoprotein E-mimicking peptide, consisting of: a receptor binding domain of apolipoprotein E comprising the amino acid sequence of SEQ ID NO: 58; and a lipid-associating peptide, wherein said receptor binding domain is covalently linked to said lipid-associating peptide. Also disclosed are synthetic apolipoprotein E-mimicking peptides, consisting of: a receptor binding domain of apolipoprotein B and a lipid-associating peptide, wherein said receptor binding domain is covalently linked to said lipid-associating peptide, wherein the receptor binding domain of apolipoprotein B is scrambled.

Also disclosed are synthetic apolipoprotein E-mimicking peptides that can be used in the disclosed methods, consisting of: a receptor binding domain of apolipoprotein E and a lipid-associating peptide, wherein said receptor binding domain is covalently linked to said lipid-associating peptide, wherein the lipid-associating peptide is scrambled. For example, disclosed herein is a synthetic apolipoprotein E-mimicking peptides, comprising: a lipid binding domain of apolipoprotein E comprising the amino acid sequence of SEQ ID NO: 59 and a receptor binding domain peptide, wherein said lipid binding domain is covalently linked to said receptor binding domain peptide.

Also disclosed are synthetic apolipoprotein E-mimicking peptides that can be used in the disclosed methods, consisting of: a receptor binding domain of apolipoprotein E and a lipid-associating peptide of apolipoprotein E, wherein receptor binding domain is covalently linked to said lipid-associating peptide, wherein both the receptor binding domain and the lipid-associating peptide are scrambled. Additional non-limiting examples of the disclosed scrambled synthetic apolipoprotein E-mimicking peptides that can be used in the disclosed methods are provided in Table 5.

TABLE 5

Additional non-limiting examples of the disclosed scrambled synthetic apolipoprotein E-mimicking peptides that can be used in the disclosed methods

| Name | Receptor Binding Domains of ApoE | Lipid-Associating Peptides | SEQ ID NO: |
|---|---|---|---|
| hE-Sc18A (hE with Sc18A also referred to as Sc2F) | LRKLRKRLLR | KAFEEVLAKKFYDKALWD | SEQ ID NO: 60 |
| SchE-18A | LRLLRKLKRR | DWLKAFYDKVAEKLKEAF | SEQ ID NO: 61 |

The disclosed scrambled synthetic apolipoprotein E-mimicking peptides can also be N-terminally and C-terminally protected using acetyl and amide groups. The disclosed scrambled synthetic apolipoprotein E-mimicking peptides can also be reverse-oriented as described above.

Also disclosed are single-domain synthetic apolipoprotein E-mimicking peptides that can be used in the disclosed methods. The single-domain synthetic apolipoprotein E-mimicking peptides can consist of a receptor binding domain of apolipoprotein E or a lipid-associating peptide. The receptor binding domain or the lipid-associating peptide can be modified or altered as described above. For example, the receptor binding domain or the lipid-associating peptide can be mutated, scrambeled, and/or reverse-oriented. Any other modifications or alterations disclosed herein for the dual-domain polypeptides can also be used for the single-domain peptides.

Numerous other variants or derivatives of the peptides disclosed herein that can be used in the disclosed methods are also contemplated. For example, scrambled peptides can also be reverse-oriented, or can be in a switched orientation. Additionally, reverse-oriented peptides can be in a switched orientation. All other combinations of the disclosed peptides are also contemplated. Non-limiting examples of the peptides have been described herein (see Tables 1-5, for example). As used herein, the term "analog" is used interchangeably with "variant" and "derivative." Variants and derivatives are well understood to those of skill in the art and can involve amino acid sequence modifications. Such, amino acid sequence modifications typically fall into one or more of three classes: substantial; insertional; or deletional variants. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Substitutions, deletions, insertions or any combination thereof may be combined to arrive at a final derivative or analog. Substitutional variants are those in which at least one residue has been removed and a different residue inserted in its place. Such substitutions generally are made in accordance with Tables 6 and 7 and are referred to as conservative substitutions.

Substantial changes in function or immunological identity are made by selecting substitutions that are less conservative than those in Table 6, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties are those in which: (a) the hydrophilic residue, e.g., seryl or threonyl, is substituted for (or by) a hydrophobic residue, e.g., leucyl, isoleucyl, phenylalanyl, valyl or alanyl; Tryptophan, Tyrosinyl (b) a cysteine or proline is substituted for (or by) any other residue; (c) a residue having an electropositive side chain, e.g., lysyl, arginyl, or hystidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

It is understood that one way to define the variants and derivatives of the disclosed proteins herein is to define them in terms of homology/identity to specific known sequences. Specifically disclosed are variants of synthetic apolipoprotein E-mimicking peptides and other proteins or peptides herein disclosed which have at least, 70% or at least 75% or at least 80% or at least 85% or at least 90% or at least 95% homology to the synthetic apolipoprotein E-mimicking peptides specifically recited herein. Those of skill in the art readily understand how to determine the homology of two proteins.

TABLE 6

Amino Acid Substitutions

| Original Residue | Non-Limiting Exemplary Conservative Substitutions |
|---|---|
| Ala | Ser |
| Arg | Gly; Gln; Lys |
| Asn | Gln; His |
| Asp | Glu |
| Cys | Ser |
| Gln | Asn; Lys |
| Glu | Asp |
| Gly | Ala |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

As this specification discusses various polypeptides and polypeptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

TABLE 7

Amino Acid Abbreviations

| Amino Acid | Abbreviations |
|---|---|
| Alanine | Ala (A) |
| Allosoleucine | AIle |
| Arginine | Arg (R) |
| Asparagines | Asn (N) |
| Aspartic Acid | Asp (D) |
| Cysteine | Cys (C) |
| Glutamic Acid | Glu (E) |
| Glutamine | Gln (Q) |
| Glycine | Gly (G) |
| Histidine | His (H) |
| Isolelucine | Ile (I) |
| Leucine | Leu (L) |
| Lysine | Lys (K) |
| Phenylalanine | Phe (F) |
| Praline | Pro (P) |
| Pyroglutamic Acid | PGlu (U) |
| Serine | Ser (S) |
| Threonine | Thr (T) |
| Tyrosine | Tyr (Y) |
| Tryptophan | Trp (W) |
| Valine | Val (V) |

Blocking/Protecting Groups and D Residues

While the various compositions described herein may be shown with no protecting groups, in certain embodiments (e.g., particularly for oral administration), they can bear one, two, three, four, or more protecting groups. The protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. One example of such a "dual protected peptide" is Ac-LRKLRKRLLRD-WLKAFYDKVAEKLKEAF-NH$_2$ (SEQ ID NO:12 with blocking groups), either or both of these protecting groups can be eliminated and/or substituted with another protecting group as described herein.

Without being bound by a particular theory, it was a discovery of this invention that blockage, particularly of the amino and/or carboxyl termini of the subject peptides of this invention can improve oral delivery and can also increase serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. For example, the protecting groups can include, but are not limited to alkyl chains as in fatty acids, propeonyl, formyl, and others. Carboxyl protecting groups include amides, esters, and ether-forming protecting groups can also be used. For example, an acetyl group can be used to protect the amino terminus and an amide group can be used to protect the carboxyl terminus. These blocking groups enhance the helix-forming tendencies of the peptides. Additional blocking groups include alkyl groups of various lengths, e.g., groups having the formula: $CH_3(CH_2)_nCO$ where n ranges from about 1 to about 20, preferably from about 1 to about 16 or 18, more preferably from about 3 to about 13, and most preferably from about 3 to about 10.

Additionally, the protecting groups include, but are not limited to alkyl chains as in fatty acids, propeonyl, formyl, and others. For example, carboxyl protecting groups can include amides, esters, and ether-forming protecting groups. These blocking groups can enhance the helix-forming tendencies of the peptides. Blocking groups can include alkyl groups of various lengths, e.g. groups having the formula: $CH_3(CH_2)_nCO$ where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) Protective Groups in Organic Synthesis, 2$^{nd}$ ed., John Wiley & Sons, Inc. Somerset, N.J.). For example, acetylation can be accomplished during the synthesis when the peptide is on the resin using acetic anhydride. Amide protection can be achieved by the selection of a proper resin for the synthesis.

The compositions disclosed herein can also comprise one or more D-form (dextro rather than levo) amino acids as described herein. For example, at least two enantiomeric amino acids, at least 4 enantiomeric amino acids or at least 8 or 10 enantiomeric amino acids can be in the "D" form amino acids. Additionally, every other, or even every amino acid (e.g., every enantiomeric amino acid) of the peptides described herein is a D-form amino acid. Additionally, at least 50% of the enantiomeric amino acids can be "D" form, at least 80% of the enantiomeric amino acids are "D" form, at least 90%, or even all of the enantiomeric amino acids can be in the "D" form amino acids.

Polypeptide Production

Polypeptides that can be used in the disclosed methods can be produced by any method known in the art. One method of producing the disclosed polypeptides is to link two or more amino acid residues, peptides or polypeptides together by protein chemistry techniques. For example, peptides or polypeptides are chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). A peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, (Grant G A (1992) *Synthetic Peptides: A User Guide*. W.H. Freeman and Co., N.Y. (1992); Bodansky M and Trost B., Ed. (1993) *Principles of Peptide Synthesis*. Springer-Verlag Inc., NY). Alternatively, the peptide or polypeptide is independently synthesized in vivo. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two-step chemical reaction (Dawson et al. *Science*, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolim M et al. (1992) *FEBS Lett.* 307:97-101; Clark-Lewis I et al., *J. Biol. Chem.*, 269:16075 (1994); Clark-Lewis I et al., *Biochem.*, 30:3128 (1991); Rajarathnam K et al., *Biochem.* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

Also disclosed are the components to be used to prepare the disclosed APoE mimicking peptides that can be used in the disclosed methods as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polynucleotide is disclosed and discussed and a number of modifications that can be made to a number of molecules including the polynucleotide are discussed, specifically contemplated is each and every combination and permutation of polynucleotide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that one way to define any known variants and derivatives or those that might arise, of the disclosed genes and proteins herein is through defining the variants and derivatives in terms of homology to specific known sequences. Specifically disclosed are variants of the genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Delivery of Compositions

In the methods described herein, delivery of the compositions (for example, ApoE mimicking polypeptides) to cells can be via a variety of mechanisms. As defined above, disclosed herein are compositions comprising any one or more of the polypeptides, nucleic acids, vectors and/or antibodies described herein can be used to produce a composition of the invention which may also include a carrier such as a pharmaceutically acceptable carrier. For example, disclosed are pharmaceutical compositions, comprising the synthetic apolipoprotein E-mimicking peptides disclosed herein, and a pharmaceutically acceptable carrier The polypeptide can be in solution or in suspension (for example, incorporated into microparticles, liposomes, or cells). These compositions can be targeted to a particular cell type via antibodies, receptors, or receptor ligands. One of skill in the art knows how to make and use such targeting agents with the compositions of the invention. A targeting agent can be a vehicle such as an antibody conjugated liposomes; receptor mediated targeting of DNA through cell specific ligands, and highly specific retroviral targeting of cells in vivo. Any such vehicles can be part of the composition of the invention. In general, receptors are involved in pathways of endocytosis, either constitutive or ligand induced. These receptors cluster in clathrin-coated pits, enter the cell via clatrhin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, ligand valency, and ligand concentration.

For example, the compositions described herein can comprise s pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions may also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium choloride solution, Ringer's dextrose, dextrose and sodium choloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

Methods for making the Compositions of the Invention

The compositions disclosed herein and the compositions necessary to perform the disclosed methods can be made using any method known to those of skill in the art for that particular reagent or compound unless otherwise specifically noted. For example, there are a variety of methods that can be used for making these compositions, such as synthetic chemical methods and standard molecular biology methods.

The peptide or polypeptides disclosed herein can be used to make certain other aspects of the invention. For example, the peptides and polypeptides of the invention can be used to produce the antibodies of the invention. Nucleic acids and vectors of the invention can be used to produce the peptides and polypeptides and other recombinant proteins of the invention. Host cells of the invention can be used to make nucleic acids, proteins, peptides, antibodies, and transgenic animals of the invention. These synthetic methods are described above.

As described above, the polypeptides or peptides of the invention may also be used to generate antibodies, which bind specifically to the polypeptides or fragments of the polypeptides. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention, sequences substantially identical thereto, or fragments of the foregoing sequences.

In immunoaffinity procedures, the antibody is attached to a solid support, such as a bead or column matrix. The protein preparation is placed in contact with the antibody under conditions under which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

The antibodies of the invention can be attached to solid supports and used to immobilize apolipoprotein E or polypeptides of the present invention. Polyclonal antibodies generated against the polypeptides of the invention can be obtained by direct injection of the polypeptides into an animal or by administering the polypeptides to an animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

3. Methods

DM is characterized by low HDL-C, high TG and high sdLDL. Moreover individuals with low HDL may also have hyperinsulinemia and insulin resistance and are at increased risk for developing DM. Clinical studies with drugs and lifestyle modification have demonstrated that increased HDL levels is associated with decrease in the diabetic or cardiovascular disease risk. DM-2 is not only associated with quantitative reduction in HDL but also qualitative changes (The National Institute of Diabetes and Digestive and Kidney Diseases website; Knowler W C et al N Engl J Med. (2002) 346(6):393-403; Shaten B J et al Diabetes Care. (1993) 16:1331-9; Betteridge D J et al Diabetes Research and Clinical Practice (2005) 68S2:S15-2; and The Framingham Heart Study website). Compositional analyses of HDL isolated from DM-2 shows TG enrichment, depletion of cholesterol and enhanced oxidative crosslinking of apolipoprotein (apo) A-I (Betteridge D J et al Diabetes Research and Clinical Practice (2005) 68S2:S15-22, Nicholls S J et al J Am Coll Cardiol. (2006) 47(5):992-7). These changes are associated with attenuation of the anti-inflammatory, anti-oxidant and anti-atheroslertoic properties of HDL and its protein constituent apo A-I. There is increasing evidence for an important role of inflammation in the onset and progression of DM-2. This is supported by the fact that various acute phase reactants such as CRP, IL-1, IL-6, TNF-α and serum amyloid A are elevated in DM-2. Nf-κB may be one of the central mediators of the inflammatory cascade resulting in DM-2. Reactive oxygen species (ROS) also have a causal role in multiple forms of insulin resistance. Houstis et al. demonstrated that increase in ROS precedes the onset of detectable insulin resistance. Further decrease in ROS is associated with improved insulin sensitivity and glucose homeostasis. HDL and its associated proteins such as apo A1 and Paraoxanase (PON) are potent anti-oxidants and may therefore also improved insulin sensitivity or prevent the onset or progression of glucose intolerance in similar fashion. However, DM-2 is associated with decreased levels of HDL and its more potent subspecies HDL-2. Further the HDL present in diabetics is not as potent for reverse cholesterol transport as that obtained from non-diabetics. Furthermore, HDL present in diabetics may not be as effective in preventing LDL oxidation as that from non-diabetics. This indicates that DM-2 is characterized not only by significant pro-oxidant and pro-inflammatory state but also the normal homeostatic mechanisms to counter such mechanisms are dysfunctional at the very least. The oxidant, inflammatory and dyslipidemic effects also result in pancreatic beta cell apoptosis. Loss of beta cells results in decreased insulin secretion and progression of DM-2.

A potential therapeutic target in DM-2 can be lipoproteins, specifically HDL that can also alter the inflammatory milieu. An emerging area in the field of HDL therapy is the development of apo mimetic peptides (Linsel-Nitschke P et al Nat Rev Drug Discov. (2005) 4(3):193-205). In its dextro form, 4F is an orally active (due to synthesis with D-amino acids) apo A-I mimetic peptide that represents a modified form of the high affinity lipid-associating peptide 18A (DWLKAFY-DKVAEKLKEAF) (SEQ ID NO: 16) (Linsel-Nitschke P et at Nat Rev Drug Discov. (2005) 4(3):193-205; Otvos J D et al Circulation. (2006); 113(12):1556-63; Brown B G et al N Engl J Med. (2001) 345(22):1583-92; Nissen S E et al JAMA. (2007); 297(12):1362-73). This class A amphipathic helical peptide forms small HDL-like particles or pre-β HDL (Linsel-Nitschke P et al Nat Rev Drug Discov. (2005) 4(3):193-205). D-4F stimulates an increase in plasma HDL concentration and/or paraoxonase-1 (PON-1), an antioxidant enzyme that hydrolyzes oxidized phospholipids (Linsel-Nitschke P et al Nat Rev Drug Discov. (2005) 4(3):193-205). Incubation of human endothelial cells with an apo A-I mimetic peptide mimics the ability of native HDL to inhibit LDL oxidation (Brown B G et al N Engl J Med. (2001) 345(22):1583-92; Nissen S E et al JAMA. (2007); 297(12): 1362-73). This class A amphipathic helical peptide forms small HDL-like particles or pre-HDL (Linsel-Nitschke P et al Nat Rev Drug Discov. (2005) 4(3): 193-205). D-4F stimulates an increase in plasma HDL concentration and/or paraoxonase-1 (PON-1), an antioxidant enzyme that hydrolyzes oxidized phospholipids (tinsel-Nitschke P et al. Nat Rev Drug Discov. (2005) 4(3): 193-205). Incubation of human endothelial cells with an apo A-I mimetic peptide mimics the ability of native HDL to inhibit LDL oxidation (Brown B G et al N Engl J Med. (2001) 345(22):1583-92; FIELD investigators Lancet (2005) 366: 1849-1861; Nissen S E et at al N Eng! J Med. (2007); 356 (13):1304-16). Apo A-I mimetic peptides also reduce LDL-induced monocyte chemotactic activity and macrophage infiltration into the aortic arch of hypercholesterolemic mice (Linsel-Nitschke P et al Nat Rev Drug Discov. (2005) 4(3): 193-205). Other studies show that an apo A-I mimetic exerts anti-inflammatory effects by inhibiting interleukin-6 expression (Navab M et al Nat Clin Pract Endocrinol Metab. (2006) 2(9):504-11). As disclosed elsewhere herein, there is another class of peptides termed dual domain peptides. These peptides also inhibit superoixde production and improve endothelial function. In contrast to apo A-I mimetics like 4F, these peptides also clear the atherogenic lipoproteins from the plasma similar to apolipoprotein E. Therefore these peptides possess lipid lowering and also anti-oxidant and anti-inflammatory properties. For example, as described below, the peptide L-4F improves glucose homeostasis in ZDF rats, a well validated model of DM-2. Described below are methods that employ the use of the described dual domain peptides.

Disclosed herein are methods of decreasing the concentration of plasma glucose in a subject. For example, disclosed are methods of decreasing the concentration of plasma glucose in a subject, comprising: administering a synthetic apolipoprotein E-mimicking peptide to the subject, whereby the concentration of plasma glucose in the subject decreases.

Also disclosed are methods of decreasing the concentration of plasma glucose in a subject, comprising: administering a synthetic apolipoprotein E-mimicking peptide to the subject, whereby the concentration of plasma glucose in the subject decreases, and wherein the synthetic apolipoprotein E-mimicking peptide is administered in a composition comprising a pharmaceutically acceptable carrier.

Also disclosed are methods for decreasing the concentration of plasma glucose in a subject. For example, disclosed are methods for decreasing the concentration of plasma glucose in a subject comprising: administering a pharmaceutical composition comprising a synthetic apolipoprotein E-mimicking peptide and a pharmaceutically acceptable carrier to the subject, whereby the concentration of plasma glucose in the subject decreases.

Also disclosed are methods of treating a subject with diabetes. For example, disclosed are methods of treating a subject with diabetes comprising administering an effective amount of a synthetic apolipoprotein E-mimicking peptide to the subject, whereby the concentration of plasma glucose in the subject decreases.

Further disclosed are methods of treating a subject with diabetes comprising administering an effective amount of a pharmaceutical composition comprising a synthetic apolipoprotein E-mimicking peptide and a pharmaceutically acceptable carrier to the subject, whereby the concentration of plasma glucose in the subject decreases.

The peptides can also be effective in treating a subject with diabetes and/or reducing diabetic complications in a subject, without an effect on the concentration of plasma glucose in the subject. For example, disclosed are methods of treating a subject with diabetes comprising administering an effective amount of a synthetic apolipoprotein E-mimicking peptide to the subject, wherein the concentration of plasma glucose in the subject is unaltered.

Also disclosed are methods of treating a subject with diabetes comprising administering an effective amount of a synthetic apolipoprotein E-mimicking peptide to the subject, wherein the concentration of plasma glucose in the subject is unaltered.

Also disclosed are methods of reducing diabetic complications in a subject comprising administering an effective amount of a synthetic apolipoprotein E-mimicking peptide to the subject, wherein the concentration of plasma glucose in the subject is unaltered.

Also disclosed are methods of treating a subject with diabetes comprising: (a) selecting a subject with diabetes; and (b) administering an effective amount of a synthetic apolipoprotein E-mimicking peptide to the subject; thereby treating diabetes in the subject. Subjects can be selected using any of the known methods of identifying patients with diabetes. For example, subjects can be selected based on high HgbA1c levels, abnormal plasma glucose levels (for example, via random plasma glucose or fasting plasma glucose tests), the inability to metabolize glucose (for example via a glucose tolerance test), the inability of exogenous insulin to reduce plasma glucose levels (for example via an insulin tolerance test). Subjects can also be selected based on the presence of inflammatory markers such as CRP and SAA, or based on the subject's family history. For example, a subject with a random blood glucose concentration 11.1 mmol/L (200 mg/dL) or a fasting plasma glucose 7.0 mmol/L (126 mg/dL) or a two-hour plasma glucose 11.1 mmol/L (200 mg/dL) during an oral glucose tolerance test can be indicative of a subject with diabetes. A subject with Type 2 DM can be characterized or identified by three pathophysiologic abnormalities: impaired insulin secretion, peripheral insulin resistance, and/or excessive hepatic glucose production.

Also disclosed are methods of treating a subject with diabetes comprising: (a) selecting a subject with diabetes; and (b) administering an effective amount of a pharmaceutical composition comprising a synthetic apolipoprotein E-mimicking peptide and a pharmaceutically acceptable carrier to the subject; thereby treating diabetes in the subject.

Also disclosed are methods of treating a subject with diabetes comprising administering an effective amount of a synthetic apolipoprotein E-mimicking peptide to the subject, whereby the concentration of plasma glucose in the subject decreases, thereby treating diabetes in the subject.

Also disclosed are methods of treating a subject with diabetes comprising administering an effective amount of a pharmaceutical composition comprising a synthetic apolipoprotein E-mimicking peptide and a pharmaceutically acceptable carrier to the subject, whereby the concentration of plasma glucose in the subject decreases, thereby treating diabetes in the subject.

Also disclosed are methods for of treating a subject with diabetes comprising: selecting a subject with diabetes; administering an effective amount of a synthetic apolipoprotein E-mimicking peptide to the subject; thereby treating diabetes in the subject.

Also disclosed are methods for of treating a subject with diabetes comprising: selecting a subject with diabetes; and administering an effective amount of a pharmaceutical composition comprising a synthetic apolipoprotein E-mimicking peptide and a pharmaceutically acceptable carrier to the subject; thereby treating diabetes in the subject.

Diabetic Complications

Diabetic complications affect many organ systems and are responsible for the majority of morbidity and mortality associated with the disease. Chronic complications can be divided into vascular and nonvascular complications. The vascular complications are further subdivided into microvascular (retinopathy, neuropathy, nephropathy) and macrovascular complications (coronary artery disease, peripheral arterial disease, cerebrovascular disease). Nonvascular complications include problems such as gastroparesis, infections, and skin changes. The risk of chronic complications increases as a function of the duration of hyperglycemia; they usually become apparent in the second decade of hyperglycemia. Since type 2 DM often has a long asymptomatic period of hyperglycemia, many individuals with type 2 DM have complications at the time of diagnosis.

Diabetic complications include, but are not limited to, nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction, gastroparesis, diseases associate with the autonomic nervous system, nerve condition abnormalities, i.v. contrast induced nephropathy, small vessel diseases (both within the brain and outside the brain), hypogonadism and heart failure.

As such, disclosed are methods of reducing or treating diabetic complications in a subject comprising: administering a synthetic apolipoprotein E-mimicking peptide to the subject, wherein the diabetic complications in the subject are reduced. Also disclosed are methods as described elsewhere herein, wherein the synthetic apolipoprotein E-mimicking peptide can be used in combination with other with other well-known therapies and prophylactic vaccines already in use and/or in combination with drugs used to treat diabetic patients/treat low insulin levels/increase insulin levels or in combination with drugs used to treat diabetic patients/treat low insulin levels/increase insulin levels.

The synthetic apolipoprotein E-mimicking peptide to be used in the methods described herein can be one or more of any of the apolipoprotein E-mimicking peptides described above. For example, the synthetic apolipoprotein E-mimicking peptide comprises a sequence selected from the group consisting of SEQ ID NOs: 11-14, 18-57, 60, 61, and 62-103. The synthetic apolipoprotein E-mimicking peptide can comprise a receptor binding domain peptide and a lipid-associating peptide, wherein said lipid binding domain peptide is covalently linked to said receptor binding domain peptide.

B-Cell Apoptosis

DM is classified on the basis of the pathogenic process that leads to hyperglycemia, as opposed to earlier criteria such as age of onset or type of therapy. As described above, the two broad categories of DM are designated type 1 and type 2. Type 1A DM results from autoimmune beta cell destruction, which leads to insulin deficiency. Individuals with type 1B DM lack immunologic markers indicative of an autoimmune destructive process of the beta cells. However, they develop insulin deficiency by unknown mechanisms and are ketosis prone.

The disclosed peptides can also be used to inhibit β-cell apoptosis. By inhibiting β-cell apoptosis, β-cell populations can be maintained, thereby retaining insulin levels. By retaining insulin levels, oxidative stress that is often associated with increased plasma glucose levels can be reduced. In other words, by salvaging insulin levels, there is an antioxidant effect.

As such, disclosed are methods of reducing β-cell apoptosis in a subject. For example, disclosed are methods of reducing β-cell apoptosis in a subject, comprising: administering a synthetic apolipoprotein E-mimicking peptide to the subject, whereby β-cell apoptosis in the subject is reduced. Also disclosed are methods of reducing β-cell apoptosis in a subject, comprising: administering a pharmaceutical composition comprising a synthetic apolipoprotein E-mimicking peptide and a pharmaceutically acceptable carrier to the subject, whereby β-cell apoptosis in the subject is reduced. In addition, disclosed are methods of treating a subject with diabetes comprising administering an effective amount of a synthetic apolipoprotein E-mimicking peptide to the subject, whereby β-cell apoptosis in the subject is reduced. Also disclosed are methods of treating a subject with diabetes comprising administering an effective amount of a pharmaceutical composition comprising a synthetic apolipoprotein E-mimicking peptide and a pharmaceutically acceptable carrier to the subject, whereby β-cell apoptosis in the subject is reduced. The subject can be a subject with diabetes or a subject with diabetic complications.

Also disclosed herein are of reducing oxidative stress in a subject. For example, disclosed are methods of reducing oxidative stress in a subject, comprising: administering a synthetic apolipoprotein E-mimicking peptide to the subject, whereby oxidative stress in the subject is reduced. Also disclosed are methods of reducing oxidative stress in a subject, comprising: administering a pharmaceutical composition comprising a synthetic apolipoprotein E-mimicking peptide and a pharmaceutically acceptable carrier to the subject, whereby oxidative stress in the subject is reduced. In addition, disclosed are methods of treating a subject with diabetes comprising administering an effective amount of a synthetic apolipoprotein E-mimicking peptide to the subject, whereby oxidative stress in the subject is reduced. Also disclosed are methods of treating a subject with diabetes comprising administering an effective amount of a pharmaceutical composition comprising a synthetic apolipoprotein E-mimicking peptide and a pharmaceutically acceptable carrier to the subject, whereby oxidative stress in the subject is reduced. The subject can be a subject with diabetes or a subject with diabetic complications.

All the methods above can be carried out as described for the other methods described herein. In addition, the methods above can also be used to both reduce plasma glucose levels as well as to increase insulin levels. For example, plasma glucose levels can be reduced and insulin levels increased in a subject by reducing β-cell apoptosis and/or reducing the oxidative stress of the subject by administering one or more of the disclosed synthetic apolipoprotein E-mimicking peptides alone or in combination with another drug used to treat diabetic patients/treat low insulin levels/increase insulin levels as described above.

Transplantation

Chronic rejection in transplanted hearts or cardiac allograft vasculopathy (CAV) is the leading cause of late death among heart transplant recipients. Strategies to control CAV traditionally have focused on lymphocyte functions. Hsieh et al. have shown that D-4F, a single domain apoA-I mimetic peptide with potent anti-inflammatory/antioxidant properties, can attenuate CAV. (Transplantation (2007) 84(2):238-243). Hsieh et al. used a previously characterized murine model of CAV. B6.C-H2 hearts were heterotopically transplanted into C57BL/6 mice. Recipient mice were treated with either 20 mg of D-4F or carrier daily. Donor hearts were harvested on day 24 after transplantation. Treatment of recipients with D-4F reduced the severity of intimal lesions (62.5+/−3.4% vs. 31.1+/−8.7%, p<0.009). Treatment also resulted in a decrease in the number of graft-infiltrating CD4 and CD8 lymphocytes and CXCR3+ T-lymphocyte subsets. Heme oxygenase-1 (HO-1) gene transcript in the donor hearts was up-regulated with D-4F treatment, and HO-1 blockade partially reversed the beneficial effects of D-4F. In vitro studies showed that D-4F reduced allogeneic T-lymphocyte proliferation and effector cytokine production. These processes were HO-1 independent. This study suggests that D-4F, a prototypical apoA-I mimetic peptide, is effective in controlling CAV via induction of HO-1 in the graft and a direct effect on T-lymphocyte function. This class of peptides with anti-inflammatory/antioxidant properties provides a novel strategy in the treatment of CAV. As such, the disclosed synthetic apolipoprotein E-mimicking peptides can also be used to treat CAV in a subject. For example, disclosed are methods of treating a subject with CAV comprising administering an effective amount of a synthetic apolipoprotein E-mimicking peptide to the subject, whereby the number of graft-infiltrating CD4 and CD8 lymphocytes and CXCR3+ T-lymphocyte subsets is reduced, Heme oxygenase-1 (HO-1) gene transcript is increased, HO-1 blockade is reversed, and/or allogeneic T-lymphocyte proliferation and effector cytokine production are reduced.

The disclosed synthetic apolipoprotein E-mimicking peptides can also be used in pancreatic transplantation. As described above, the disclosed synthetic apolipoprotein E-mimicking peptides can be used to reduce β-cell apoptosis which has a value in β-cell transplantation. By allowing reducing β-cell apoptosis in a subject receiving a pancreas transplant, the subject's β-cells can remain functional and therefore insulin levels can be maintained. As such, oxidative strees can also be reduced in a subject receiving a pancreatic transplant.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

EXAMPLES

Example 1

Previous studies have been conducted with the apo mimetic peptides (4F, Ac-hE18A-NH$_2$) that have demonstrated their anti-oxidant and anti-inflammatory properties. The effects of Ac-hE18A-NH$_2$ in improving endothelial function in WHHL rabbits have also been demonstrated previously (Gupta H et al., Circulation. (2005): 111(23):3112-8). These rabbits have defective LDL receptors and therefore have increased atherogenic lipoproteins (mainly LDL). It was found that a single administration of Ac-hE18A-NH$_2$ peptide resulted in dramatic decrease in total and LDL cholesterol. This was associated with improved aortic endothelial function. This improvement in endothelial function was mediated in part by increase in PON activity with associated decrease in plasma lipid hydroperoxide (FIG. 1). FIG. 1 also shows WHHL rabbits have defective LDL receptor and are therefore prone to atherosclerosis due to dyslipidemia. PON is an antioxidant enzyme associated with HDL and is responsible for scavenging LOOH in plasma. The lipid lowering effects of Ac-hE18A-NH$_2$ in 1% cholesterol fed NZW-rabbits have also been shown. These animals have elevated cholesterol that are rich in VLDL type of particles.

Figure 2:
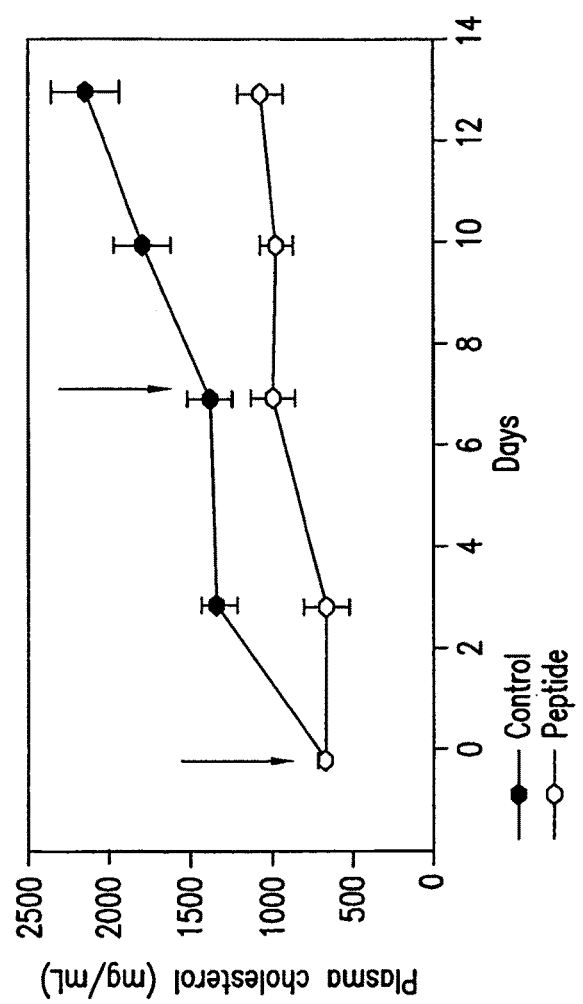
FIG. 2 shows administration of Ac-hE18A-NH$_2$ to high fat diet administered rabbits with initial cholesterol values in the range of 600 mg/dl (1 week on 1% cholesterol diet).

Ac-hE18A-NH$_2$ was administered intravenously two times as shown in the figure (n=4). At the end of 14 days (21 days after the initiation of atherogenic diet), while plasma cholesterol levels in the control rabbits were in the range of 2000 mg/dl (n=4), the peptide administered rabbits showed cholesterol values in the range of 1000 mg/dl. Only 2 administrations of the peptide were effective in significantly reducing total cholesterol (FIG. 2).

In another set of experiments it was noted that Ac-hE18A-NH$_2$ clears the plasma turbidity in 1% cholesterol fed NZW-rabbits. 3 mg/kg of peptide was administered intravenously/week. The rabbits were sacrificed after 51 days from the start of diet. Aortas were harvested and en face analysis was done on Oil Red O stained tissue samples. The results showed that Ac-hE18A-NH$_2$ inhibits atherosclerois in 1% Cholesterol fed NZW rabbits. This was associated with decrease in atherogenic lipoproteins and inhibition of atherosclerosis at day 51.

Figure 3:
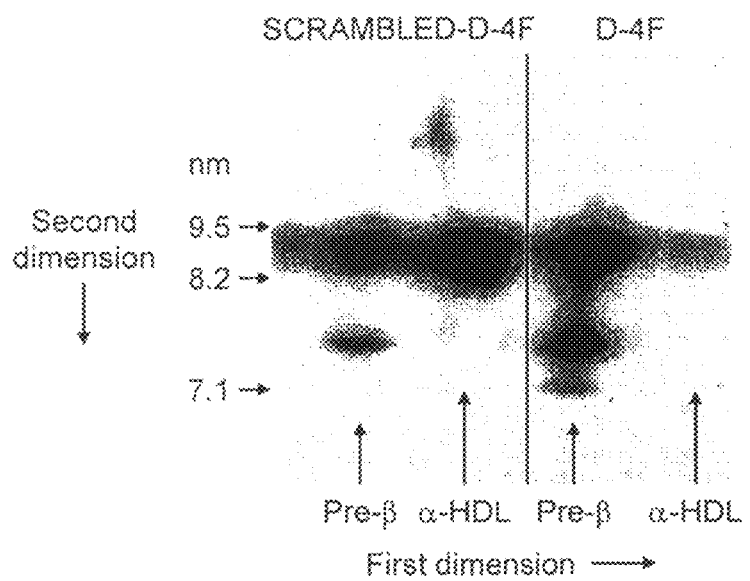
FIG. 3 shows in vitro, in apoE-null mouse plasma, D-4F causes a major redistribution of apoA-I from α-migrating to pre-β migrating particles.

The anti-inflammatory effects of 4F in preventing LPS induced VCAM-1 expression and also sepsis pathways in a rodent model has also been previously reported, as wells as a number of anti-inflammatory and anti-oxidant properties of 4F. One of the important mechanisms of action of 4F can be related to the formation of pre-β HDL as depicted in FIG. 3. It was determined that both D-4F and scrambled D-4F are highly water-soluble. Two milligrams of D-4F or scrambled D-4F (Sc D-4F) was weighed and dissolved in 500 μL of apoE-null mouse plasma and diluted with additional plasma to a final concentration of 500 μg/mL and incubated for 20 minutes at 37° C. with gentle mixing. Plasma was fractionated by agarose electrophoresis in first dimension, and native PAGE in second dimension, and subjected to Western analysis with anti-mouse ApoA-I. FIG. 3 shows in vitro, in apoE-null mouse plasma, D-4F causes a major redistribution of apoA-I from α-migrating to pre-β migrating particles.

Figure 4A:
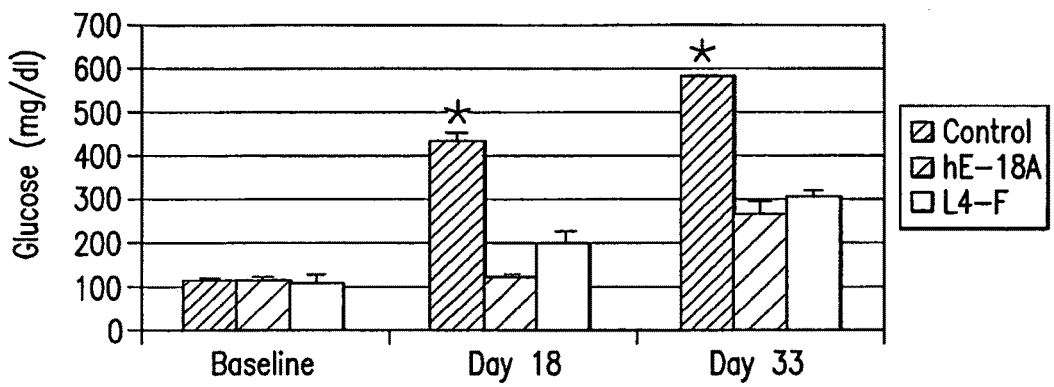
FIGS. 4A and B show the glucose and insulin levels, respectively, of 5-6 week old male ZDF (fa/fa) with defective leptin receptor were administered peptides (5 mg/kg i.v.) that mimic the properties of HDL (Ac-hE-18A-NH$_2$ and L-4F respectively) as compared to the control group (n=7-8/group).
Figure 4B:
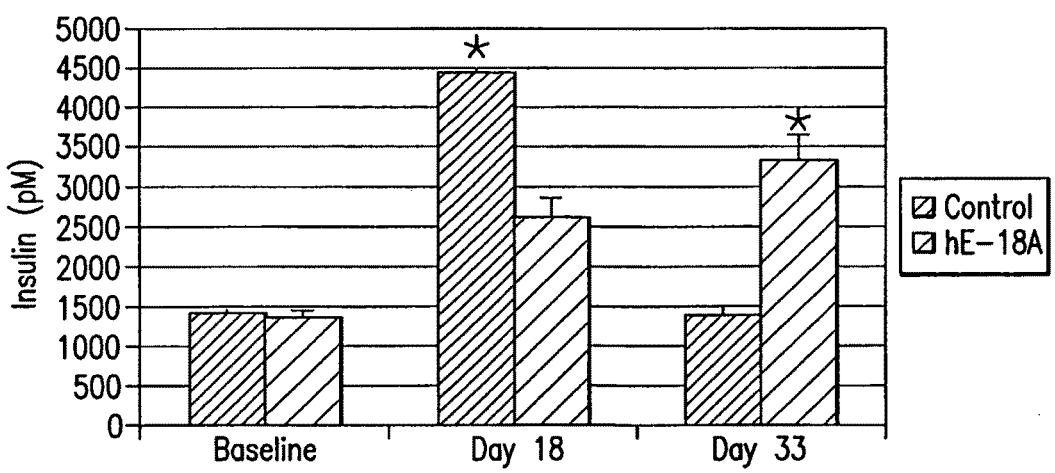

This example outlies studies carried out for the evaluation of the effects of these peptides in the prevention of onset and progression of DM-2. FIG. 4 shows (A) 5-6 week old male ZDF(fa/fa) with defective leptin receptor were administered peptides (5 mg/kg i.v.) that mimic the properties of HDL (Ac-hE18A-NH$_2$ and L-4F respectively) or vehicle (control) alone (n=7-8/group). Baseline fasting plasma was collected prior to peptide administration. Biweekly injections (6 for Ac-hE18A-NH$_2$ group and 5 for L-4F group were administered before day 18). From day 18-day 33, no additional peptide/vehicle injection were performed. Control animals demonstrated increasing fasting plasma glucose levels. In comparison, peptide-treated animals demonstrated only mild increase in plasma glucose at day 18 and day 33. (B) Corresponding insulin levels are depicted in the control and Ac-hE18A-NH$_2$ group only. Control animals become relatively insulin resistant at day 18 as depicted by hyperinsulinemia and hyperglycemia. By day 33, the control animals demonstrate decrease in plasma insulin despite even higher plasma glucose and indicate a loss of beta cell function. In contrast, the Ac-hE18A-NH$_2$ treated animals demonstrate much less insulin resistance at day 18 as depicted by lower plasma insulin levels and normal plasma glucose levels. Despite no additional administration of peptides to these animals, they continue to demonstrate relatively preserved beta cell function with increase in plasma insulin and milder increase in plasma glucose. Data are expressed as Mean±SEM; *p<0.05.

Figure 5:
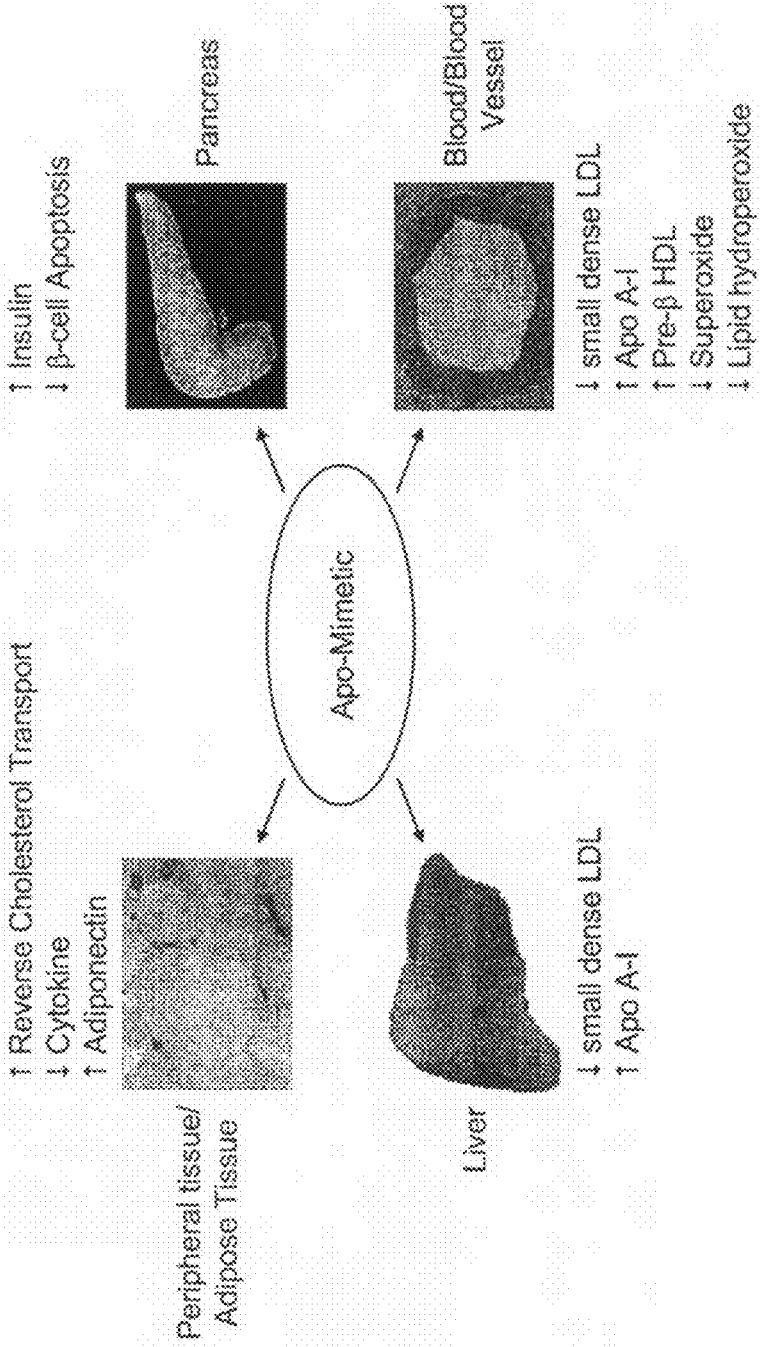
FIG. 5 shows anti-diabetic and anti-atherosclerotic effects of Apo-E mimetic peptides.

The results below show that apo-mimetic peptides are extremely potent in preventing the onset and progression of DM-2 (FIG. 4). Relatively infrequent injections (biweekly) of the peptides as compared to vehicle were able to improve glucose homeostasis in the ZDF rats. Form the studies it was determined that adiponectin levels in the peptide treated animals were much higher than in controls at day 33 (5.7±1 vs. 3±0.2 µl/ml, p<0.05). Adiponectin levels have previously been shown to correlate with insulin sensitivity. Adiponectin also prevents the production and action of pro-inflammatory TNF-α and IL-6 and induces anti-inflammatory cytokine IL-10 and IL-1 receptor antagonist. A summary of the potential effects of the peptides on liver, pancreas, peripheral tissue, blood and blood vessel are depicted in FIG. 5.

Figure 6:
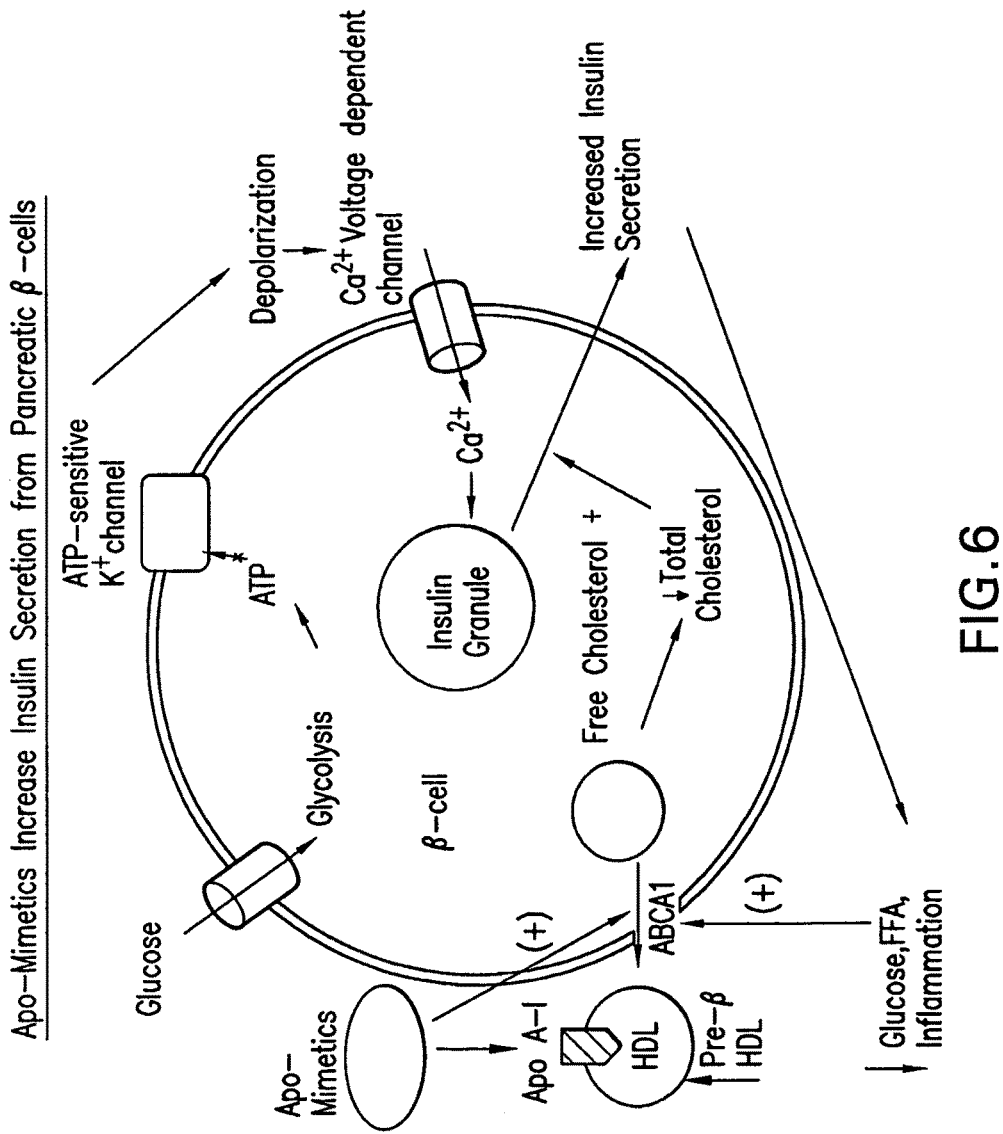
FIG. 6 shows a pathway of how Apo-E mimetic peptides increase insulin secretion from pancreatic β-cells.

It is known that elevated plasma glucose results in secretion of insulin by the pancreatic β-cells which is the result of influx of Ca ions into the cell (FIG. 6). Increased cholesterol in the β-cells can result in inhibition of insulin secretion. Further, inflammatory insults (cytokines, free fatty acids (FFA) and glucose) can inhibit reverse cholesterol transport. The same factors can also promote apoptosis of β-cells and insulin resistance in other tissues. Apolipoproteins and apo-mimetics can inhibit the action of inflammatory insults (cytokines), FFA and glucose by promoting reverse cholesterol transport by stimulating ABCA-1 and formation of pre-β HDL particles. Similarly these mechanisms elsewhere (in blood vessel, peripheral tissue and blood) can cause anti-inflammatory and anti-oxidant effects with increased reverse cholesterol transport, scavenging of lipid hydroperoxides and upregulation of anti-oxidant enzymes such as PON. Some of these peptides also mobilize the atherogenic particles for clearance via liver.

Example 2

Whether apo A-I, HDL lipoproteins and apo-mimetic peptides (4F, Ac-hE18A-NH$_2$) that modulate HDL function can inhibit the onset and progression of DM-2 in rodent models can also be determined. DM-2, as previously described, is characterized by low HDL-C levels with poor HDL quality. This is reflected by impaired anti-inflammatory and anti-oxidant effects. These changes are seen early in the disease process where insulin resistance without elevation in the plasma glucose is noted. Inflammation and oxidant stress are important mediators of insulin resistance. These mechanisms eventually lead to decrease in pancreatic β-cell mass in later stages of DM-2. There are many rodent models of DM-2. ZDF rats with defective leptin receptor are commonly used models of insulin resistance and DM-2. These animals are hyperleptinemic but show impaired leptin actions. Homozygous ZDF (fa/fa) male rats develop insulin resistance early on and when fed a standard diet these animals, demonstrate hyperglycemia by 7 weeks of age. The rats are hyperinsulinemic between 7-10 weeks of age and subsequently the insulin levels drop. By 12 weeks of age these animals demonstrate hypoinsulinemia and hyperglycemia. There is loss of Glut-2 transporters in the pancreatic β-cells and Glut-4 transporters in skeletal muscle of these animals that results in impaired insulin secretion and impaired peripheral glucose uptake. Overall these rodents also demonstrate loss of pancreatic β-cell mass due to apoptosis, as well as other manifestations of DM-2 including hyperlipidemia and multi-organ involvement due to DM-2. Heterozygote ZDF male rats do not demonstrate a diabetic phenotype on standard diet and therefore serve as a good control.

Whether apo A-I and HDL prevent the onset and progression of DM-2 in ZDF (fa/fa) male rats and whether apo-mimetic synthetic peptides (4F, Ac-hE18A-NH$_2$) prevent the onset and progression of DM-2 in ZDF (fa/fa) male rats can also be determined. For such studies, Apo A-I can be isolated from rodents and human plasma using HPLC. HDL can be isolated by centrifugation. Test peptides can be synthesized and scrambled peptide and vehicle will serve as the control for such experiments.

Example 3

As previously described, preliminary observations support the anti-diabetic effects of the apo-mimetic peptides. These effects of the peptides are likely due to three major mechanisms: (i) improved insulin secretion; (ii) decrease in pancreatic β-cell apoptosis or cell death; and/or (iii) improved insulin sensitivity of peripheral tissues. These effects of the peptides are mediated by their anti-inflammatory, anti-oxidant and reverse cholesterol promoting mechanisms and are summarized in FIGS. 5 and 6. As such, whether apo A-I, HDL and apo-mimetic peptides (4F and Ac-hE18A-NH$_2$) prevent apoptosis in pancreatic β-cells, whether apo A-I, HDL and apo-mimetic peptides (4F and Ac-hE18A-NH$_2$) improve peripheral insulin sensitivity, and whether apo A-I, HDL and apo-mimetic peptides (4F and Ac-hE18A-NH$_2$) promote reverse cholesterol transport can also be studied.

What is claimed is:

1. A method of decreasing the concentration of plasma glucose in a subject with diabetes or insulin resistance, comprising: administering a synthetic apolipoprotein E-mimicking peptide to the subject with diabetes or insulin resistance, wherein the peptide consists of a receptor binding domain of apolipoprotein E and a lipid-associating peptide, wherein said receptor binding domain is covalently linked to said lipid-associating peptide, wherein the receptor binding domain contains an acetyl group on the N-terminus and the lipid-associating peptide contains an amide group on the C-terminus, whereby the concentration of plasma glucose in the subject with diabetes or insulin resistance decreases.

2. The method of claim 1, wherein the synthetic apolipoprotein E-mimicking peptide comprises a sequence selected from the group consisting of SEQ ID NOs: 11-14, 18-57, 60, 61, and 62-103.

3. The method of claim 1, wherein the receptor binding domain peptide comprises a sequence selected from the group consisting of SEQ ID NOs: 1-2, 3, 5-10, 15, and 58.

4. The method of claim 3, wherein the lipid-associating peptide is model class A amphipathic helical peptide 18A.

5. The method of claim 1, wherein said lipid-associating peptide comprises a sequence selected from the group consisting of SEQ ID NOs: 4, 16, 17, and 59.

6. The method of claim 1, wherein the synthetic apolipoprotein E-mimicking peptide is administered in a composition comprising a pharmaceutically acceptable carrier.

7. The method of claim 1, wherein the subject has diabetes.

8. The method of claim 1, wherein the receptor binding domain peptide comprises the sequence of SEQ ID NO: 1 and the lipid-associating peptide comprises the sequence of SEQ ID NO: 4.

9. The method of claim 1, wherein the receptor binding domain peptide comprises the sequence of SEQ ID NO: 3 and the lipid-associating peptide comprises the sequence of SEQ ID NO: 4.

10. The method of claim 1, wherein the receptor binding domain peptide comprises the sequence of SEQ ID NO: 15 and the lipid-associating peptide comprises the sequence of SEQ ID NO: 4.

11. The method of claim 1, wherein the receptor binding domain peptide comprises the sequence of SEQ ID NO: 1 and the lipid-associating peptide comprises the sequence of SEQ ID NO: 17.

12. The method of claim 1, wherein the receptor binding domain peptide comprises the sequence of SEQ ID NO: 3 and the lipid-associating peptide comprises the sequence of SEQ ID NO: 17.

13. The method of claim 1, wherein the receptor binding domain peptide comprises the sequence of SEQ ID NO: 15 and the lipid-associating peptide comprises the sequence of SEQ ID NO: 17.

* * * * *